(12) United States Patent
Shirokane et al.

(10) Patent No.: US 11,081,651 B2
(45) Date of Patent: Aug. 3, 2021

(54) ORGANIC SEMICONDUCTOR ELEMENT, ORGANIC SEMICONDUCTOR COMPOSITION, METHOD OF MANUFACTURING ORGANIC SEMICONDUCTOR FILM, ORGANIC SEMICONDUCTOR FILM, AND COMPOUND AND POLYMER USING THE SAME

(71) Applicants: FUJIFILM Corporation, Tokyo (JP); THE UNIVERSITY OF TOKYO, Tokyo (JP)

(72) Inventors: Kenji Shirokane, Kanagawa (JP); Eiji Fukuzaki, Kanagawa (JP); Yukio Tani, Kanagawa (JP); Fumiko Tamakuni, Kanagawa (JP); Yoshihisa Usami, Kanagawa (JP); Tetsuya Watanabe, Kanagawa (JP); Toshihiro Okamoto, Tokyo (JP); Junichi Takeya, Tokyo (JP)

(73) Assignees: FUJIFILM Corporation, Tokyo (JP); The University of Tokyo, Tokyo (JP)

( * ) Notice: Subject to any disclaimer, the term of this patent is extended or adjusted under 35 U.S.C. 154(b) by 10 days.

(21) Appl. No.: 16/588,574

(22) Filed: Sep. 30, 2019

(65) Prior Publication Data
US 2020/0028092 A1 Jan. 23, 2020

Related U.S. Application Data

(63) Continuation of application No. PCT/JP2018/011875, filed on Mar. 23, 2018.

(30) Foreign Application Priority Data

Mar. 31, 2017 (JP) .............................. JP2017-071818

(51) Int. Cl.
*H01L 51/00* (2006.01)
*H01B 1/12* (2006.01)
(Continued)

(52) U.S. Cl.
CPC ............ *H01L 51/0071* (2013.01); *B05D 5/12* (2013.01); *C07D 495/16* (2013.01);
(Continued)

(58) Field of Classification Search
CPC .......... H01B 1/12; H01B 1/121; H01B 1/124; H01L 51/0036; H01L 51/0043;
(Continued)

(56) References Cited

U.S. PATENT DOCUMENTS

2005/0017237 A1 1/2005 Ong et al.
2018/0159043 A1* 6/2018 Fukuzaki ............ H01L 51/0074
(Continued)

FOREIGN PATENT DOCUMENTS

JP 2005-045266 A 2/2005
KR 10-2014-0091487 A 7/2014
WO 2017/022735 A1 2/2017

OTHER PUBLICATIONS

The extended European search report issued by the European Patent Office dated Apr. 9, 2020, which corresponds to European Patent Application No. 18777588.7-1212 and is related to U.S. Appl. No. 16/588,574.
(Continued)

*Primary Examiner* — Mark Kopec
(74) *Attorney, Agent, or Firm* — Studebaker & Brackett PC

(57) ABSTRACT

An organic semiconductor element in which an organic semiconductor layer contains a compound of Formula (1), a compound of Formula (2), and/or a compound of Formula
(Continued)

(3) or contains a polymer having a structure of any one of formed by Formulae (8) to (10):

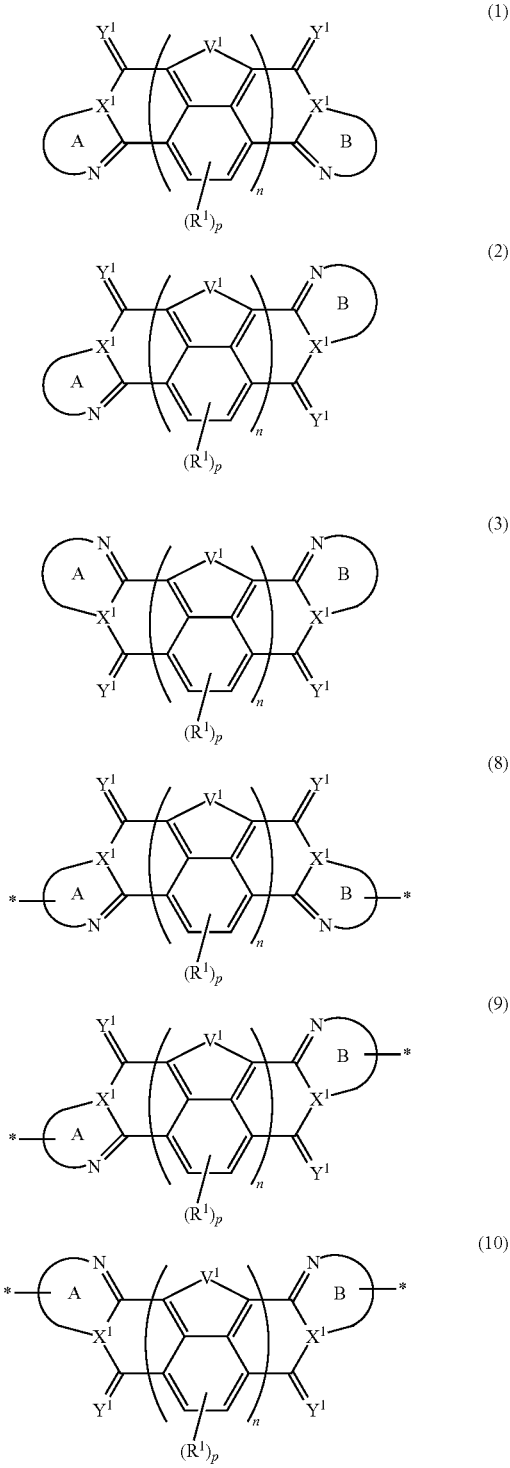

in which $X^1$ represents a nitrogen atom or $CR^a$, and rings A to B each represent a specific nitrogen-containing ring; $Y^1$ represents an oxygen atom, a sulfur atom, $CR^b{}_2$, or $NR^c$; $V^1$ represents $NR^d$, an oxygen atom, a sulfur atom, or a selenium atom; $R^a$ to $R^d$ each represent a hydrogen atom or a substituent; $R^1$ represents a specific substituent, and p is an integer of 0 to 2; n represents 1 or 2; and * represents a bonding site.

18 Claims, 1 Drawing Sheet

(51) Int. Cl.
| | | |
|---|---|---|
| *B05D 5/12* | (2006.01) | |
| *C07D 495/16* | (2006.01) | |
| *C07D 495/22* | (2006.01) | |
| *C07D 517/22* | (2006.01) | |
| *C08G 61/12* | (2006.01) | |
| *H01L 51/05* | (2006.01) | |

(52) U.S. Cl.
CPC ......... *C07D 495/22* (2013.01); *C07D 517/22* (2013.01); *C08G 61/126* (2013.01); *H01B 1/12* (2013.01); *H01L 51/0036* (2013.01); *H01L 51/0043* (2013.01); *H01L 51/0065* (2013.01); *H01L 51/0068* (2013.01); *C08G 2261/124* (2013.01); *C08G 2261/1412* (2013.01); *C08G 2261/18* (2013.01); *C08G 2261/228* (2013.01); *C08G 2261/312* (2013.01); *C08G 2261/324* (2013.01); *C08G 2261/3223* (2013.01); *C08G 2261/3243* (2013.01); *C08G 2261/3246* (2013.01); *C08G 2261/51* (2013.01); *C08G 2261/92* (2013.01); *H01L 51/0545* (2013.01); *H01L 51/0558* (2013.01)

(58) Field of Classification Search
CPC ............ H01L 51/0067; H01L 51/0071; C07D 493/16; C07D 495/16; C07D 495/22; C08G 2261/14; C08G 2261/18; B05D 5/12
See application file for complete search history.

(56) References Cited

U.S. PATENT DOCUMENTS

2020/0028096 A1* 1/2020 Shirokane ........... H01L 51/0072
2020/0343451 A1* 10/2020 Tani ..................... C08G 61/126

OTHER PUBLICATIONS

International Search Report issued in PCT/JP2018/011875; dated Jun. 12, 2018.
International Preliminary Report on Patentability and Written Opinion ssued in PCT/JP2018/011875; dated Oct. 1, 2019.
Subashani Maniam et al.; "Unusual Products from Oxidation of Naphthalene Diimides"; Asian Journal of Organic Chemistry; 2016; pp. 490-493; vol. 5.

* cited by examiner

ORGANIC SEMICONDUCTOR ELEMENT, ORGANIC SEMICONDUCTOR COMPOSITION, METHOD OF MANUFACTURING ORGANIC SEMICONDUCTOR FILM, ORGANIC SEMICONDUCTOR FILM, AND COMPOUND AND POLYMER USING THE SAME

CROSS-REFERENCE TO RELATED APPLICATIONS

This application is a Continuation of PCT International Application No. PCT/JP2018/011875 filed on Mar. 23, 2018, which claims priority under 35 U.S.C. § 119 (a) to Japanese Patent Application No. 2017-071818 filed in Japan on Mar. 31, 2017. Each of the above applications is hereby expressly incorporated by reference, in its entirety, into the present application.

BACKGROUND OF THE INVENTION

1. Field of the Invention

The present invention relates to an organic semiconductor element, an organic semiconductor composition, a method of manufacturing an organic semiconductor film, an organic semiconductor film, and a compound and a polymer using the same.

2. Description of the Related Art

A semiconductor element is used in a liquid crystal display, and a display such as an organic electroluminescent display, a radio frequency identifier (RFID: RF tags), a logic circuit such as a memory, and a solar cell. Among these, an organic semiconductor element having an organic semiconductor film is superior to an inorganic semiconductor element having an inorganic semiconductor film, because weight and cost can be reduced, and flexibility are excellent.

As an organic compound which forms the above organic semiconductor film, a fused polycyclic aromatic compound having a specific structure is reviewed (for example, JP2005-045266A).

SUMMARY OF THE INVENTION

Organic semiconductor devices are generally require heat resistance because the semiconductor devices are incorporated into electronic devices and the like to be used. That is, it is required to continuously exhibit sufficient semiconductor characteristics even in use under high temperature environment.

An object of the present invention is to provide an organic semiconductor element which exhibit desired semiconductor characteristics (for example, higher carrier mobility) and hardly causes deterioration of semiconductor characteristics even in a case of being exposed to a higher temperature environment. Another object of the present invention is to provide an organic semiconductor film suitable as an organic semiconductor layer in the organic semiconductor element and a manufacturing method thereof. Another object of the present invention is to provide a compound, a polymer, and a composition suitable as a constituent material of the organic semiconductor film.

The above problems of the present invention have been solved by the following means.

[1] An organic semiconductor element, comprising: an organic semiconductor layer containing a compound represented by Formula (1), a compound represented by Formula (2), and/or a compound represented by Formula (3), or containing a polymer having at least one structural unit represented by any one of Formulae (8) to (10),

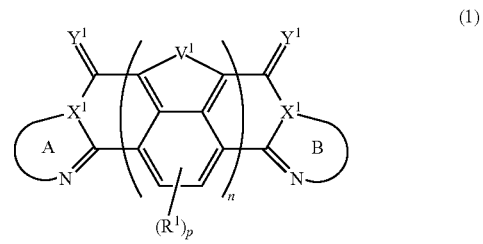

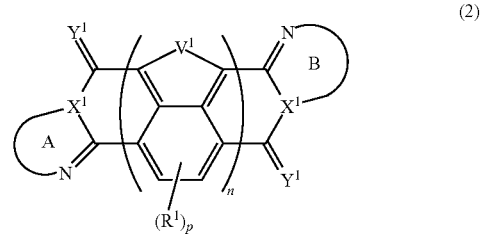

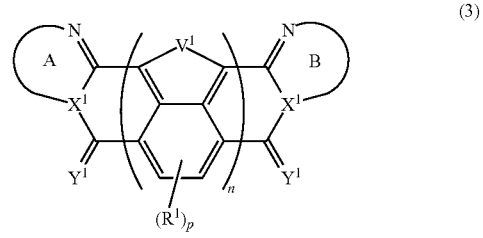

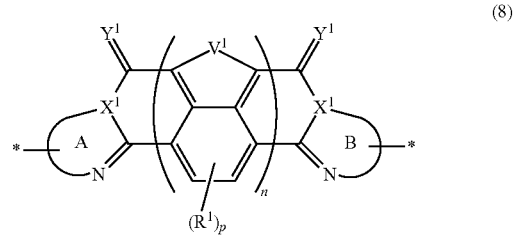

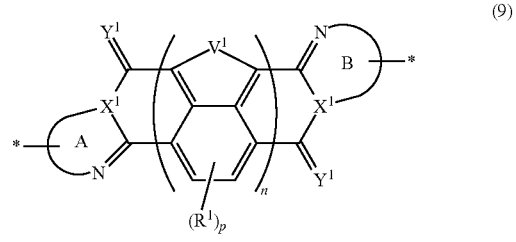

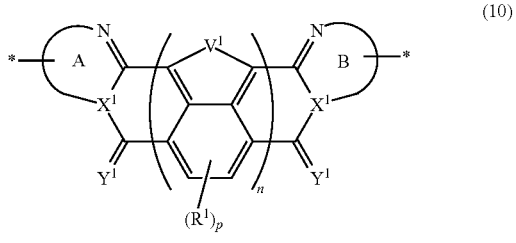

in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b{}_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, $R^1$ represents a halogen atom or a group represented by Formula (W), and p is an integer of 0 to 2, n represents 1 or 2, \* represents a bonding site, $$*-L-T \qquad \text{Formula (W)}$$

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group, \* represents a bonding site,

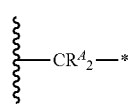
(L-1)

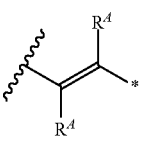
(L-2)

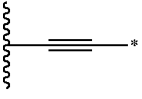
(L-3)

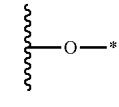
(L-4)

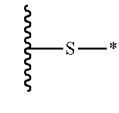
(L-5)

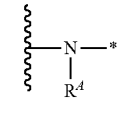
(L-6)

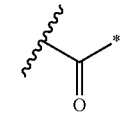
(L-7)

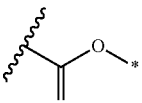
(L-8)

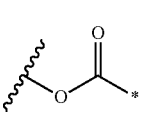
(L-9)

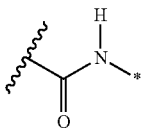
(L-10)

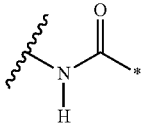
(L-11)

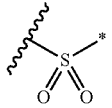
(L-12)

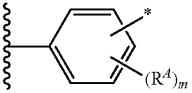
(L-13)

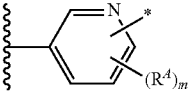
(L-14)

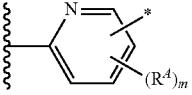
(L-15)

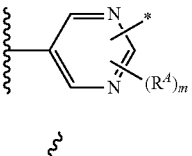
(L-16)

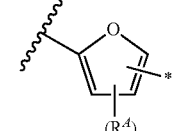
(L-17)

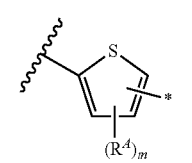
(L-18)

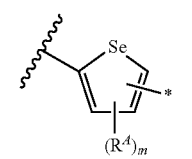
(L-19)

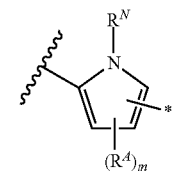
(L-20)

-continued (L-21)

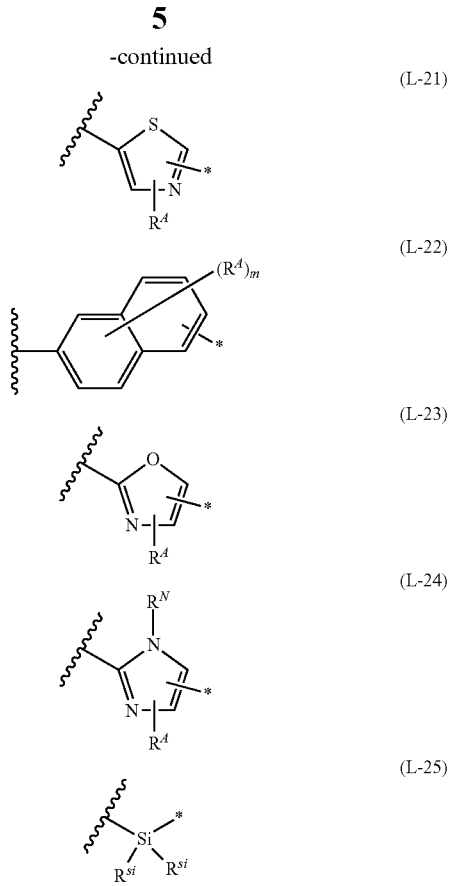

(L-22)

(L-23)

(L-24)

(L-25)

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

[2] The organic semiconductor element according to [1], in which in Formulae (1) to (3), and (8) to (10), $Y^1$ represents an oxygen atom or a sulfur atom.

[3] The organic semiconductor element according to [1] or [2], in which rings A and B each are a fused ring structure represented by Formula (4) or (5), (4)

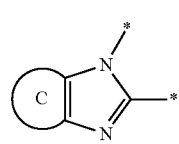

(5)

in each formula, the rings C and D each represent a 5-membered aromatic ring or a 6-membered aromatic ring, or a fused ring including a 5-membered aromatic ring or a 6-membered aromatic ring, $R^2$ represents a hydrogen atom, a halogen atom, or a group represented by Formula (W), and

* represents a bonding site, here, in the fused ring structure represented by Formula (4) or (5) in Formulae (8) to (10), the rings C and D each have one bonding site for being incorporated into a polymer chain.

[4] The organic semiconductor element according to [3], in which the fused ring structure represented by Formula (4) is a fused ring structure represented by Formula (6) or (7), (6)

(7)

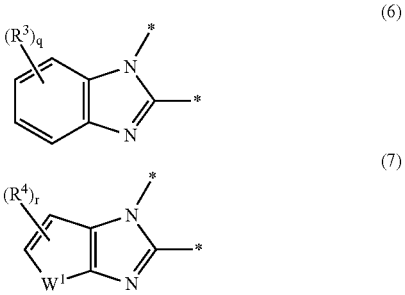

in each formula, $R^3$ and $R^4$ each represent a halogen atom or a group represented by Formula (W), q is an integer of 0 to 4, and r is an integer of 0 to 2, and $W^1$ represents a chalcogen atom, here, in the fused ring structure represented by Formula (6) or (7) in Formulae (8) to (10), one of the ring-constituting atoms of a ring which may have $R^3$ or $R^4$ has a bonding site to be incorporated into a polymer chain.

[5] The organic semiconductor element according to [4], in which the rings A and B each are a fused ring structure represented by Formula (7), here, in the fused ring structure represented by Formula (7) in Formulae (8) to (10), one of the ring-constituting atoms of the ring which may have $R^4$ has one bonding site for being incorporated into a polymer chain.

[6] The organic semiconductor element according to any one of [1] to [5], in which, in Formula (W), L is a divalent group selected from Formulae (L-1), (L-2), (L-3), (L-4), (L-13), (L-17), and (L-18), or a group obtained by bonding two or more divalent groups selected from Formulae (L-1), (L-2), (L-3), (L-4), (L-13), (L-17), and (L-18).

[7] The organic semiconductor element according to any one of [1] to [6], in which the polymer has a structure represented by Formula (G), $$*-Ar^1-(Vr)_{p3}-Ar^2-*$$ Formula (G)

in Formula (G), $Ar^1$ and $Ar^2$ each represent a single bond, or is a vinylene group, an ethynylene group, an arylene group, or a heteroarylene group, or is a divalent group formed by linking two or more groups selected from the vinylene group, the ethynylene group, the arylene group, and the heteroarylene group, and Vr represents a divalent conjugated group having 2 to 40 carbon atoms, and p3 is an integer of 1 to 6.

[8] The organic semiconductor element according to [7], in which the polymers alternately have a structural unit represented by any one of Formulae (8) to (10) and a structure represented by Formula (G).

[9] The organic semiconductor element according to [7] or [8], in which, in Formula (G), Vr is a structure selected from Formulae ($V_D$-1) to ($V_D$-16) and ($V_A$-1) to ($V_A$-11),

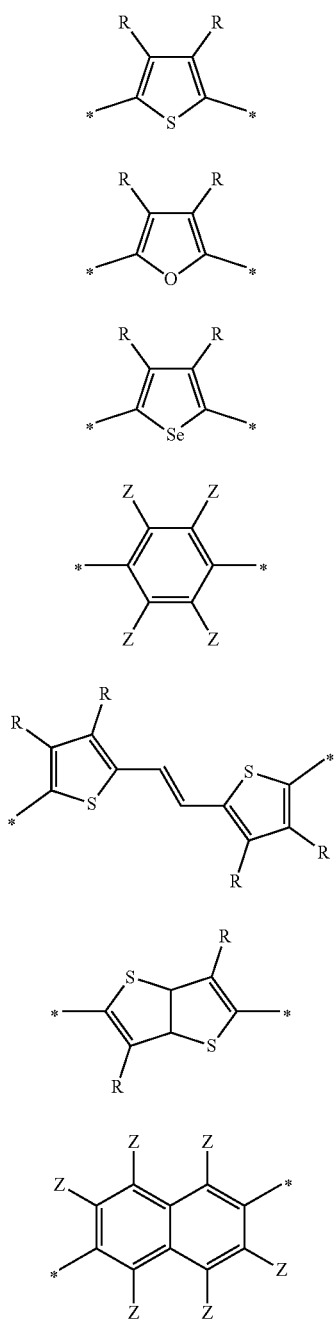

-continued

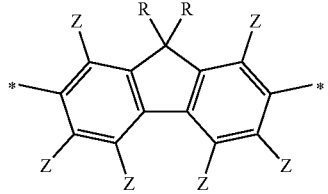

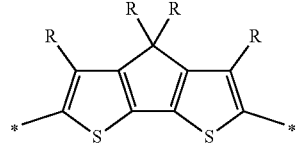

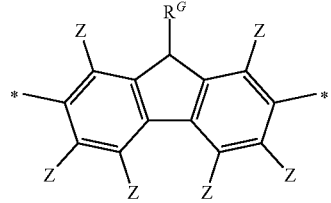

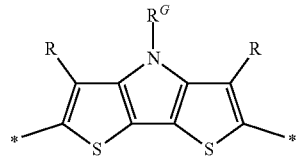

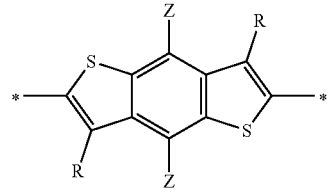

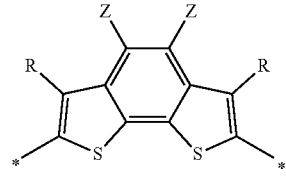

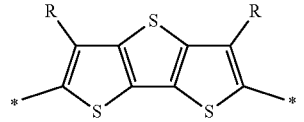

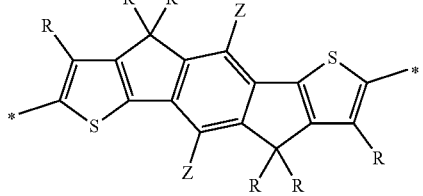

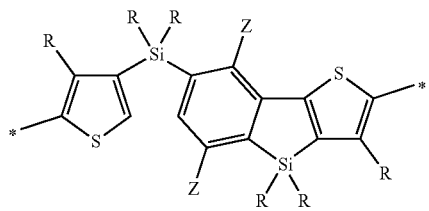
(V<sub>D</sub>-16)

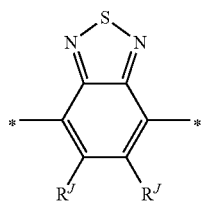
(V<sub>A</sub>-1)

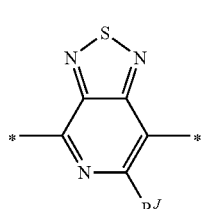
(V<sub>A</sub>-2)

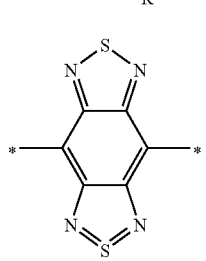
(V<sub>A</sub>-3)

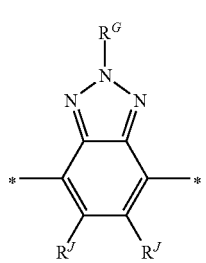
(V<sub>A</sub>-4)

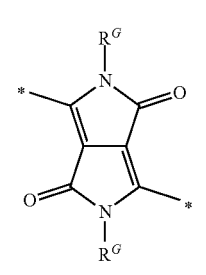
(V<sub>A</sub>-5)

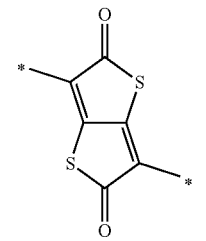
(V<sub>A</sub>-6)

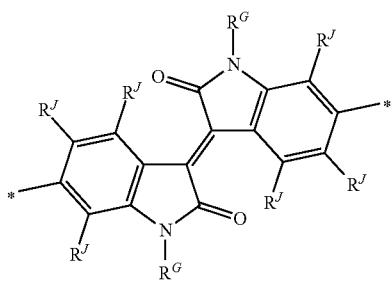
(V<sub>A</sub>-7)

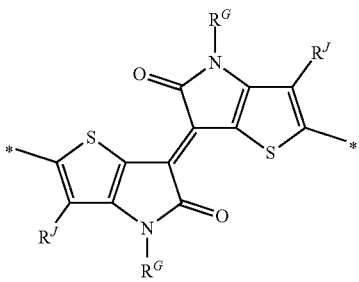
(V<sub>A</sub>-8)

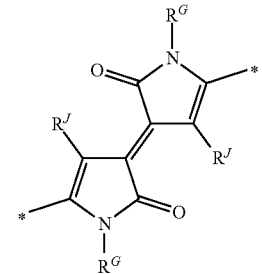
(V<sub>A</sub>-9)

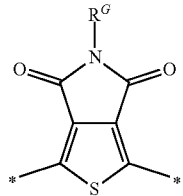
(V<sub>A</sub>-10)

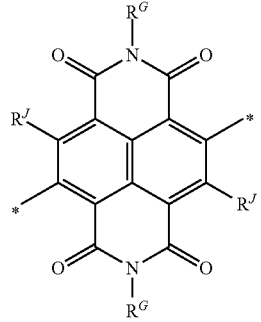
(V<sub>A</sub>-11)

in each formula, R and Z each represent a hydrogen atom, a halogen atom, or an alkyl group, $R^G$ represents an alkyl group, $R^J$ represents a hydrogen atom, an alkyl group, a cyano group, or a halogen atom, and

* represents a bonding site.

[10] The organic semiconductor element according to any one of [7] to [9], in which p3 in Formula (G) is 1.

[11] The organic semiconductor element according to any one of [7] to [10], in which $Ar^1$ and $Ar^2$ each represent a single bond or a divalent group represented by Formula (Ar-1) or (Ar-2), (Ar-1)

(Ar-2)

in each formula, $R^{W1}$ represents an alkyl group, and p1 is an integer of 0 to 2, $L^W$ represents a chalcogen atom, $R^{W2}$ represents an alkyl group, and p2 is an integer of 0 to 4, q1 and q2 each are an integer of 1 to 4, and

* represents a bonding site.

[12] The organic semiconductor element according to any one of [7] to [11], in which Vr in Formula (G) represents a divalent group represented by any one of Formulae ($V_D$-1) to ($V_D$-16).

[13] The organic semiconductor element according to any one of [1] to [12], in which the organic semiconductor element is an organic thin film transistor element.

[14] An organic semiconductor composition comprising: a compound represented by Formula (1), a compound represented by Formula (2), and/or a compound represented by Formula (3), or a polymer having at least one structural unit represented by any one of Formulae (8) to (10); and a solvent, (1)

(2)

(3)

(8)

(9)

(10)

in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, $R^1$ represents a halogen atom or a group represented by Formula (W), and p is an integer of 0 to 2, n represents 1 or 2,

* represents a bonding site,

*-L-T            Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group,

* represents a bonding site,

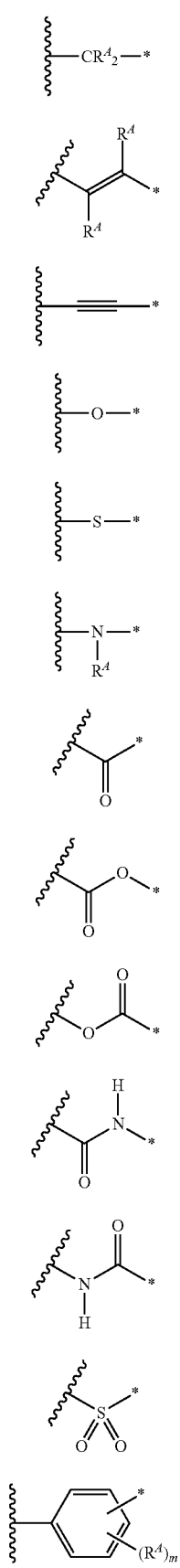
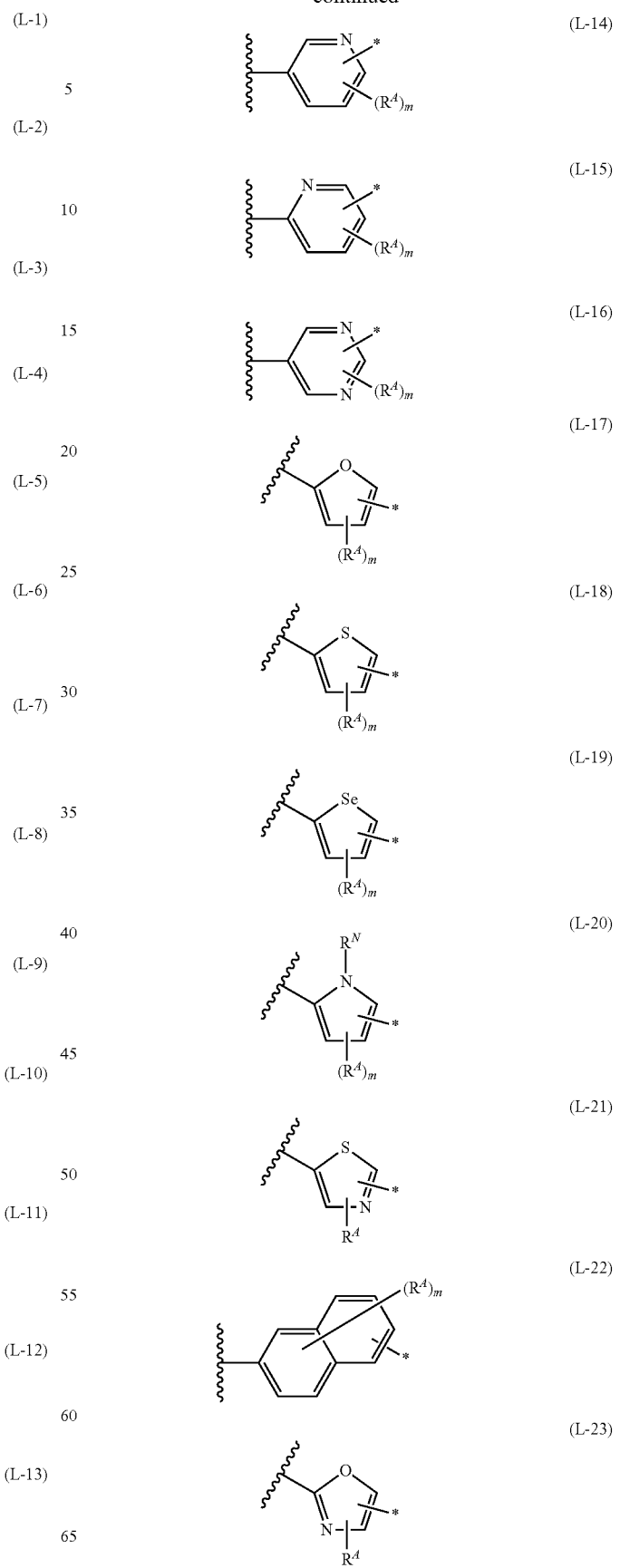

(L-24)

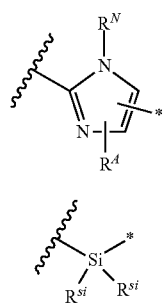

(L-25)

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

[15] The organic semiconductor composition according to [14], comprising: a binder.

[16] A method for manufacturing an organic semiconductor film, comprising: coating a substrate with the organic semiconductor composition according to [14] or [15] to form a coating film, and drying the coating film to obtain an organic semiconductor film.

[17] An organic semiconductor film comprising: a compound represented by Formula (1), a compound represented by Formula (2), and/or a compound represented by Formula (3), or a polymer having at least one structural unit represented by any one of Formulae (8) to (10),

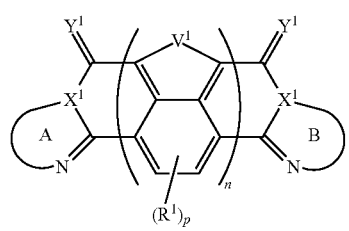

(1)

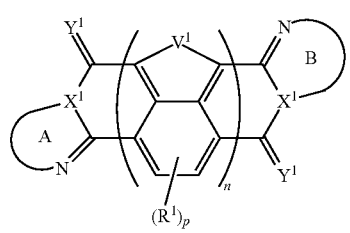

(2)

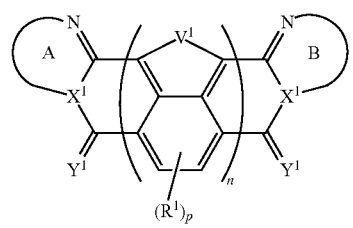

(3)

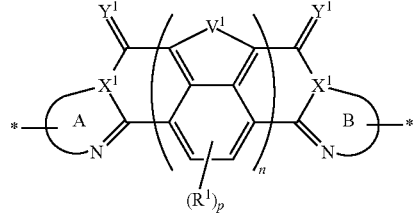

(8)

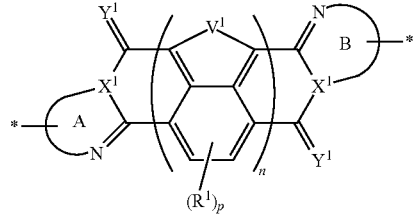

(9)

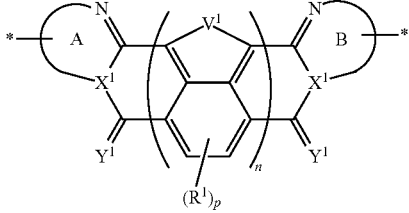

(10)

in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, $R^1$ represents a halogen atom or a group represented by Formula (W), and p is an integer of 0 to 2, n represents 1 or 2,

* represents a bonding site.

*-L-T        Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group,

* represents a bonding site,

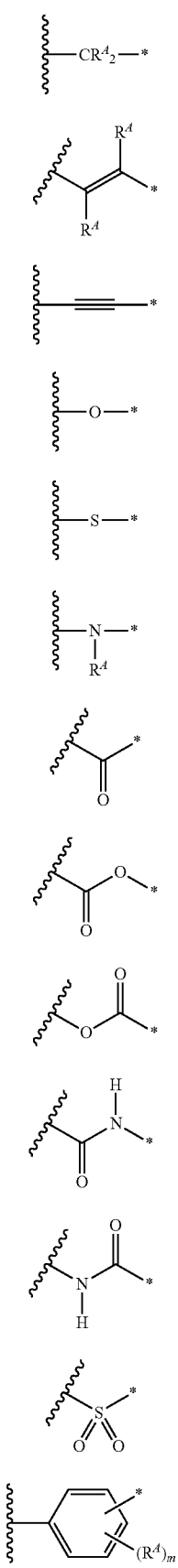
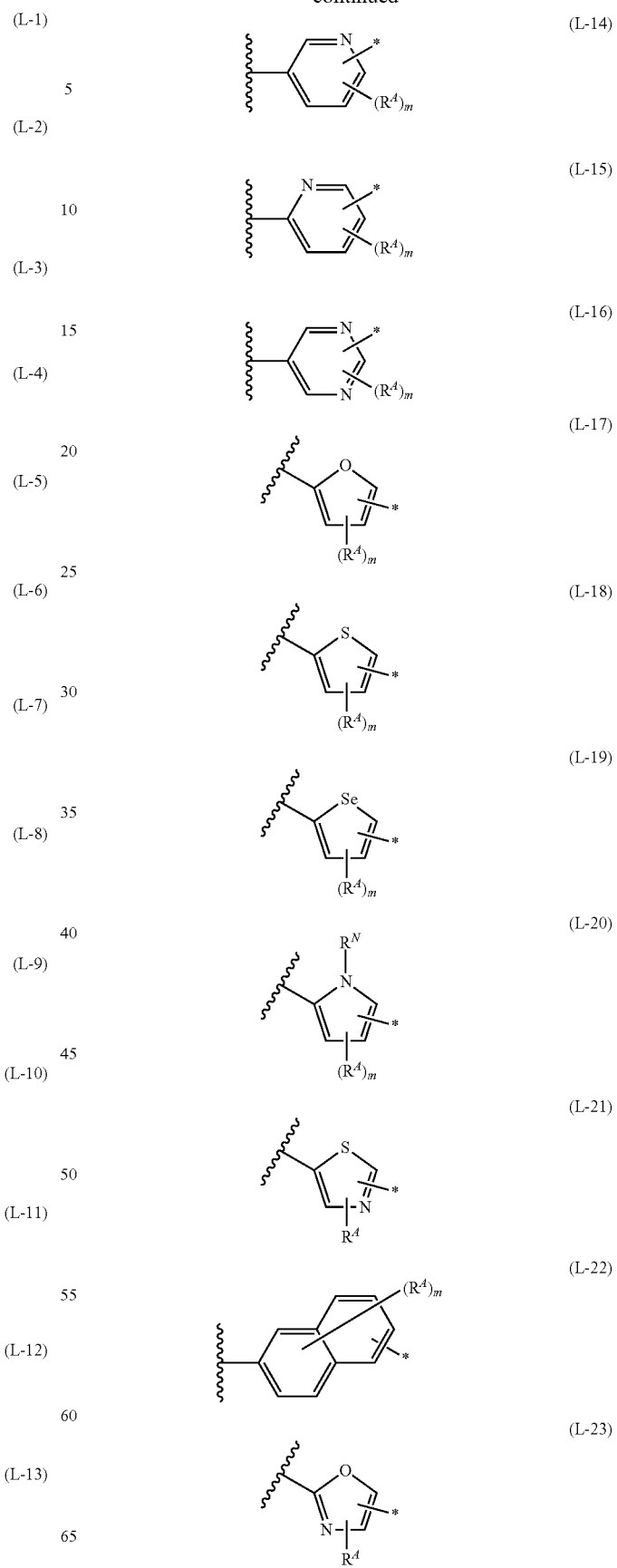

-continued

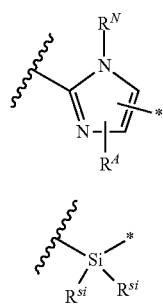
(L-24)

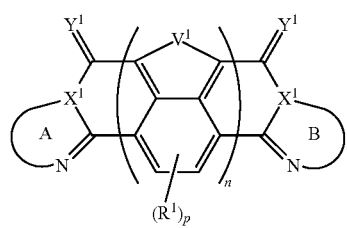
(L-25)

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

[18] A compound represented by any one of Formulae (1) to (3) or a polymer having at least one structural unit represented by any one of Formulae (8) to (10),

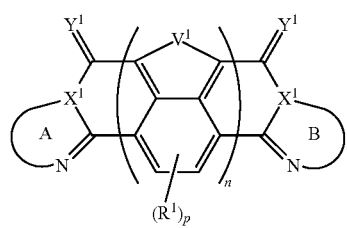
(1)

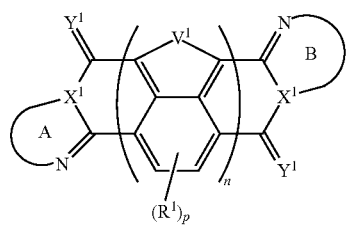
(2)

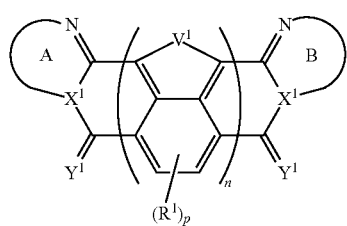
(3)

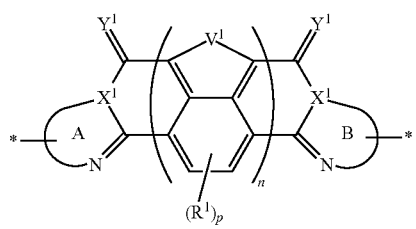
(8)

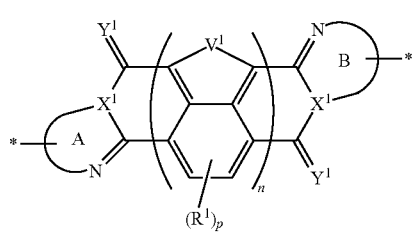
(9)

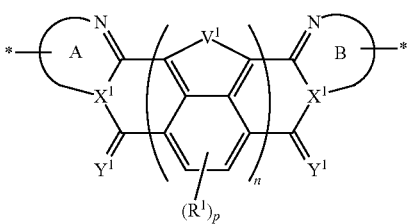
(10)

in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, $R^1$ represents a halogen atom or a group represented by Formula (W), and p is an integer of 0 to 2, n represents 1 or 2,

* represents a bonding site,

*-L-T     Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group,

* represents a bonding site,

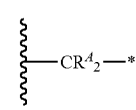
(L-1)

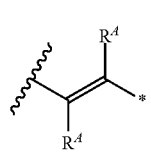
(L-2)

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

In the organic semiconductor element according to the embodiment of the present invention, desired semiconductor characteristics are exhibited, and semiconductor characteristics are hardly decreased even in a case of being exposed to a high temperature environment. In a case where the organic semiconductor film according to the embodiment of the present invention is used as an organic semiconductor layer in an organic semiconductor element, it is possible to cause the obtained organic semiconductor device to exhibit desired semiconductor characteristics and to have characteristics in which the semiconductor characteristics hardly decrease even in a case of being exposed to a high temperature environment. By the method of manufacturing the organic semiconductor film of according to the embodiment of the present invention, it is possible to obtain an organic semiconductor film having the excellent characteristics. The compound, the polymer, and the organic semiconductor composition according to the embodiment of the present invention are appropriate as constituent materials of the organic semiconductor film.

DESCRIPTION OF THE PREFERRED EMBODIMENTS

Figure 1:
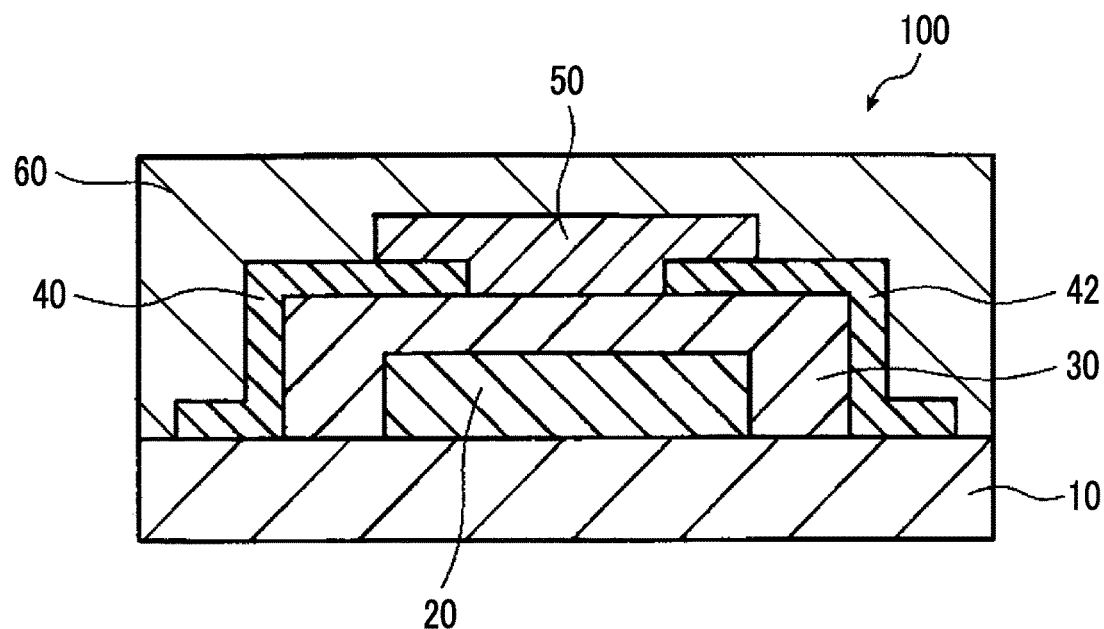
FIG. 1 is a cross-sectional schematic view illustrating a bottom gate-bottom contact-type organic thin film transistor element which is an example of a semiconductor element according to the embodiment of the present invention.

In the present specification, the numerical range expressed by using "to" means a range including numerical values described before and after "to" as a lower limit value and an upper limit value.

In the present specification, the expression of a compound includes the compound itself, a salt thereof, and an ion thereof. A portion of the structure may be changed without deteriorating the desired effect.

A compound which is not explicitly described as substituted or unsubstituted includes those having a random substituent without deteriorating the desired effect. The same is also applied to a substituent, a linking group, a ring structure, and the like (hereinafter, referred to as a substituent and the like).

In the present specification, in a case where there are a plurality of substituents or the like represented by a specific symbol, or in a case where a plurality of substituents and the like are simultaneously defined, unless described otherwise, respective substituents and the like may be identical to or different from each other. The same is also applied to the definition of the number of substituents or the like. In a case where a plurality of substituents and the like are near (particularly, adjacent to each other), unless described otherwise, the substituents and the like may be connected to each other to form a ring.

In the present specification, in a case where a plurality of repeating units represented by the same chemical structure in the polymer are present, the respective repeating units present in the polymer may be identical to or different from each other. The same applies to each group forming the repeating unit.

The number of carbon atoms of the group is limited, the number of the carbon atoms of the group means the total number of carbon atoms including the substituent, unless described otherwise.

In the present invention, in the case where the group can form an acyclic skeleton and a cyclic skeleton, unless described otherwise, the group includes an acyclic skeleton group and a cyclic skeleton group. For example, the alkyl group includes a straight chain alkyl group, a branched alkyl group, and a cyclic (cyclo) alkyl group. In a case where the group can form a cyclic skeleton, the lower limit of the number of atoms of the group forming the cyclic skeleton is 3 or more and preferably 5 or more, regardless of the lower limit of the number of atoms specifically described for this group.

The preferable embodiment of the present invention is described below.

[Organic Semiconductor Element]

In the organic semiconductor element according to the embodiment of the present invention, the organic semiconductor layer is formed by using a compound having a specific structure and a polymer having a specific structure.

The organic semiconductor element according to the embodiment of the present invention is not particularly limited, but is preferably used as a non-luminescent organic semiconductor device. The non-luminescent organic semiconductor device may be any device that is not intended to emit light, and examples thereof include an organic thin film transistor element that controls the amount of current or the amount of voltage, an organic photoelectric conversion element that converts light energy into electric power (such as an individual imaging device for light sensors or a solar cell for energy conversion), an organic thermoelectric conversion element for converting thermal energy into electric power, a gas sensor, an organic rectifying element, an organic inverter, and an information recording element. The non-luminous organic semiconductor device preferably causes the organic semiconductor film to function as an electronic element.

As a representative example of the organic semiconductor element, an organic thin film transistor element is described. An aspect in which the compound having a specific structure and a polymer having a specific structure constitute the organic semiconductor layer of the organic thin film transistor element is described, but the present invention is not limited to the aspect. That is, all of the organic semiconductor element in an aspect in which the organic semiconductor layer contains the compound having a specific structure and the polymer having a specific structure are included in the organic semiconductor element according to the embodiment of the present invention. The organic semiconductor layer having various elements can be formed by the method of forming the organic semiconductor layer in the organic thin film transistor element.

In the above description of the organic thin film transistor element, the improvement of carrier mobility is described, but the carrier mobility is basic characteristics of the organic semiconductor. The organic semiconductor having high carrier mobility is not limited to the organic thin film transistor element, and can exhibit desired performances even in a case of being applied to each of the organic semiconductor elements.

<Organic Thin Film Transistor Element>

The organic thin film transistor element (hereinafter, also referred to as an organic TFT element) according to the embodiment of the present invention has an organic semiconductor film (hereinafter, also referred to as an organic semiconductor layer or a semiconductor active layer), and also has a source electrode, a drain electrode, and a gate electrode.

The organic TFT element according to the embodiment of the present invention includes a gate electrode, an organic semiconductor layer, a gate insulating layer provided between the gate electrode and the organic semiconductor layer, and a source electrode and a drain electrode that are provided in contact with the organic semiconductor layer and are linked to each other via the organic semiconductor layer, on the substrate. In this organic TFT element, the organic semiconductor layer and the gate insulating layer are provided to be adjacent to each other.

The structure of the organic thin film transistor element according to the embodiment of the present invention is not particularly limited, as long as the above respective layers are provided. For example, the organic TFT may have any structures of a bottom contact type (a bottom gate-bottom contact type and a top gate-bottom contact type) or a top contact type (a bottom gate-top contact-type and a top gate-top contact type). The organic thin film transistor element according to the present embodiment of the present invention is more preferably a bottom gate-bottom contact type or a bottom gate-top contact type (these are collectively referred to as a bottom gate type).

Hereinafter, an example of the organic TFT element according to the embodiment of the present invention is described with reference to the drawings.

—Bottom Gate-Bottom Contact-Type Organic Thin Film Transistor Element—

FIG. 1 is a cross-sectional schematic view of the bottom gate-bottom contact-type organic TFT element 100 which is an example of the semiconductor element of the present invention.

As illustrated in FIG. 1, the organic TFT element 100 has a substrate (base material) 10, a gate electrode 20, a gate insulating film 30, a source electrode 40, a drain electrode 42, an organic semiconductor film 50, and a sealing layer 60, in this order.

Hereinafter, a substrate (base material), a gate electrode, a gate insulating film, a source electrode, a drain electrode, an organic semiconductor film, a sealing layer, and a manufacturing method thereof are described above.

(Substrate) The substrate achieves a role of supporting a gate electrode, a source electrode, a drain electrode, and the like described below.

The types of the substrate are not particularly limited, and examples thereof include a plastic substrate, a silicon substrate, a glass substrate, or a ceramic substrate. Among these, in view of applicability to each device and costs, a glass substrate or a plastic substrate is preferable.

The thickness of the substrate is not particularly limited, and examples thereof is preferably 10 mm or less, more preferably 2 mm or less, and particularly preferably 1.5 mm or less. Meanwhile, the thickness is preferably 0.01 mm or more and more preferably 0.05 mm or more.

(Gate Electrode)

As the gate electrode, a well-known electrode that is used as a gate electrode of an organic TFT element may be used without particular limitation.

A material (electrode material) for forming the gate electrode is not particularly limited, and examples thereof include metal such as gold, silver, aluminum, copper, chromium, nickel, cobalt, titanium, platinum, magnesium, calcium, barium, and sodium, conductive oxide such as $InO_2$, $SnO_2$ and indium tin oxide (ITO) a conductive polymer such as polyaniline, polypyrrole, polythiophene, polyacetylene, and polydiacetylene, semiconductor such as silicon, germanium, and gallium arsenide, and a carbon material such as fullerene, carbon nanotube, and graphite. Among these, the above metal is preferable, and silver or aluminum is more preferable.

The thickness of the gate electrode is not particularly limited, but is preferably 20 to 200 nm.

The gate electrode may function as the substrate, and in this case, the above substrate may not be provided.

The method of forming the gate electrode is not particularly limited, and examples thereof include a method of performing vacuum deposition (hereinafter, simply referred to as vapor deposition) or sputtering on the electrode material on the substrate and a method of applying or printing an electrode forming composition that contains the electrode material.

In the case of patterning the electrode, examples of the patterning method include a printing method such as inkjet printing, screen printing, offset printing, or toppan printing (flexographic printing), a photolithography method, and a mask vapor deposition method.

(Gate Insulating Layer)

The gate insulating layer is not particularly limited, as long as the gate insulating layer is a layer having insulating properties, and may be a single layer or multiple layers.

The gate insulating layer is preferably formed of insulating materials, and examples of the insulating materials preferably include an organic polymer or inorganic oxide.

The organic polymer, the inorganic oxide, and the like are not particularly limited, as long as the organic polymer, the inorganic oxide, and the like have insulating properties. It is preferable to form a thin film, for example, a thin film having a thickness of 1 μm or less.

The organic polymer and the inorganic oxide may be used singly, two or more kinds thereof may be used in combination, or an organic polymer and inorganic oxide may be used in combination.

The organic polymer is not particularly limited, and examples thereof include polyvinyl phenol, polystyrene (PS), poly(meth)acrylate represented by polymethyl methacrylate, polyvinyl alcohol, polyvinyl chloride (PVC), polyvinylidene fluoride (PVDF), polytetrafluoroethylene (PTFE), a cyclic fluoroalkyl polymer represented by CYTOP (registered trademark), polycycloolefin, polyester, polyethersulfone, polyether ketone, polyimide, an epoxy resin, polyorganosiloxane represented by polydimethylsiloxane (PDMS), polysilsesquioxane, or butadiene rubber. In addition to the above, examples thereof include a thermosetting resin such as a phenol resin, a novolak resin, a cinnamate resin, an acrylic resin, or a polyparaxylylene resin.

The organic polymer may be used in combination with a compound having a reactive substituent such as an alkoxysilyl group, a vinyl group, an acryloyloxy group, an epoxy group, or a methylol group.

In a case where the gate insulating layer is formed with an organic polymer, it is preferable to crosslinking and hardening the organic polymer for the purpose of increasing solvent resistance or insulation resistance of the gate insulating layer. The crosslinking is preferably performed by using light, heat, or both, so as to generate acid or radical.

In a case where crosslinking is performed with a radical, as a radical generating agent that generates radicals by light or heat, for example, thermal polymerization initiators (H1) and photopolymerization initiators (H2) disclosed in paragraphs [0182] to [0186] of JP2013-214649A, photoradical generating agents disclosed in paragraphs [0046] to [0051] of JP2011-186069A, or photoradical polymerization initiators disclosed in paragraphs [0042] to [0056] of JP2010-285518A can be suitably used, and the contents thereof are preferably incorporated in the present specification.

The "compound (G) having number-average molecular weight (Mn) of 140 to 5,000, having crosslinking functional groups, and not having a fluorine atom" disclosed in paragraphs [0167] to [0177] of JP2013-214649A is preferably used, and the contents thereof are preferably incorporated to this specification.

In the case of crosslinking with an acid, examples of the photoacid generator that generates acid by light include photo cationic polymerization initiators disclosed in paragraphs [0033] to [0034] of JP2010-285518A, acid generators disclosed in paragraphs [0120] to [0136]of JP2012-163946A, particularly sulfonium salts, iodonium salts, and the like may be preferably used, and it is preferable that the contents thereof are incorporated into the present specification.

As a thermal acid generator (catalyst) that generates acid by heat, for example, thermal cation polymerization initiators and particularly onium salts disclosed in paragraphs [0035] to [0038] of JP2010-285518A, catalysts disclosed in paragraphs [0034] to [0035] of JP2005-354012A, particularly, sulfonic acids and sulfonic acid amine salts preferably can be used, and the contents thereof are preferably incorporated to this specification.

Crosslinking agents, particularly difunctional or higher epoxy compounds and oxetane compounds disclosed in paragraphs [0032] to [0033] of JP2005-354012A, crosslinking agents, particularly compounds, each of which has two or more crosslinking groups and in which at least one of these crosslinking groups is a methylol group or a NH group, disclosed in paragraphs [0046] to [0062] of JP2006-303465A, and compounds, each of which has two or more of hydroxymethyl groups or alkoxymethyl groups in a molecule, disclosed in paragraphs [0137] to [0145] of JP2012-163946A, are preferably used, and the contents thereof are preferably incorporated in this specification.

The method forming a gate insulating layer with an organic polymer is not particularly limited, and examples thereof include a method of applying the coating solution containing the organic polymer, and curing the coating solution, if necessary.

A solvent used in the coating solution is not particularly limited, as long as the solvent does not dissolve but can disperse the organic polymer, and can be appropriately selected from solvents generally used according to the kinds of the organic polymer, or the like.

The coating method is not particularly limited, and examples thereof include the above printing methods.

Among these, a wet coating method such as a micro gravure coating method, a dip coating method, screen coating printing, a die coating method, or a spin coating method is preferable.

The coating conditions are not particularly limited, and can be appropriately set.

The curing method and conditions are not particularly limited, as long as the organic polymer can be crosslinked by the method and conditions, and can be appropriately set, for example, according to the crosslinking method (radical or acid), and also the kinds of a photoacid generator or thermal acid generator used.

The inorganic oxide is not particularly limited, and examples thereof include oxide such as silicon oxide, silicon nitride ($SiN_Y$), hafnium oxide, titanium oxide, tantalum oxide, aluminum oxide, niobium oxide, zirconium oxide, copper oxide, and nickel oxide, a compound having a perovskite structure such as $SrTiO_3$, $CaTiO_3$, $BaTiO_3$, $MgTiO_3$, and $SrNb_2O_6$, and composite oxide or mixture of these.

Here, in addition to silicon oxide ($SiO_X$), the silicon oxide includes Boron Phosphorus Silicon Glass (BPSG), Phosphorus Silicon Glass (PSG), borosilicate glass (BSG), arsenic silicate glass (AsSG), lead silicate glass (PbSG), silicon oxynitride (SiON), spin-on-glass (SOG), a low dielectric constant $SiO_2$-based material (for example, polyaryl ether, a cycloperfluorocarbon polymer, benzocyclobutene, a cyclic fluororesin, polytetrafluoroethylene, fluoroaryl ether, fluorinated polyimide, amorphous carbon, organic SOG).

The method of forming a gate insulating layer with inorganic oxide is not particularly limited, and a vacuum film formation method such as a vacuum evaporation method, a sputtering method, an ion plating method, or a chemical vapor deposition (CVD) method can be used. Plasma using any gas, an ion gun, a radical gun, or the like may be also used during film formation.

A gate insulating layer can be formed by causing a precursor corresponding to each of the metal oxide, specifically, metal halides such as chlorides and bromides, metal alkoxide, and metal hydroxide, to react with an acid such as hydrochloric acid, sulfuric acid, and nitric acid and a base such as sodium hydroxide or potassium hydroxide in alcohol or water so as to perform hydrolysis. In a case where such a solution-based process is used, a wet-coating method can be used.

In a case where the gate insulating layer is formed with inorganic oxide, in addition to the above method, it is possible to use a method of combining any one of a lift-off method, a sol-gel method, an electrodeposition method, and a shadow mask method, with a patterning method, if necessary.

A surface treatment such as a corona treatment, a plasma treatment, an ultraviolet (UV)/ozone treatment may be performed on the gate insulating layer. In this case, it is preferable that the surface roughness is not roughened by each treatment. For example, it is preferable that arithmetic mean roughness Ra or root mean square roughness $R_q$ (all are JIS B0601: 2013) of the gate insulating layer surface after the treatment is 0.5 nm or less.

The thickness of the gate insulating film is not particularly limited but is preferably 100 to 1,000 nm.

(Source Electrode and Drain Electrode)

In the organic TFT element according to the embodiment of the present invention, the source electrode is an electrode in which a current flows from the outside through wire. The drain electrode is an electrode in which a current is sent to the outside through wire.

As a material for forming the source electrode and the drain electrode, the same materials as the electrode material for forming the above gate electrode may be used. Among these, metal is preferable, and silver is more preferable.

The thicknesses of the source electrode and the drain electrode are not particularly limited, but each are preferably 1 nm or more and particularly preferably 10 nm or more. The thickness is preferably 500 nm or less and particularly preferably 300 nm or less.

The distance (gate length) between the source electrode and the drain electrode may be appropriately determined, but for example, the distance is preferably 200 μm or less and particularly preferably 100 μm or less. The gate width may be appropriately determined, but for example, the gate width is preferably 5,000 m or less and particularly preferably 1,000 μm or less.

The method of forming the source electrode and the drain electrode is not particularly limited, and examples thereof include a method of performing vacuum deposition or sputtering on the electrode material on the substrate on which the gate electrode and the gate insulating film are formed or a method of applying or printing the electrode forming composition. In the case of patterning, the patterning method is the same as the method of the gate electrode described above.

(Organic Semiconductor Layer (Film))

According to an embodiment (hereinafter, also referred to as a "first embodiment") of the organic TFT element, the organic semiconductor layer contains a compound represented by Formula (1), a compound represented by Formula (2), and/or a compound represented by Formula (3) (that is, contains at least one of the compound represented by Formula (1), the compound represented by Formula (2), or the compound represented by Formula (3)). The compound represented by Formula (1) or (3) is referred to as a cis isomer, and the compound represented by Formula (2) is referred to as a trans isomer.

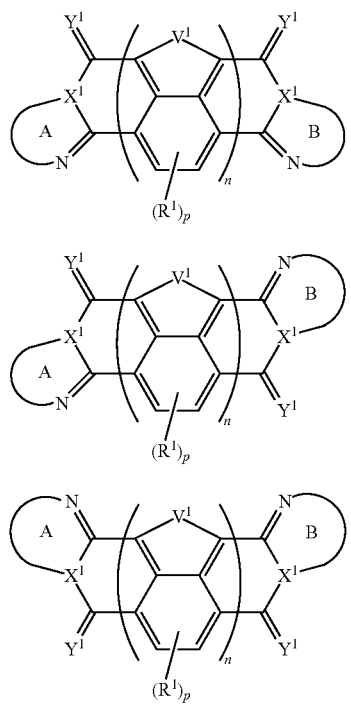

In Formulae (1) to (3), $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom. The fused ring is preferably a two-ring structure or a three-ring structure, more preferably a two-ring structure. $R^a$ represents a hydrogen atom or a substituent. $X^1$ is preferably a nitrogen atom.

$Y^1$ represents an oxygen atom, a sulfur atom, $CR^b{}_2$, or $NR^c$. $R^b$ and $R^c$ each represent a hydrogen atom or a substituent. $Y^1$ is preferably an oxygen atom or a sulfur atom and more preferably an oxygen atom.

$V^1$ represents $NR^d$, an oxygen atom, a sulfur atom, or a selenium atom. $V^1$ is preferably a sulfur atom or a selenium atom, and more preferably a sulfur atom.

The substituents employed as the $R^a$, $R^b$, $R^c$, and $R^d$ are not particularly limited, and a group represented by Formula (W), and examples thereof a halogen atom (a fluorine atom, a chlorine atom, a bromine atom, and an iodine atom are preferable, a fluorine atom and a chlorine atom are more preferable, and a fluorine atom is particularly preferable). Among these, as the substituents employed as $R^a$, $R^b$, $R^c$, and $R^d$, an alkyl group (an alkyl group having 1 to 35 carbon atoms is preferable, and an alkyl group having 1 to 25 carbon atoms is more preferable), an alkenylene group (the number of carbon atoms thereof is preferably 2 to 30), an alkynyl group (the number of carbon atoms thereof is preferably 2 to 30), an aromatic hydrocarbon group (the number of carbon atoms thereof is preferably 6 to 30), an aromatic heterocyclic ring group (a 5-membered to 7-membered ring is preferable; a ring-constituting atom preferably includes at least one of an oxygen atom, a nitrogen atom, a sulfur atom, or a selenium atom), or a halogen atom (a fluorine atom, a chlorine atom, a bromine atom, or an iodine atom are preferable, a fluorine atom and a chlorine atom are more preferable, and a fluorine atom is particularly preferable.) is preferable.

The above alkyl group, alkenyl group and alkynyl group which can be employed as $R^a$, $R^b$, $R^c$, and $R^d$ may include at least one of —O—, —S—, or —$NR^{X1}$— in the carbon chain or at the terminal of the carbon chain (for example, an aspect in which one —O— is included at a terminal of a carbon chain of the alkyl group). $R^{X1}$ represents a hydrogen atom or a substituent. The number of —O—, —S—, and —$NR^{X1}$— included in the carbon chain or at a terminal of a carbon chain is preferably an integer of 1 to 5, more preferably 1 to 3, and even more preferably 1 in total.

The substituent that can be employed as $R^{X1}$ is not particularly limited, and examples thereof include an alkyl group (preferably an alkyl group having 1 to 10 carbon atoms), a halogen atom (preferably a fluorine atom, a chlorine atom, a bromine atom, or an iodine atom), or an aromatic hydrocarbon group (preferably an aromatic hydrocarbon group having 6 to 20 carbon atoms). $R^{X1}$ is preferably a hydrogen atom or an alkyl group and more preferably an alkyl group.

$R^1$ represents a halogen atom (preferably a fluorine atom, a chlorine atom, a bromine atom, or an iodine atom), or a group represented by Formula (W), and p is an integer of 0 to 2. p is preferably 0 or 2 and more preferably 0.

The group represented by Formula (W) which can be employed as $R^1$ is a group having a structure described below.

*-L-T  Formula (W)

In Formula (W), L is a single bond, or a divalent group represented by any one of Formulae (L-1) to (L-25), or a divalent group formed by bonding two or more divalent groups represented by any of (L-1) to (L-25). The two or more bonded divalent groups may be identical to as or different from each other.

T represents a hydrogen atom, a halogen atom (preferably a fluorine atom, a chlorine atom, a bromine atom, or an iodine atom) or a cyano group.

* represents a bonding site to a benzene ring represented in Formulae (1) to (3).

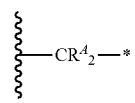
(L-1)

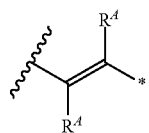
(L-2)

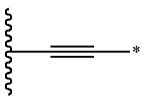
(L-3)

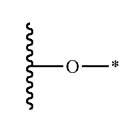
(L-4)

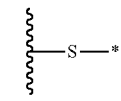
(L-5)

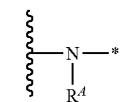
(L-6)

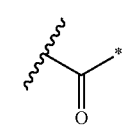
(L-7)

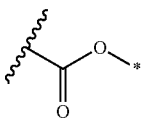
(L-8)

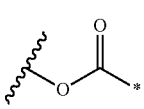
(L-9)

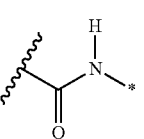
(L-10)

-continued

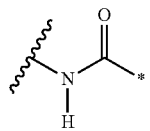
(L-11)

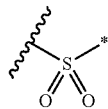
(L-12)

(L-13)

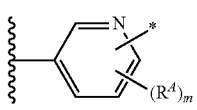
(L-14)

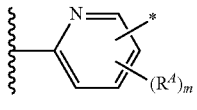
(L-15)

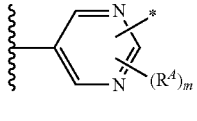
(L-16)

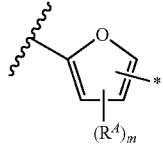
(L-17)

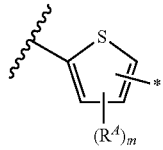
(L-18)

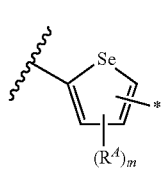
(L-19)

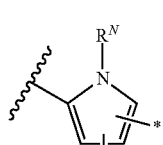
(L-20)

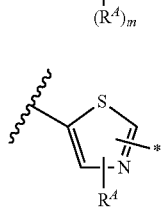
(L-21)

(L-22)
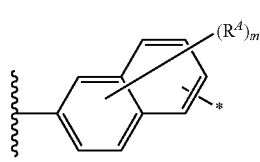

(L-23)
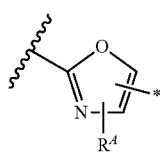

(L-24)
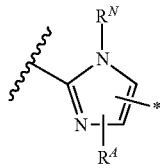

(L-25)
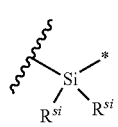

(L-19A)
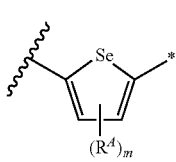

(L-20A)
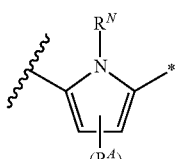

(L-21A)
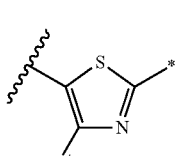

(L-23A)
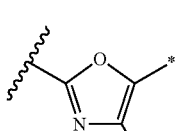

(L-24A)
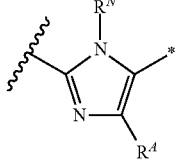

In Formulae (L-1) to (L-25), the wavy line portion represents a bonding site to a ring structure represented by Formulae (1) to (3), or a bonding site to * of a divalent group represented by any one of Formulae (L-1) to (L-25).

* represents a bonding site to T, or a bonding site to a wavy line portion of a divalent group represented by any one of Formulae (L-1) to (L-25).

In Formulae (L-1), (L-2), (L-6), and (L-13) to (L-24), $R^A$ represents a hydrogen atom or a substituent.

In Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6.

In Formulae (L-20) and (L-24), $R^N$ represents a hydrogen atom or a substituent.

In Formula (L-25), $R^{si}$ represents a hydrogen atom, an alkyl group, an alkenyl group, or an alkynyl group.

The divalent groups represented by Formulae (L-17) to (L-21), (L-23), and (L-24) are preferably structures represented by Formulae (L-17A) to (L-21A), (L-23A), and (L-24A), respectively. $R^A$, $R^N$, m, and * in Formula (L-17A) to (L-21A), (L-23A), and (L-24A) are the same as $R^A$, $R^N$, m, and * in Formulae (L-17) to (L-21), (L-23), and (L-24).

(L-17A)
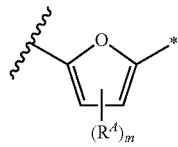

(L-18A)
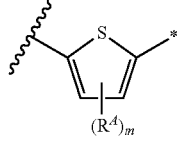

L in Formula (W) is a divalent group selected from Formulae (L-1), (L-2), (L-3), (L-4), (L-13), (L-17), and (L-18), or a group obtained by bonding two or more divalent groups selected from Formulae (L-1), (L-2), (L-3), (L-4), (L-13), (L-17), and (L-18).

The molecular weight of -L- in Formula (W) is preferably 1,000 or less, more preferably 600 or less, and even more preferably 300 or less.

The substituent that may be employed as $R^A$ and $R^N$ is not particularly limited, and, for example, a group selected from an alkyl group, an alkenyl group, an alkynyl group, an aromatic hydrocarbon group, an aromatic heterocyclic group, and a halogen atom is preferable, and preferable aspects thereof are respectively the same as the aspects of the alkyl group, the alkenyl group, the alkynyl group, the aromatic hydrocarbon group, the aromatic heterocyclic group, and the halogen atom that can be employed as $R^a$ to $R^d$.

The preferable aspects of the alkyl group, the alkenyl group, and the alkynyl group that can be employed as $R^{si}$ are respectively the same as the aspects of the alkyl group, the alkenyl group, and the alkynyl group that can be employed as $R^a$ to $R^d$.

The group represented by Formula (W) is preferably an alkyl group, an alkenyl group, or an alkynyl group, the preferable aspects of the alkyl group, the alkenyl group, or the alkynyl group are respectively the same as the aspects of the alkyl group, the alkenyl group, or the alkynyl group that can be employed as $R^a$ to $R^d$.

In Formulae (1) to (3), n is 1 or 2, and is preferably 1.

With respect to the organic TFT element, in a case where the organic semiconductor layer includes a compound represented by Formula (1), a compound represented by Formula (2), and/or a compound represented by Formula (3), both of the desired carrier mobility and heat resistance can be realized. The reason thereof is not clear, but it is thought that the effect largely depends on the action of a mother nucleus (the fused polycyclic structure provided in each formula) of each of the above compounds. That is, since the mother nuclei forms the asymmetric fused ring structure in the minor axis direction, it is assumed that the intermolecular interaction between adjacent mother nuclei increases due to the dipole moment and the overlapping of the orbits increases to improve carrier mobility, and the rate of change in crystal structure is suppressed in a case of heating by increasing the intermolecular interaction between the adjacent mother nuclei to improve the heat resistance.

In Formulae (1) to (3), the rings A and B each are preferably a fused ring structure represented by Formula (4) or (5) and more preferably a fused ring structure represented by Formula (4).

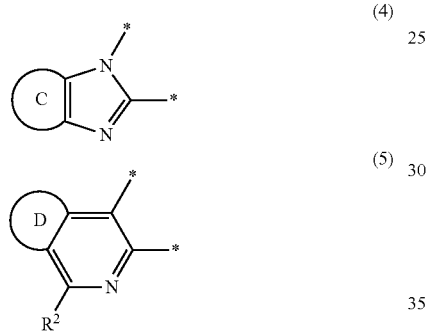

(4)

(5)

In Formulae (4) and (5), rings C and D each represent a 5-membered aromatic ring or a 6-membered aromatic ring, or a fused ring including a 5-membered aromatic ring or a 6-membered aromatic ring. The aspect of the fused ring including a 5-membered aromatic ring or a 6-membered aromatic ring is preferably a two-ring structure. The rings C and D each are preferably a single ring structure.

$R^2$ represents a hydrogen atoms, a halogen atom (preferably a fluorine atom, a chlorine atom, a bromine atom, or an iodine atom), or a group represented by Formula (W).

* represents a bonding site.

The fused ring structure represented by Formula (4) is preferably a fused ring structure represented by Formula (6) or (7) and more preferably a fused ring structure represented by Formula (7).

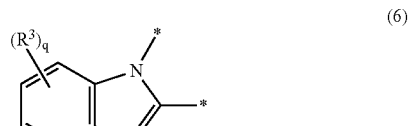

(6)

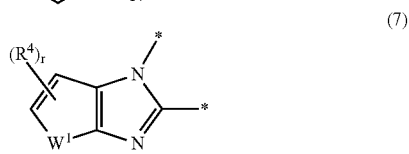

(7)

In Formulae (6) and (7), $R^3$ and $R^4$ each represent a halogen atom (preferably a fluorine atom, a chlorine atom, a bromine atom, or an iodine atom), or a group represented by Formula (W).

q is an integer of 0 to 4, preferably 1 or 2, and more preferably 1. r is an integer of 0 to 2 and preferably 1.

$W^1$ represents a chalcogen atom. $W^1$ is preferably an oxygen atom or a sulfur atom and more preferably a sulfur atom.

* represents a bonding site.

Specific preferable examples of the compound represented by Formulae (1) to (3) are provided below, but the present invention is not limited to these aspects.

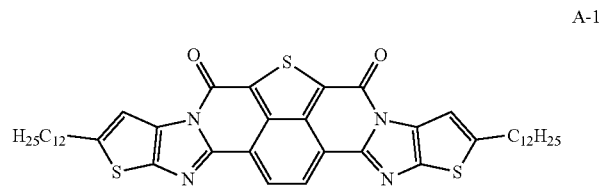

A-1

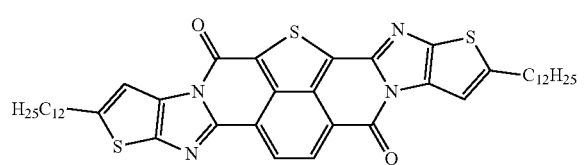

A-2

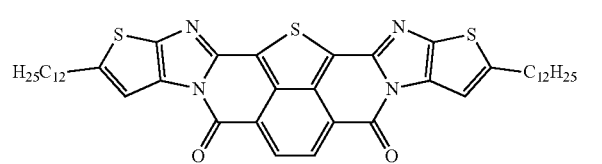

A-3

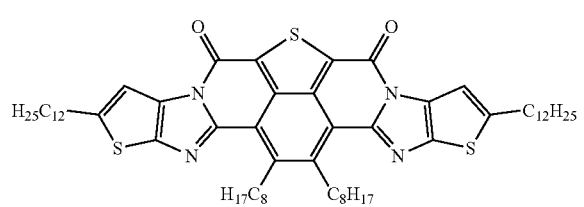

A-4

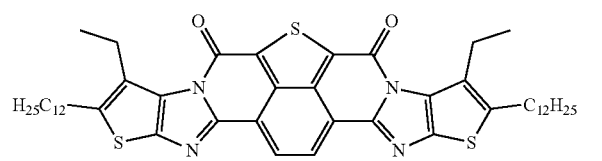

A-5

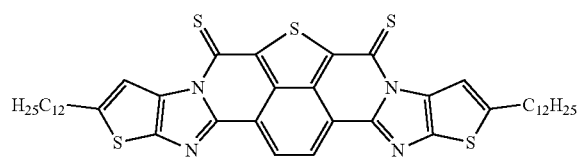

A-6

-continued
A-7
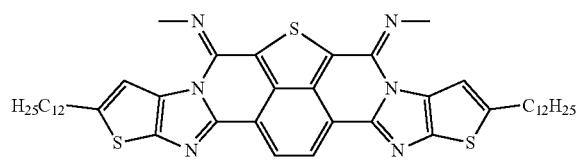
A-8
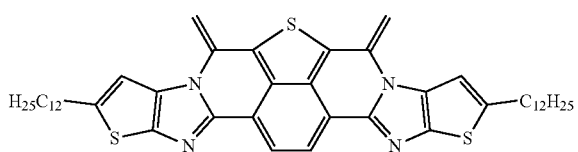
A-9
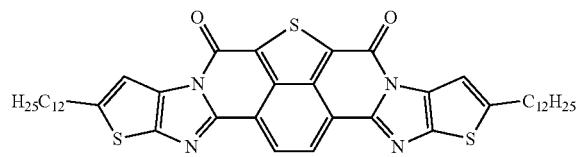
A-10
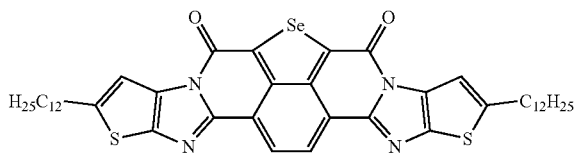
A-11
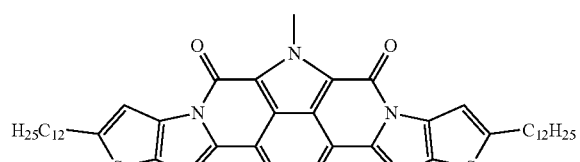
A-12
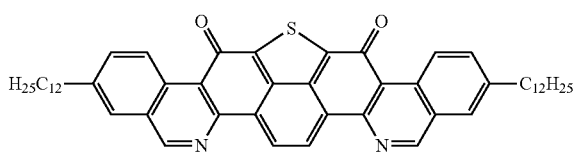
A-13
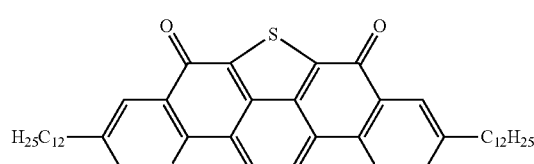
A-14
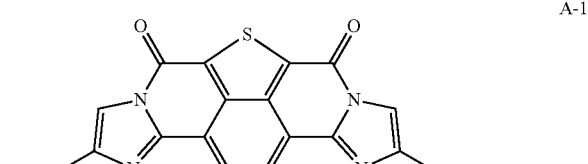
A-15
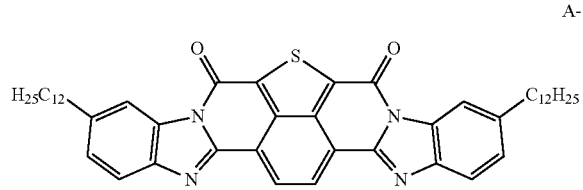
A-16
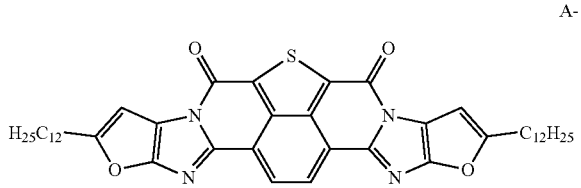
A-17
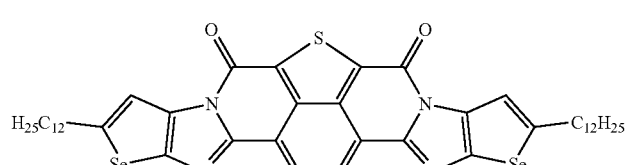
A-18
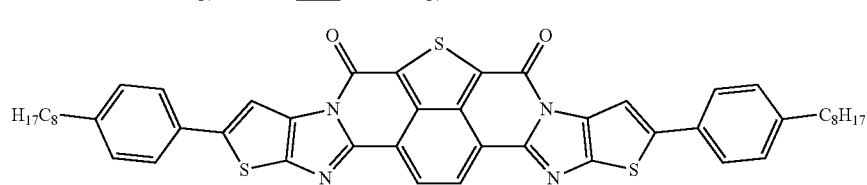
A-19
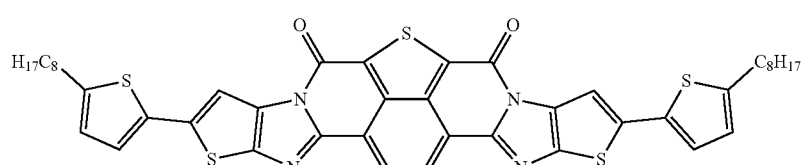
A-20
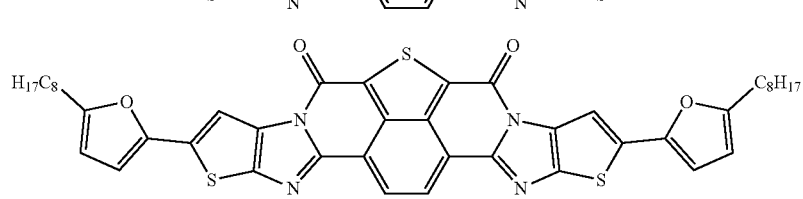

-continued
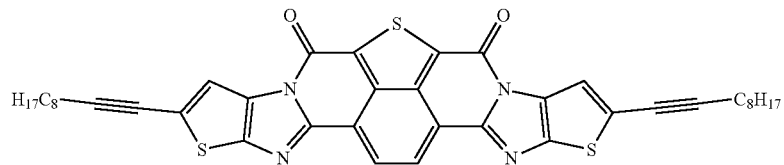
A-21
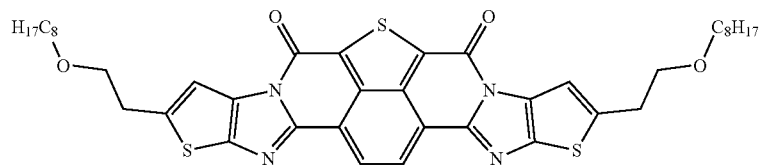
A-22
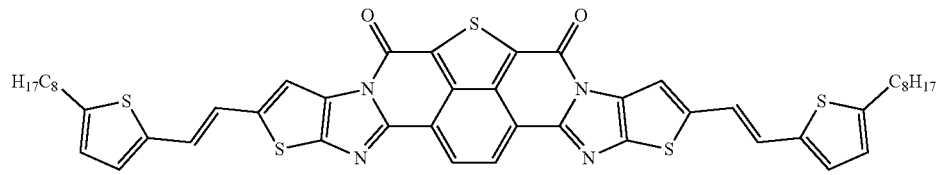
A-23
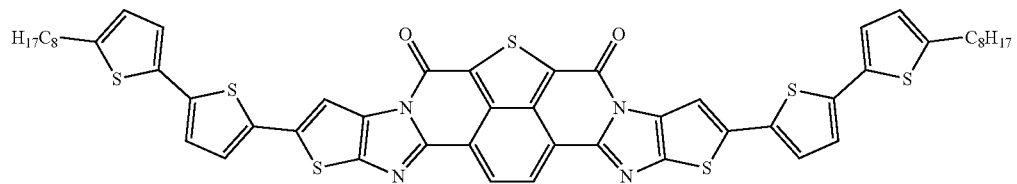
A-24
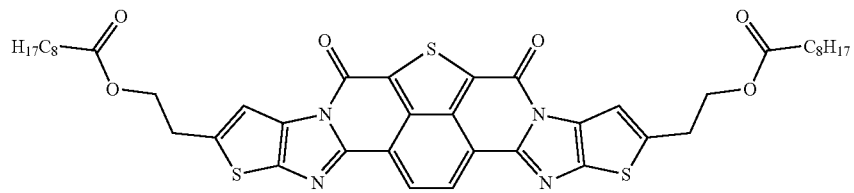
A-25
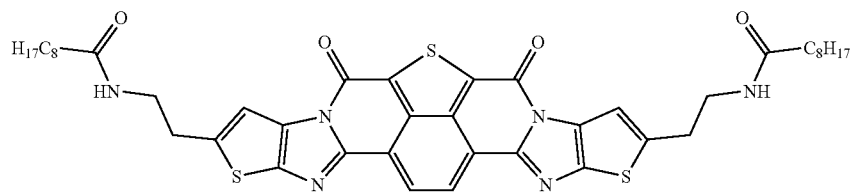
A-26
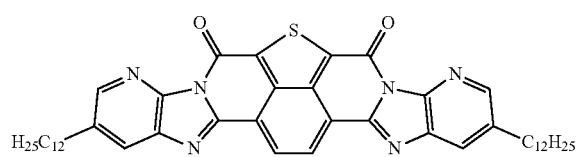
A-27
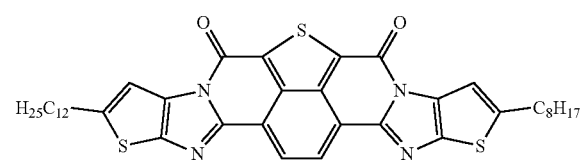
C-1
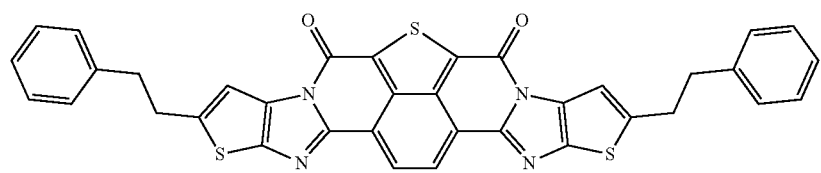
C-2

-continued
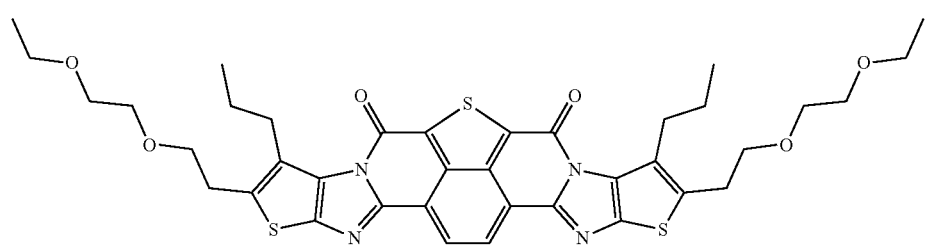
C-3
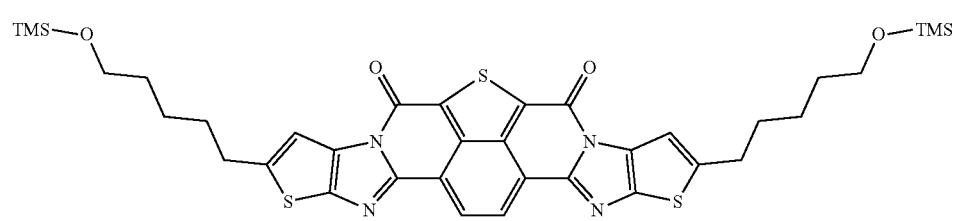
C-4
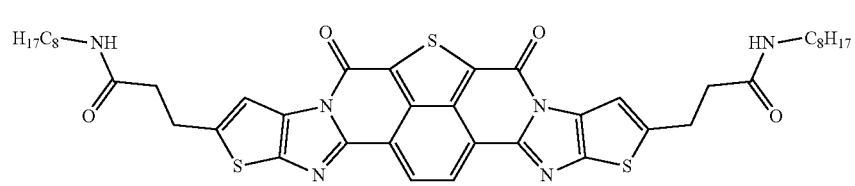
C-5
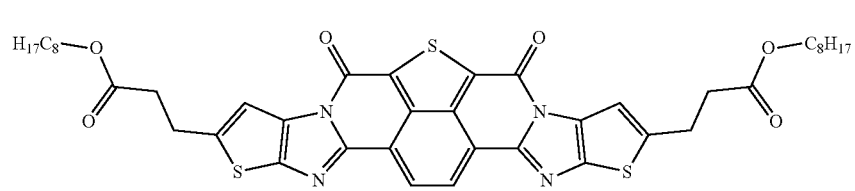
C-6
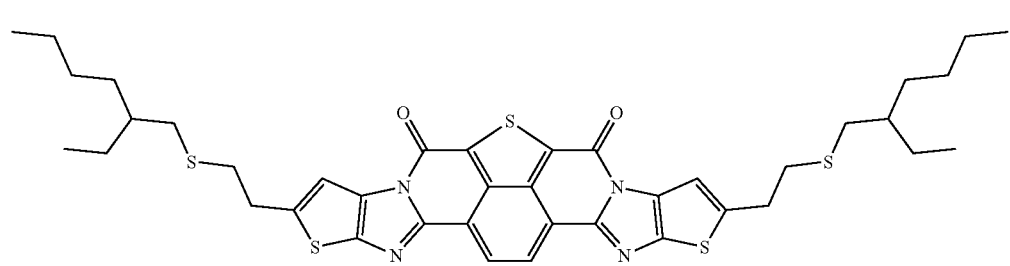
C-7
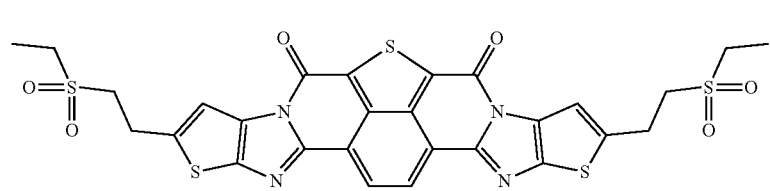
C-8
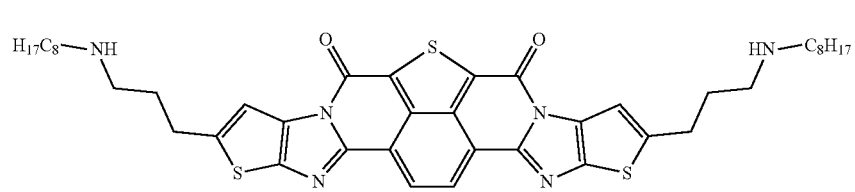
C-9

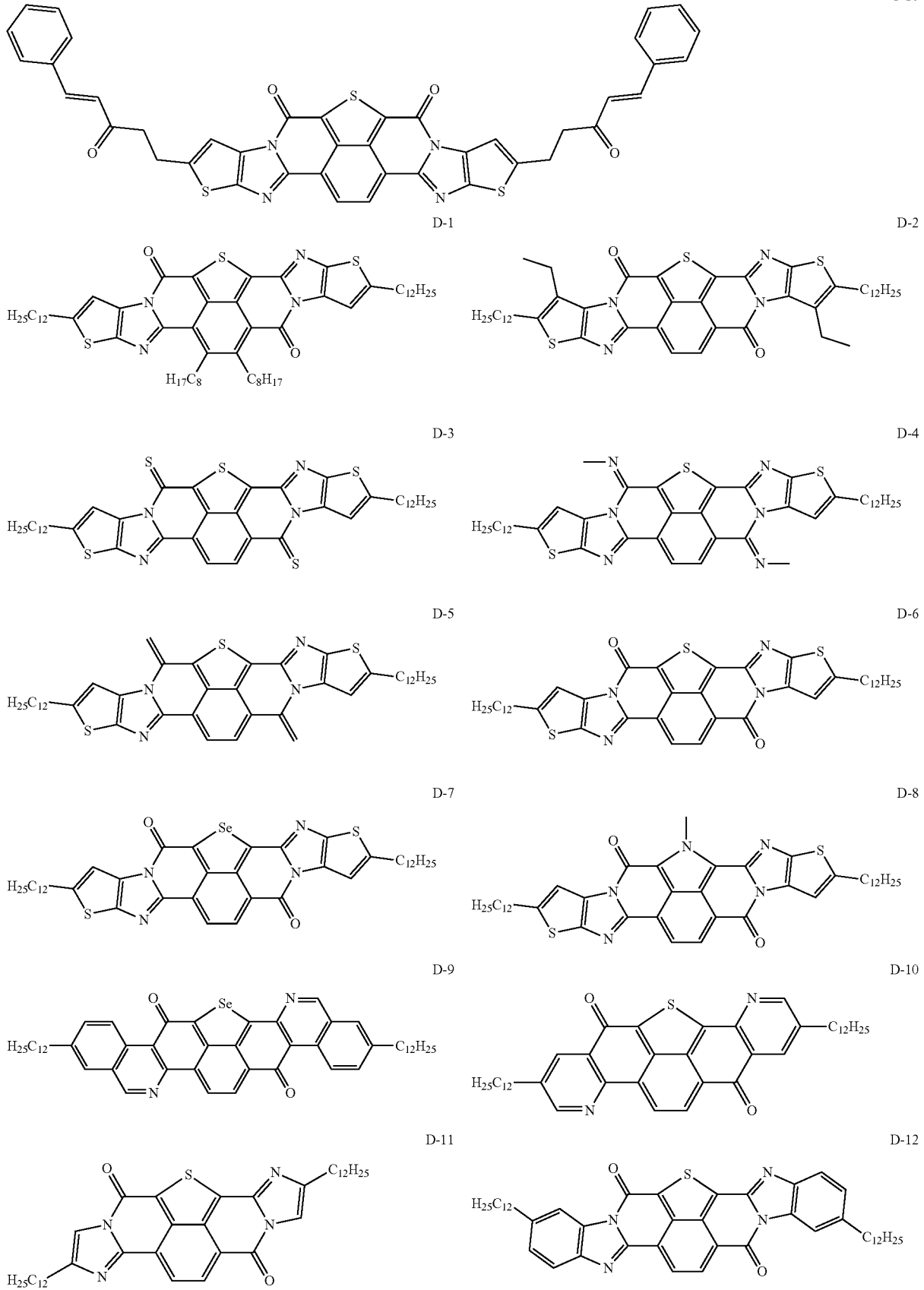

-continued
D-13
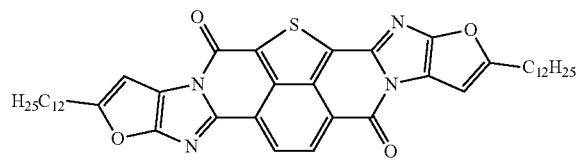
D-14
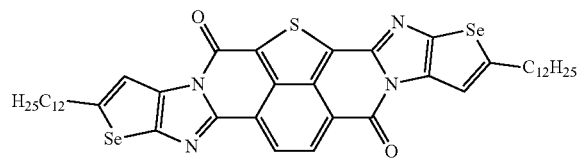
D-15
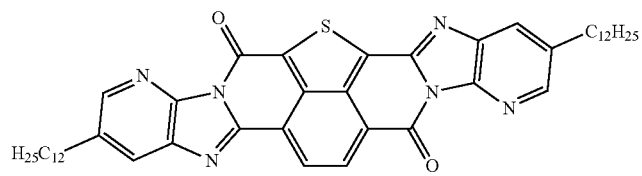
D-16
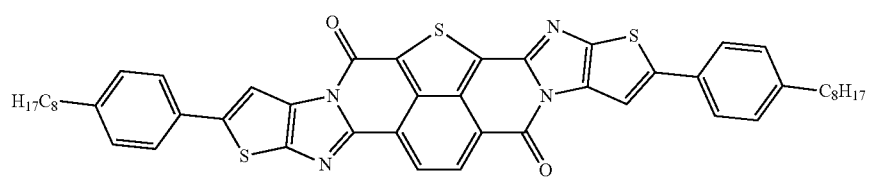
D-17
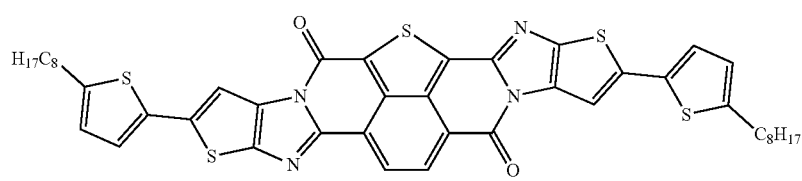
D-18
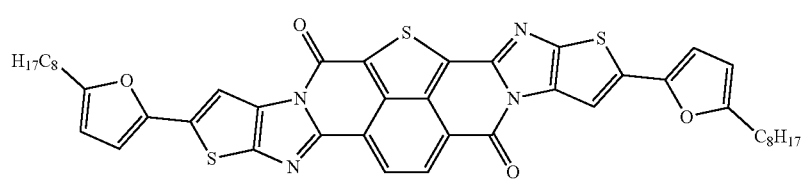
D-19
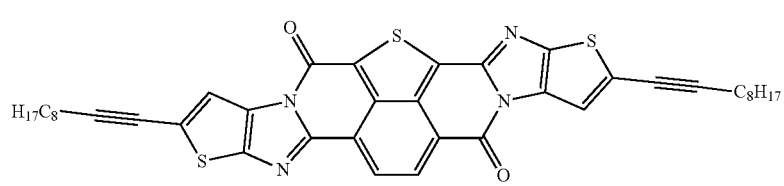
D-20
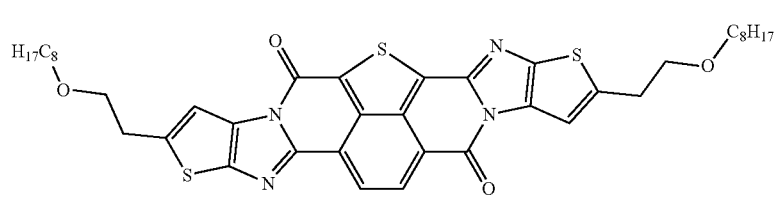
D-21
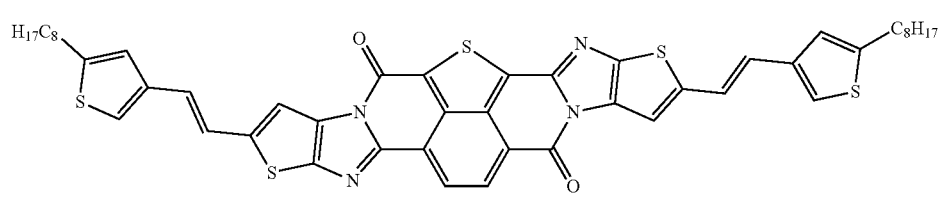

-continued
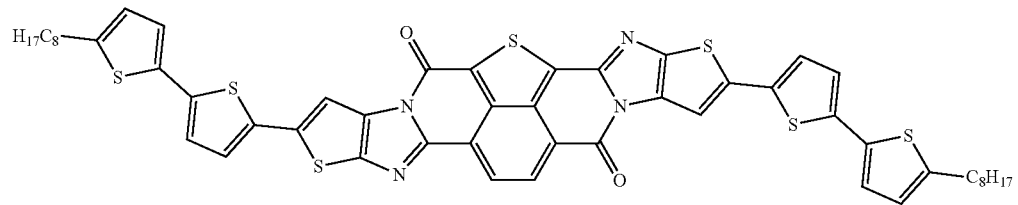
D-22
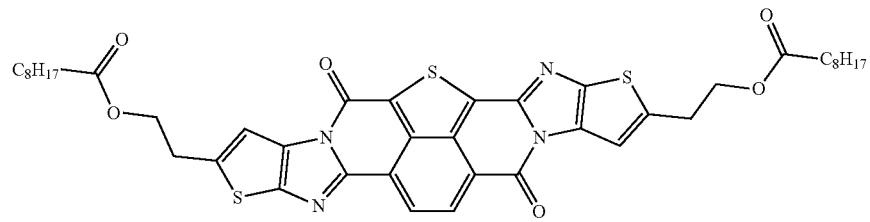
D-23
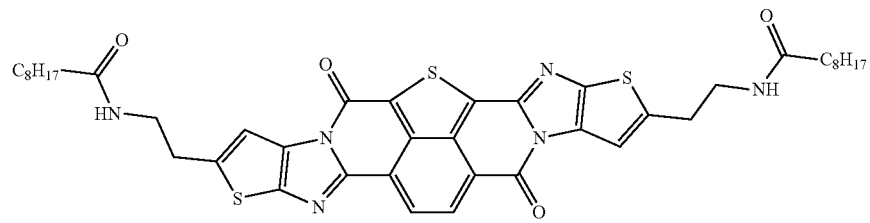
D-24
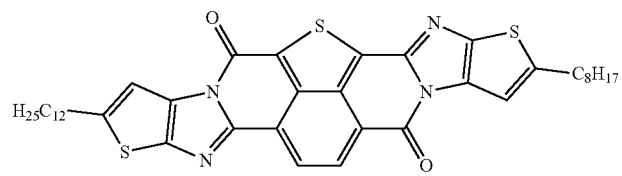
D-25
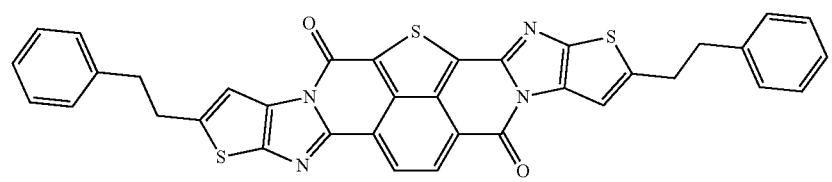
D-26
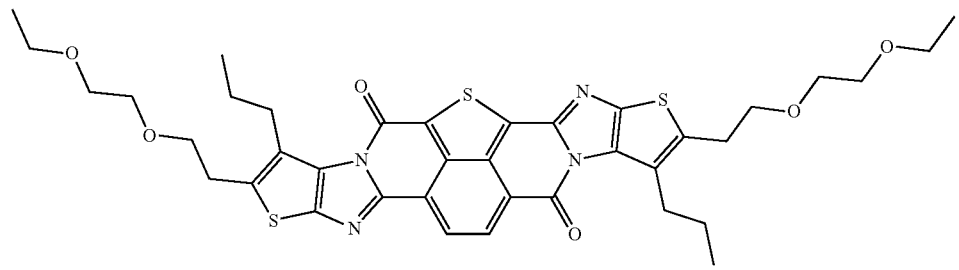
D-27
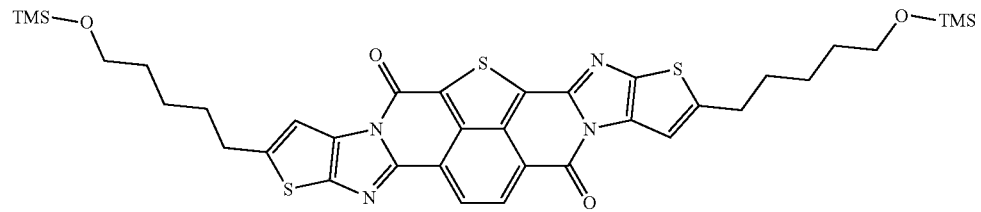
D-28

-continued
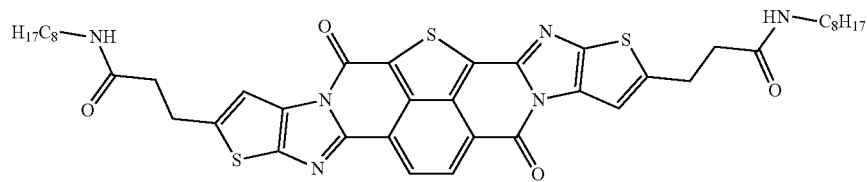
D-29
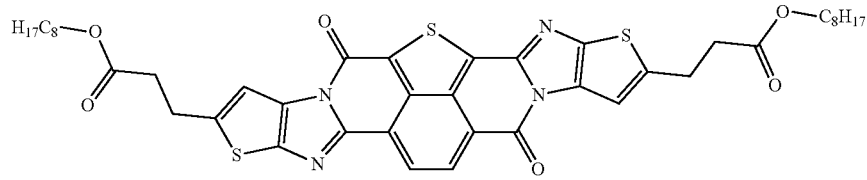
D-30
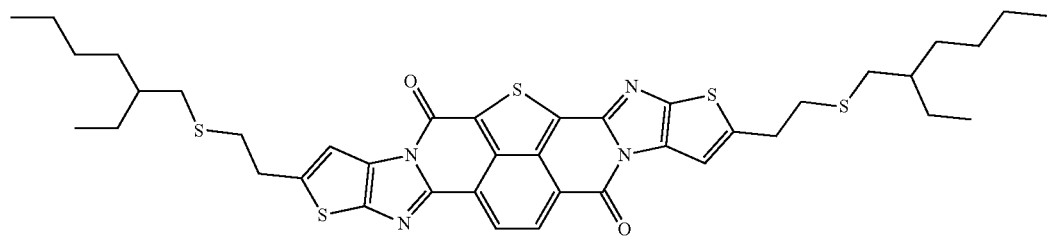
D-31
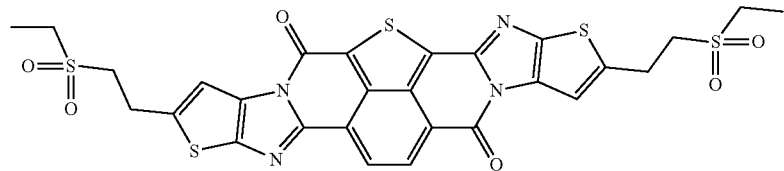
D-32
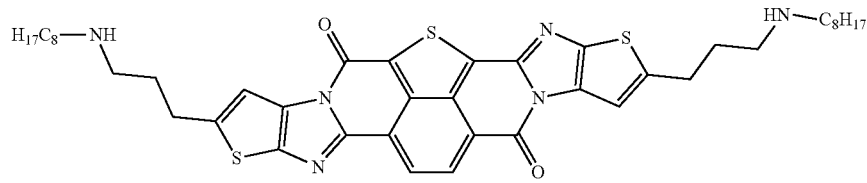
D-33
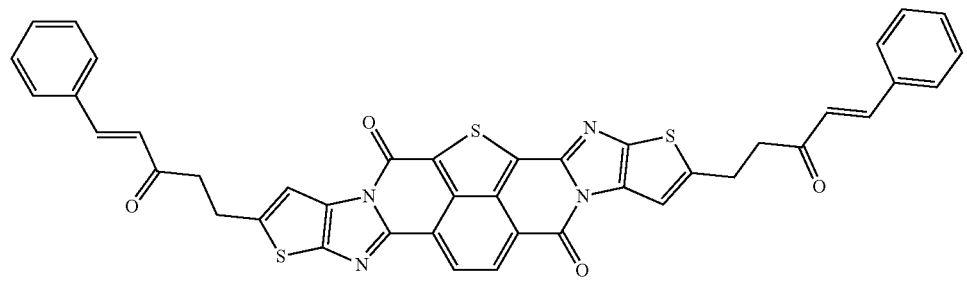
D-34
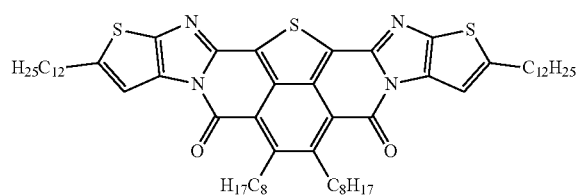
E-1
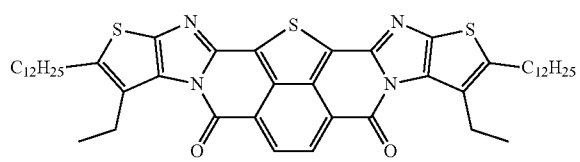
E-2

-continued
E-3
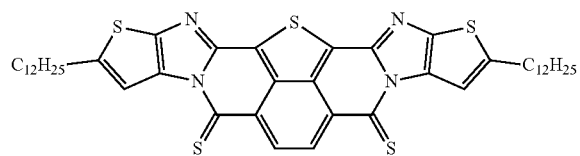
E-4
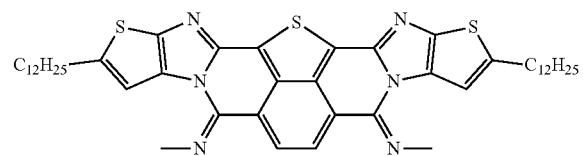
E-5
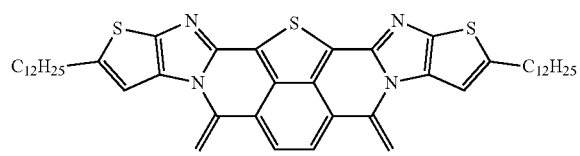
E-6
E-7
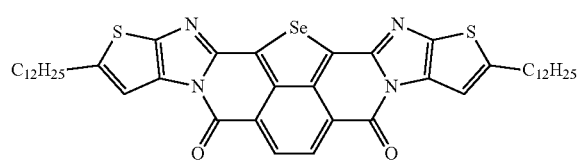
E-8
E-9
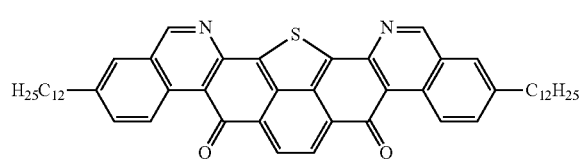
E-10
E-11
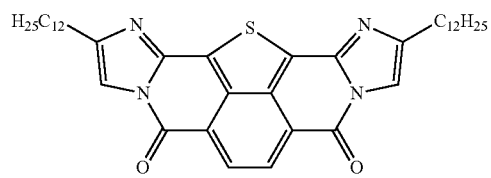
E-12
E-13
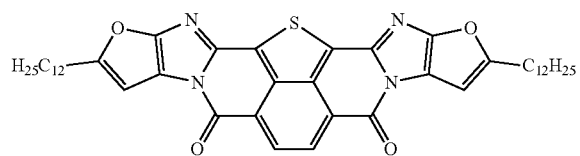
E-14
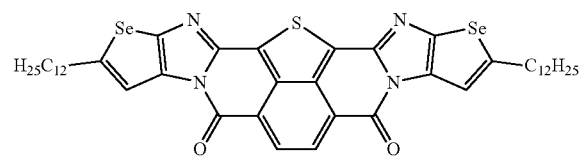
E-15
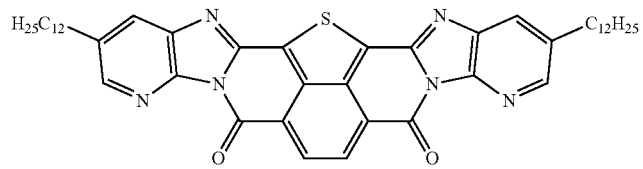
E-16
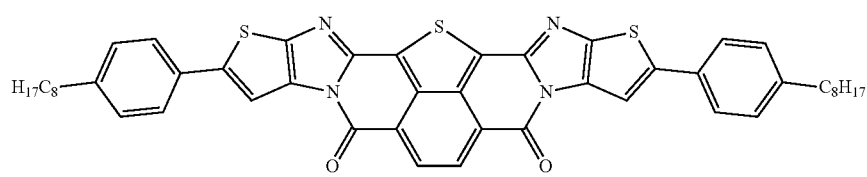

-continued
E-17
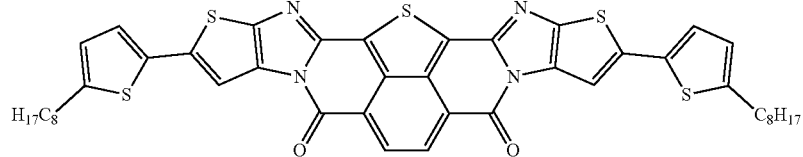
E-18
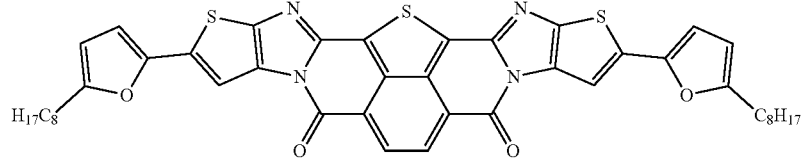
E-19
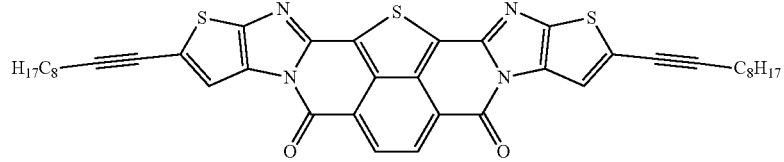
E-20
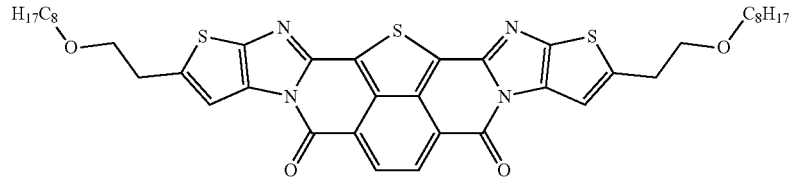
E-21
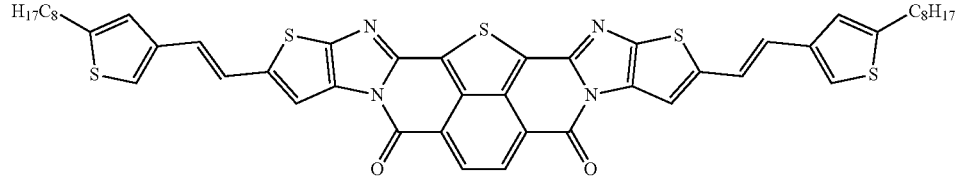
E-22
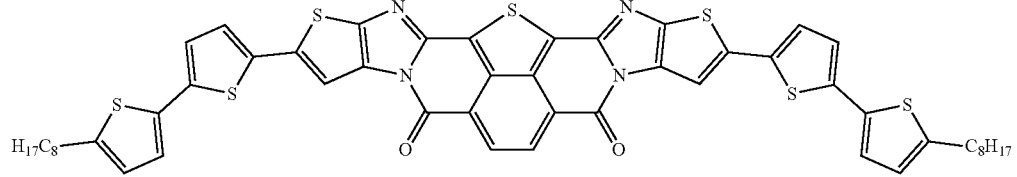
E-23
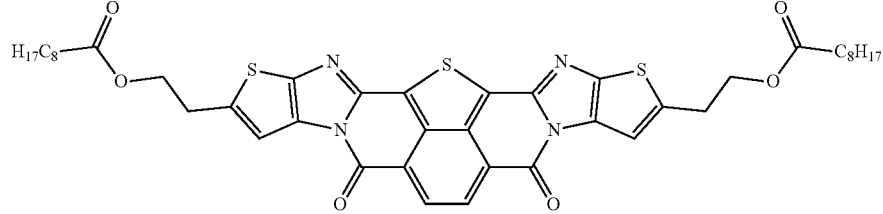
E-24
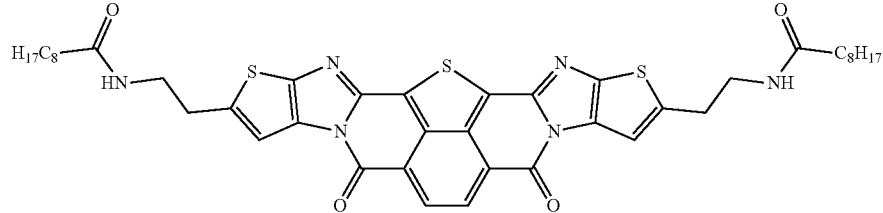

-continued
E-25
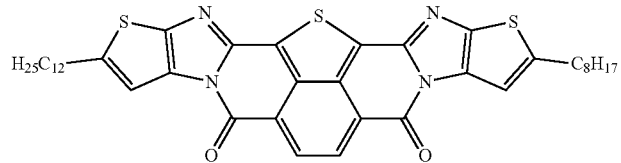
E-26
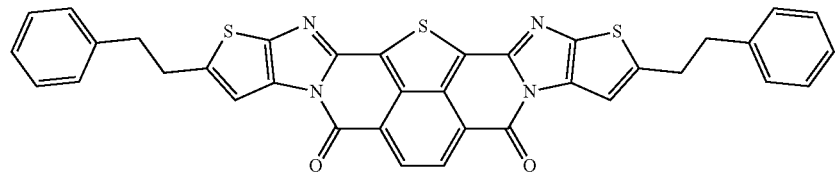
E-27
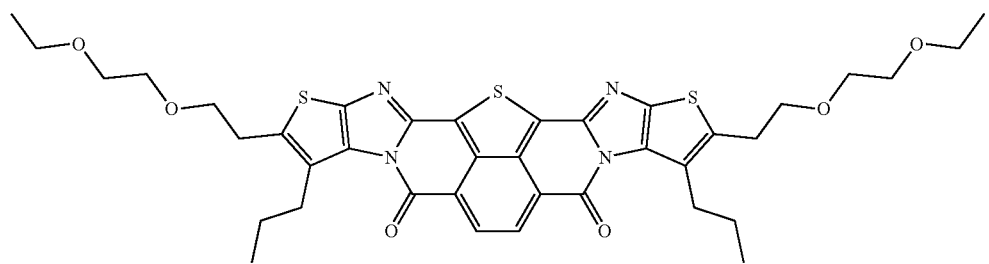
E-28
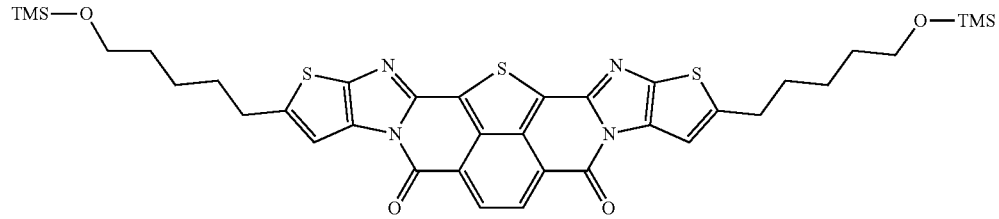
E-29
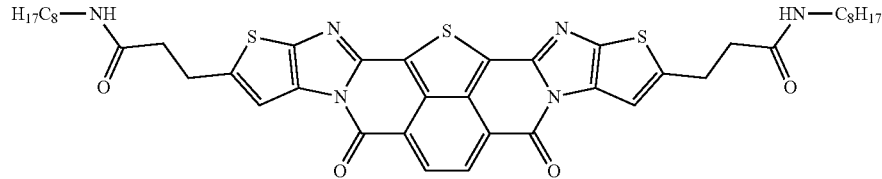
E-30
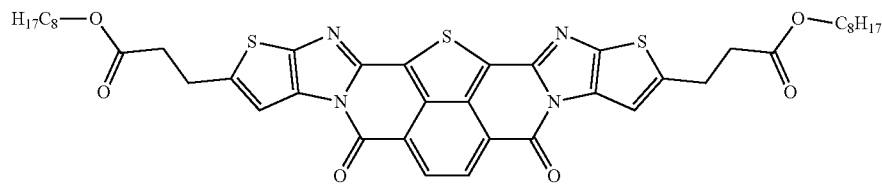
E-31
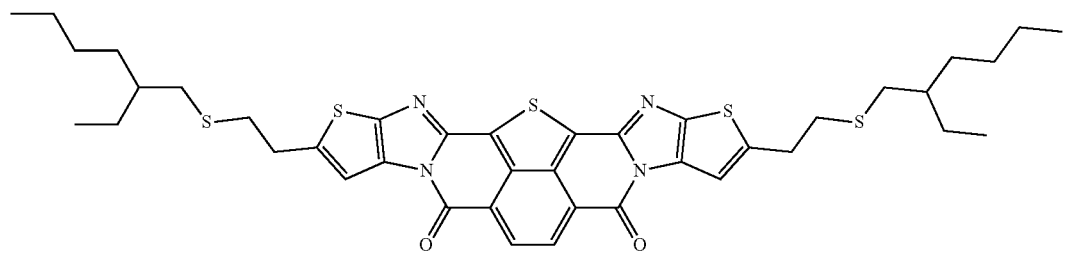

-continued

E-32
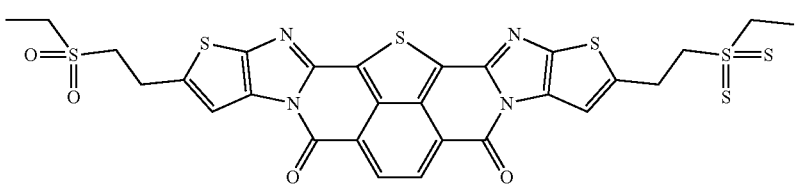

E-33
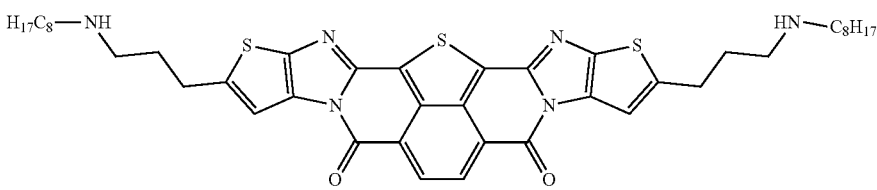

E-34
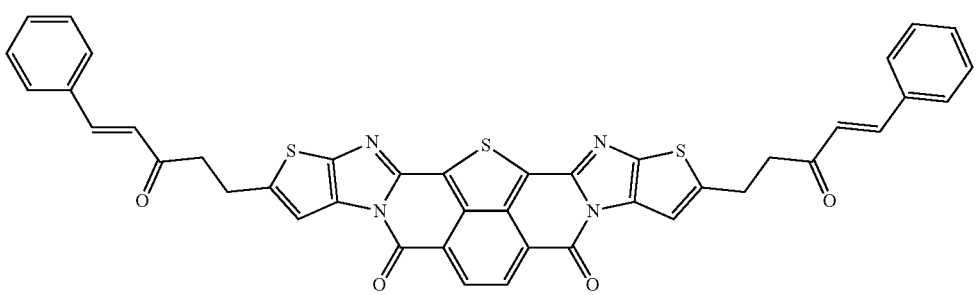

In another embodiment of the organic TFT element (hereinafter, also referred to as a "second embodiment"), the organic semiconductor layer contains a polymer having at least one structural unit represented by any one of Formulae (8) to (10). The "polymer" in the second embodiment is used in a meaning of including an oligomer (for example, an oligomer having about 2 to 10 repeating units). That is, in the present embodiment, the "polymer" is meant to include all compounds having two or more structural units represented by any one of Formulae (8) to (10).

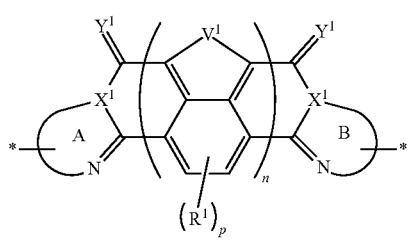
(8)

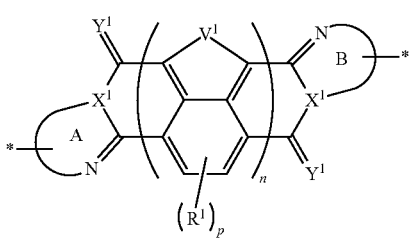
(9)

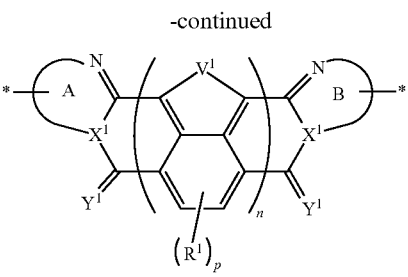
(10)

$X^1$, $Y^1$, $V^1$, the ring A, the ring B, $R^1$, p, and n are respectively the same as $X^1$, $Y^1$, $V^1$, the ring A, the ring B, $R^1$, p, and n in Formulae (1) to (3). Here, with respect to q and r in Formulae (6) and (7) relating to the rings A and B, q can be substituted with preferably 0 to 2 and more preferably 0, and preferable r can be substituted with 0. * represents a bonding site to be combined in the polymer.

With respect to the organic TFT element, in a case where the organic semiconductor layer includes a polymer having at least one structural unit represented by any one of Formulae (8) to (10), both of the desired carrier mobility and heat resistance can be realized. The reason thereof is not clear, but it is thought that the effect largely depends on the action of a mother nucleus (the fused polycyclic structure provided in each formula) of each of the above structural units. That is, since the mother nuclei forms the asymmetric fused ring structure in the minor axis direction, it is assumed that the intermolecular interaction between adjacent mother nuclei increases due to the dipole moment and the overlapping of the orbits increases to improve carrier mobility, and the rate of change in crystal structure is suppressed in a case of heating by increasing the intermolecular interaction between the adjacent mother nuclei to improve the heat resistance. This effect is more prominent in a case where the mother nucleus has a structure of being conjugated and linked in the main chain direction.

The polymer having at least one structural unit represented by Formulae (8) to (10) preferably has a structure represented by Formula (G).

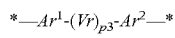 Formula (G)

In Formula (G), $Ar^1$ and $Ar^2$ each represent a single bond, or is a vinylene group, an ethynylene group, an arylene group, or a heteroarylene group, or is a divalent group formed by linking two or more groups selected from the vinylene group, the ethynylene group, the arylene group, and the heteroarylene group.

The aryl group that can be included in $Ar^1$ and $Ar^2$ preferably has 6 to 30 carbon atoms, more preferably 6 to 20 carbon atoms, and even more preferably 6 to 15 carbon atoms. Specific preferable examples of this arylene group include a phenylene group and a naphthylene group, and a phenylene group is preferable.

The heterocyclic arylene group that can be included in $Ar^1$ and $Ar^2$ is preferably a 5-membered aromatic heterocyclic ring, a fused heterocyclic ring including a 5-membered aromatic heterocyclic ring, a 6-membered aromatic heterocyclic ring, a fused heterocyclic ring including a 6-membered aromatic heterocyclic ring. The above heteroarylene group also includes an aspect in which these aromatic heterocyclic ring or a fused heterocyclic ring has a substituent.

Examples of the 5-membered aromatic heterocyclic ring and the fused heterocyclic ring including a 5-membered aromatic heterocyclic ring include a pyrrole ring, an imidazole ring, a pyrazole ring, an oxazole ring, a thiazole ring, an isoxazole ring, an isothiazole ring, a triazole ring, an oxadiazole ring, a thiadiazole ring, a furan ring, a thiophene ring, a benzimidazole ring, a benzoxazole ring, a benzothiazole ring, and an indazole ring.

Examples of the 6-membered aromatic heterocyclic ring and the fused heterocyclic ring including a 6-membered aromatic heterocyclic ring include a pyridine ring, a pyrimidine ring, a pyrazine ring, a pyridazine ring, a triazine ring, a quinoline ring, an isoquinoline ring, a quinoxaline ring, a phthalazine ring, a cinnoline ring, and a quinazoline ring.

In a case where $Ar^1$ and $Ar^2$ are divalent groups formed by linking two or more groups selected from a vinylene group, an ethynylene group, an arylene group, and a heteroarylene group, the molecular weight of $A^1$ and $Ar^2$ is preferably 48 to 1,000 and more preferably 48 to 600.

$Ar^1$ and $Ar^2$ are more preferably a single bond or a divalent group represented by Formula (Ar-1) or (Ar-2).

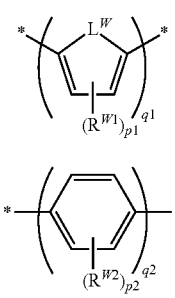

In Formula (Ar-1), $R^{W1}$ and $R^{W2}$ each represent an alkyl group. p1 is an integer of 0 to 2 and is preferably 0 or 1. p2 is an integer of 0 to 4, preferably an integer of 0 to 3, and more preferably an integer of 0 to 2.

Preferable aspects of the alkyl group that can be employed as $R^{W1}$ and $R^{W2}$ are the same as the aspect that can be employed as $R^{X1}$.

$L^W$ represents a chalcogen atom. $L^W$ is preferably an oxygen atom, a sulfur atom, or a selenium atom, and more preferably a sulfur atom.

q1 and q2 are is an integer of 1 to 4, preferably 1 or 2, and more preferably 1.

In Formula (G), Vr represents a divalent conjugated group having 2 to 40 carbon atoms. Vr is preferably a structure selected from Formulae ($V_D$-1) to ($V_D$-16), and ($V_A$-1) to ($V_A$-11).

p3 is an integer of 1 to 6, preferably 1 or 2, and more preferably 1.

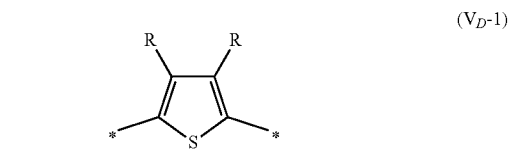 ($V_D$-1)

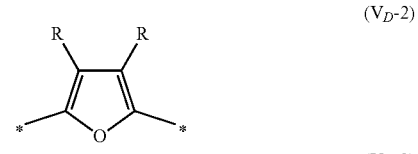 ($V_D$-2)

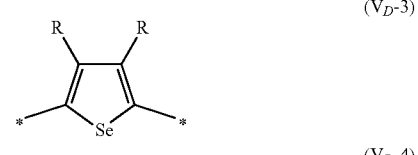 ($V_D$-3)

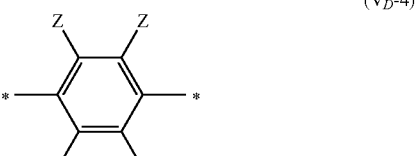 ($V_D$-4)

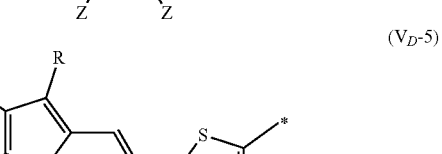 ($V_D$-5)

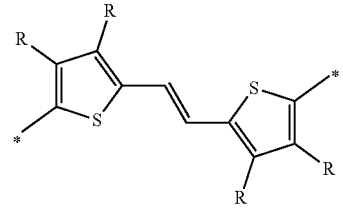 ($V_D$-6)

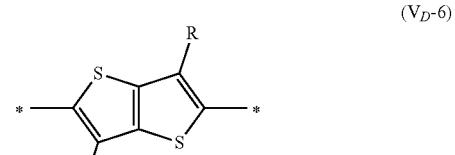 ($V_D$-6)

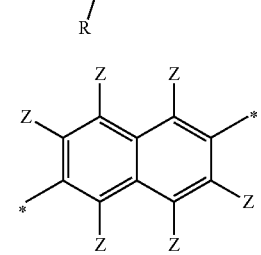 ($V_D$-7)

-continued
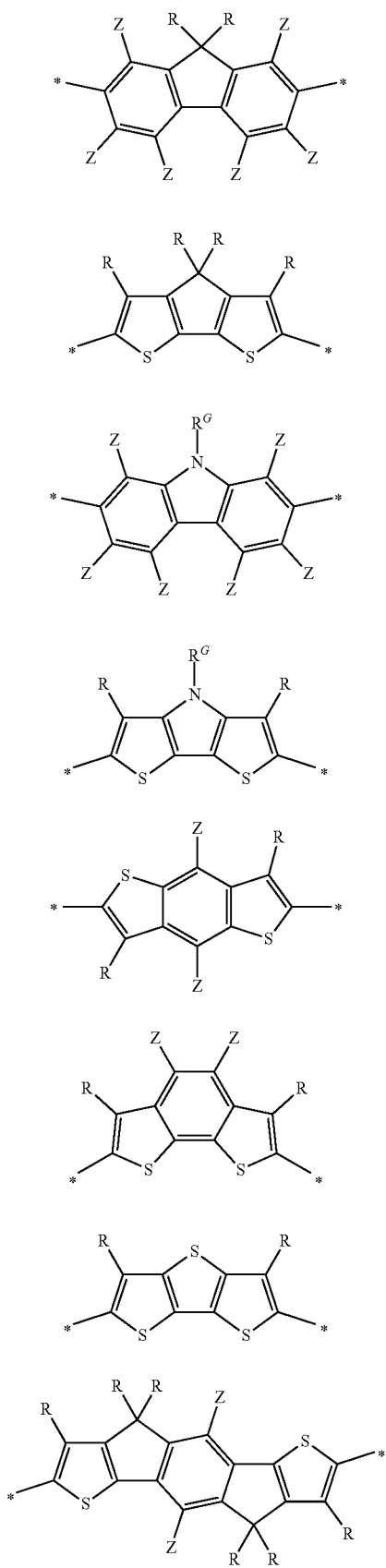
(V_D-8)
(V_D-9)
(V_D-10)
(V_D-11)
(V_D-12)
(V_D-13)
(V_D-14)
(V_D-15)
-continued
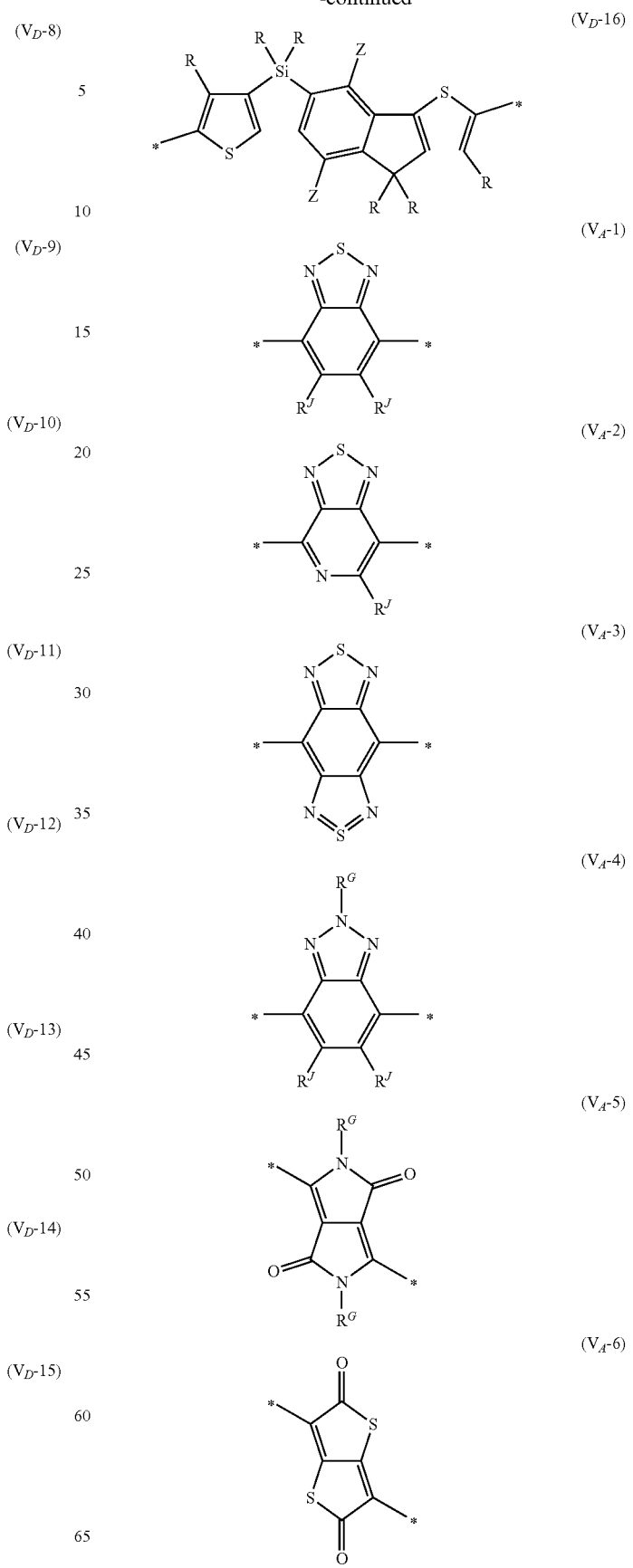
(V_D-16)
(V_A-1)
(V_A-2)
(V_A-3)
(V_A-4)
(V_A-5)
(V_A-6)

-continued

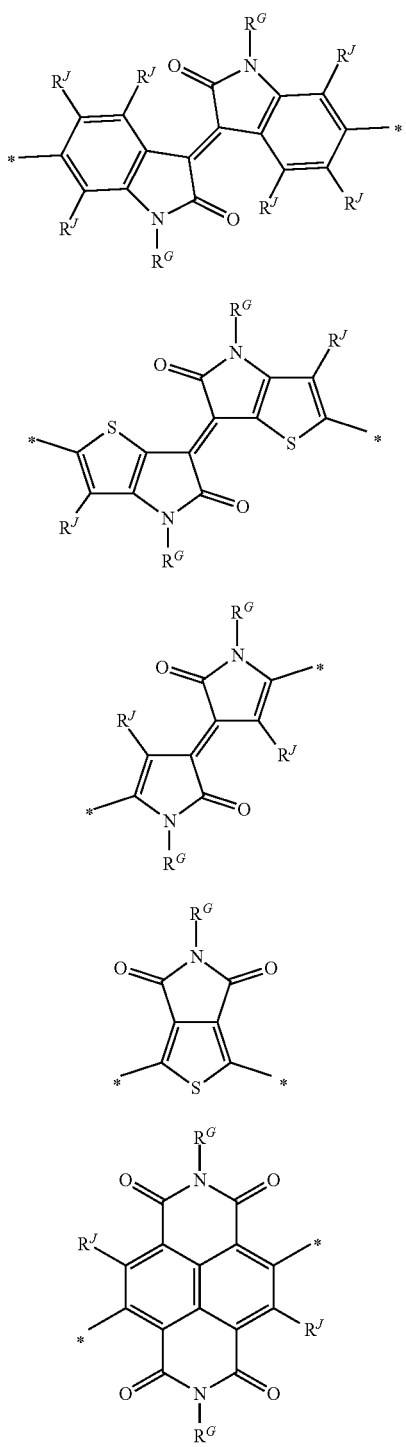

(V$_A$-7)
(V$_A$-8)
(V$_A$-9)
(V$_A$-10)
(V$_A$-11)

In each of the formulae, * indicates a bonding site.

R and Z each represent a hydrogen atom, a halogen atom (preferably a fluorine atom, a chlorine atom, a bromine atom, or an iodine atom), or an alkyl group. Preferable aspects of the alkyl group that can be employed as R and Z are the same as the aspect that can be employed as $R^a$ to $R^d$.

$R^G$ represents an alkyl group. Preferable aspects of the alkyl group are the same as the aspect that can be employed as $R^a$ to $R^d$.

$R^J$ represents a hydrogen atom, an alkyl group, a cyano group, or a halogen atom. Preferable aspects of the alkyl group and a halogen atom that can be employed as $R^J$ are the same as the aspect of the alkyl group and a halogen atom that can be employed as Z.

Vr is preferably a divalent group represented by any one of Formulae (V$_D$-1) to (V$_D$-16).

Since the above polymer has a structure represented by Formula (G), a bias of electron density occurs in the main chain, the bias increases the interaction between the main chains to increase the overlapping of the orbits, and thus improvement of carrier mobility and improvement of heat resistance can be achieved.

The polymer preferably has an aspect of alternately having a structural unit represented by any one of Formulae (8) to (10) and a structure represented by Formula (G). This structure is preferable, because the polymer can have an aspect of being conjugated in the main chain direction, and the bias of ionization potential in the main chain can be reduced.

The weight-average molecular weight of the polymer having at least one kind of the structural unit represented by Formulae (8) to (10) is 1,000 to 500,000 and more preferably 1,000 to 300,000.

In the present invention, the weight-average molecular weight and the number-average molecular weight are measured by a gel permeation chromatography (GPC) method and are calculated in terms of standard polystyrene. Specifically, for example, in GPC, HLC-8121 GPC (manufactured by Tosoh Corporation), is used, two units of TSKgel GMH$_{HR}$-H (20) HT (manufactured by Tosoh Corporation, 7.8 mm ID×30 cm) are used as and 1,2,4-trichlorobenzene is used as an eluent. As the conditions, a sample concentration of 0.02 mass %, a flow rate of 1.0 mL/min, a sample injection amount of 300 μL, and a measurement temperature of 160° C. are set, and an infrared (IR) detector is used, so as to perform the GPC. The calibration curve is manufactured by using 12 samples of "Standard sample TSK standard, polystyrene": "F-128", "F-80", "F-40", "F-20", "F-10j", "F-4", "F-2", "F-1", "A-5000", "A-2500", "A-1000", and "A-500".

The content of the structural unit represented by Formulae (8) to (10) in the polymer having at least one structural unit represented by Formulae (8) to (10) is preferably 10 to 100 mass %, more preferably 30 to 90 mass %, and even more preferable 50 to 80 mass % in total.

The terminal structure of the polymer having at least one structural unit represented by any one of Formulae (8) to (10) is not particularly limited and do not uniformly determined, according to the presence or absence of other repeating units, the type of base material used in the synthesis, or the types of the quenching agent during synthesis (reaction stopping agent). Examples of the structure of the terminal include a hydrogen atom, a hydroxy group, a halogen atom, an ethylenically unsaturated group, an alkyl group, and an aromatic heterocyclic ring group (preferably a thiophene ring), or an aromatic hydrocarbon group (preferably a benzene ring).

The method of synthesizing at least one structural unit represented by any one of Formulae (8) to (10) is not particularly limited, and the synthesis can be performed with reference to a well-known method. For example, the structural unit can be synthesized by using a cross coupling reaction such as a Suzuki coupling reaction or a Stille coupling reaction. In the synthesis of the polymer having at least one structural unit represented by Formulae (8) to (10), for example, publications of JP2010-527327A, JP2007-516315A, JP2014-515043A, JP2014-507488A, JP2011-501451A, JP2010-018790A, WO2012/174561A, JP2011-514399A, and JP2011-514913A can be referred to.

Specific examples of the polymer having at least one structural unit represented by Formulae (8) to (10) are provided below, but the present invention is not limited to these aspects.
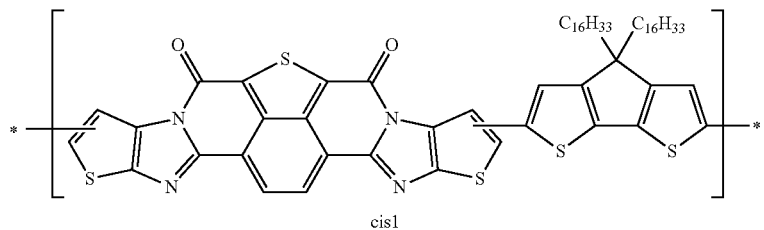
B-1
cis1
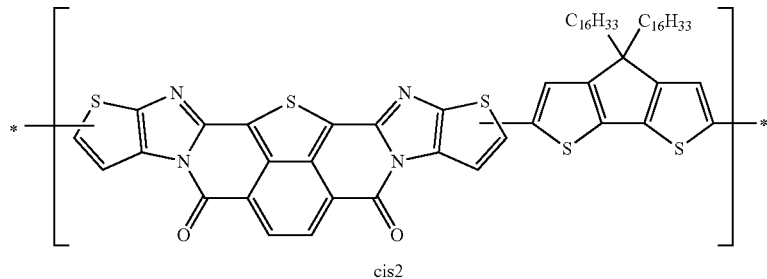
B-2
cis2
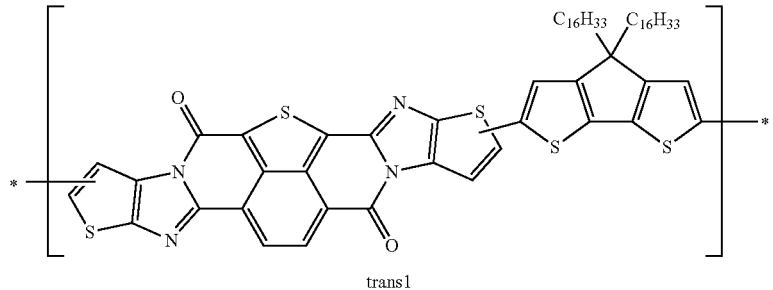
B-3
trans1
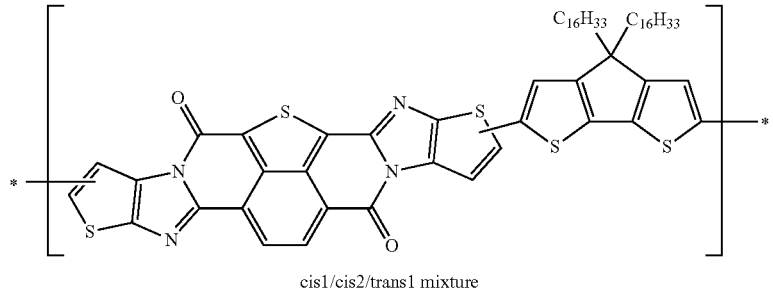
B-4
cis1/cis2/trans1 mixture
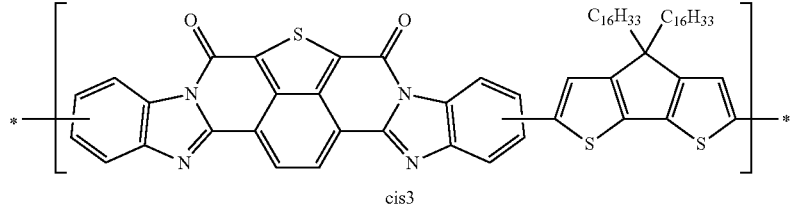
B-5
cis3

-continued
B-6
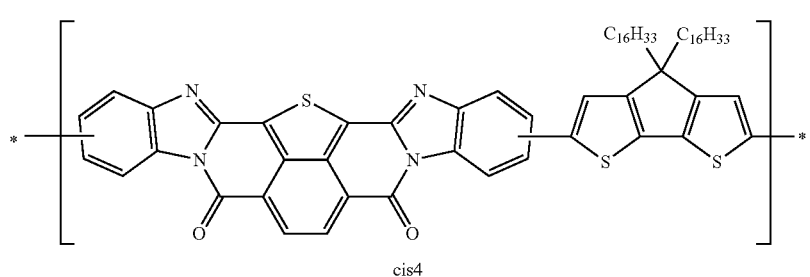
cis4
B-7
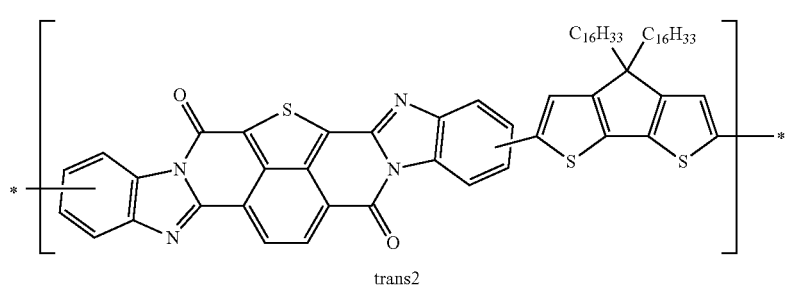
trans2
B-8
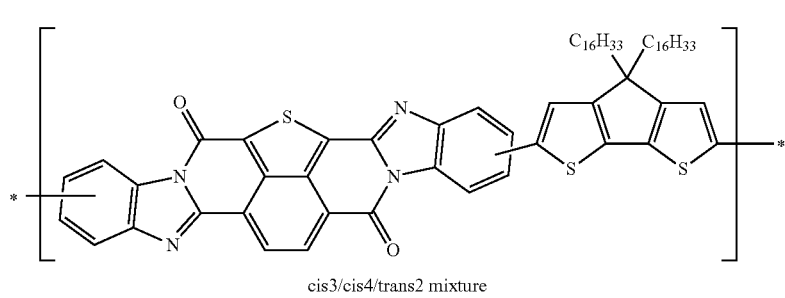
cis3/cis4/trans2 mixture
B-9
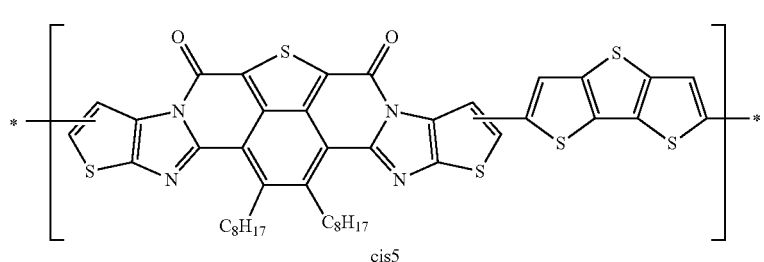
cis5
B-10
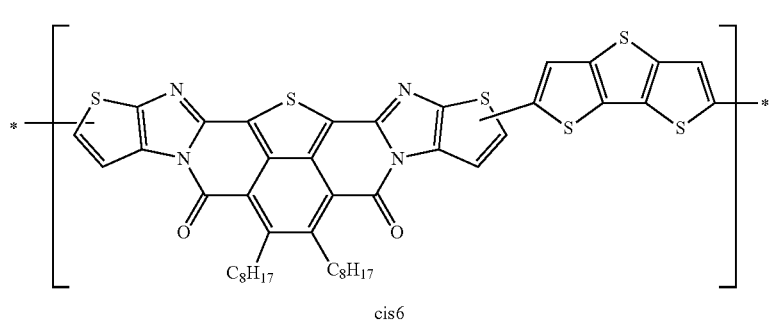
cis6

B-11
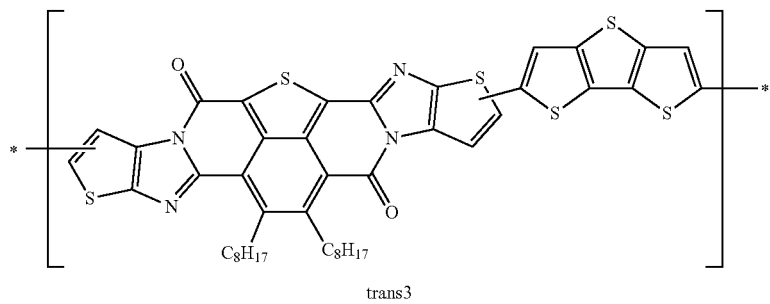
trans3
B-12
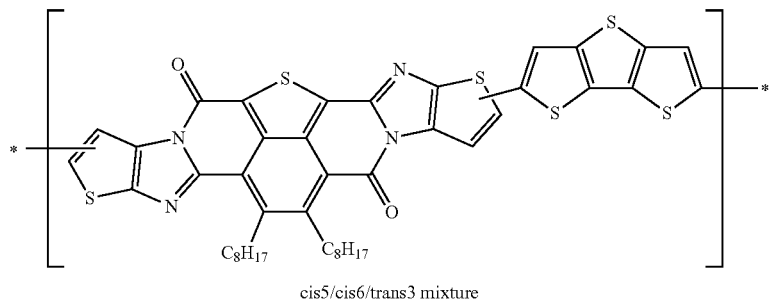
cis5/cis6/trans3 mixture
B-13
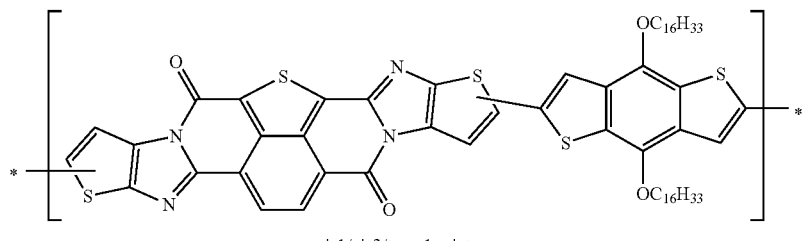
cis1/cis2/trans1 mixture
B-14
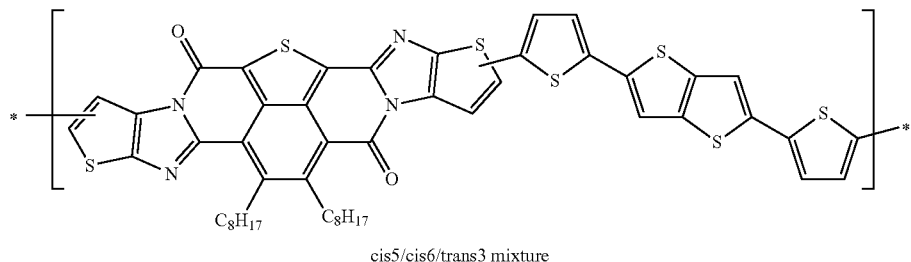
cis5/cis6/trans3 mixture
B-15
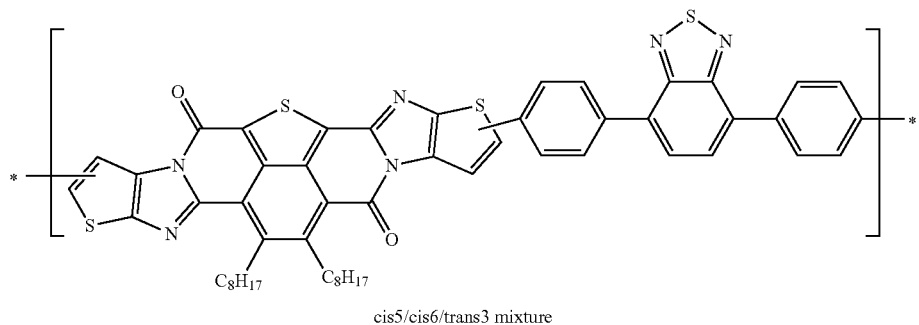
cis5/cis6/trans3 mixture -continued
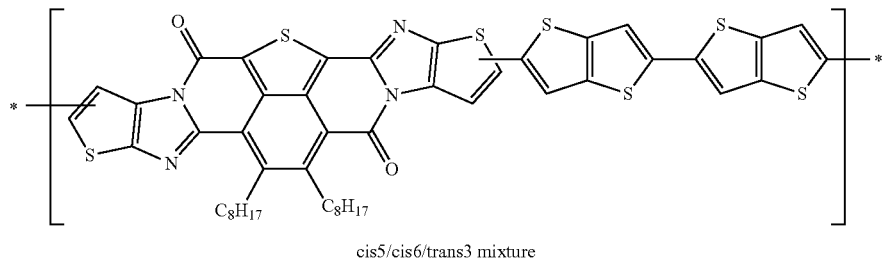
B-16
cis5/cis6/trans3 mixture
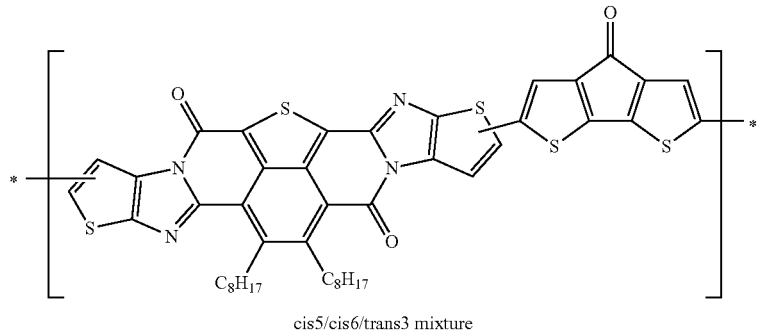
B-17
cis5/cis6/trans3 mixture
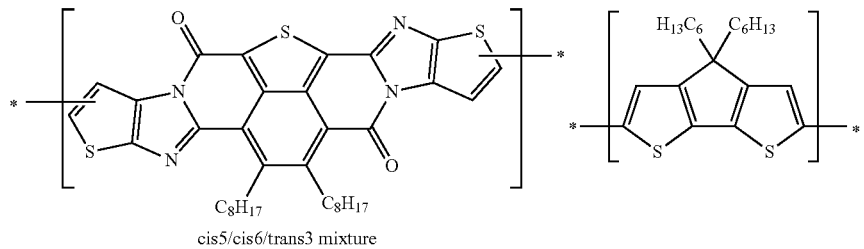
B-18
cis5/cis6/trans3 mixture
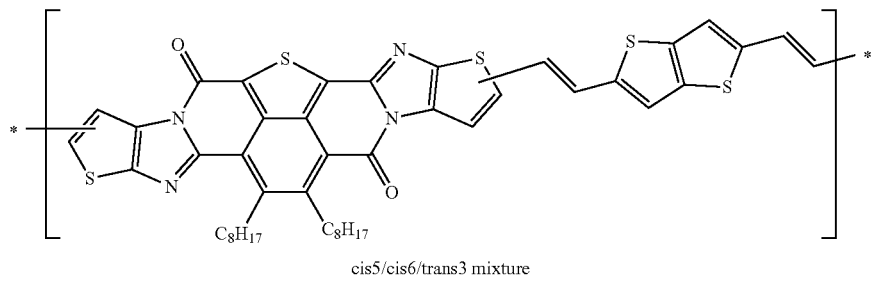
B-19
cis5/cis6/trans3 mixture
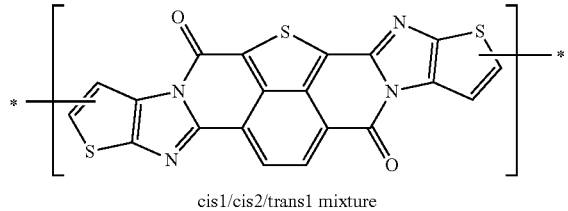
B-20
cis1/cis2/trans1 mixture
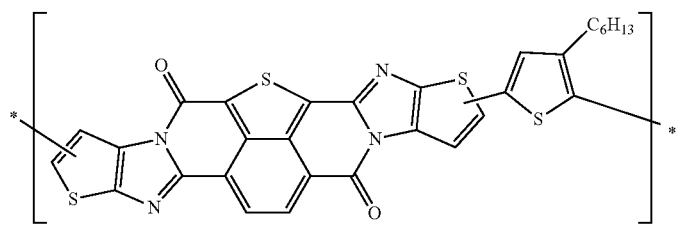
F-1

-continued
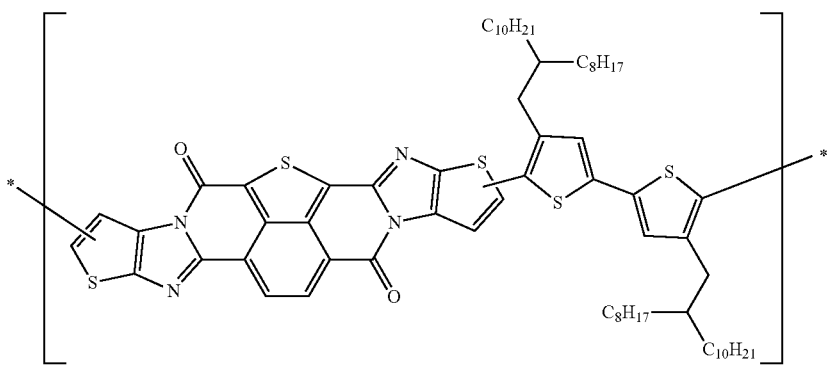
F-2
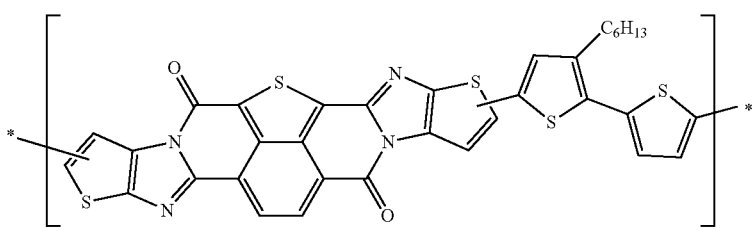
F-3
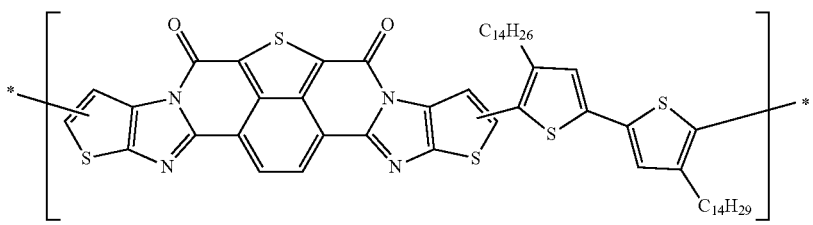
F-4
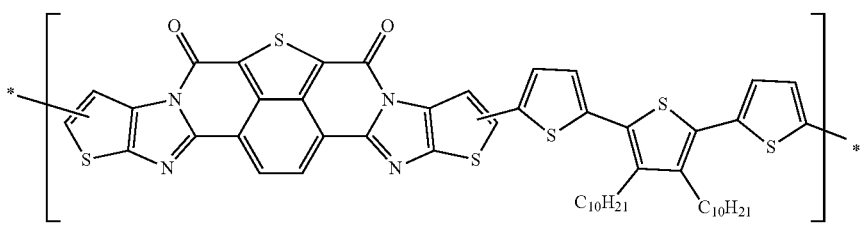
F-5
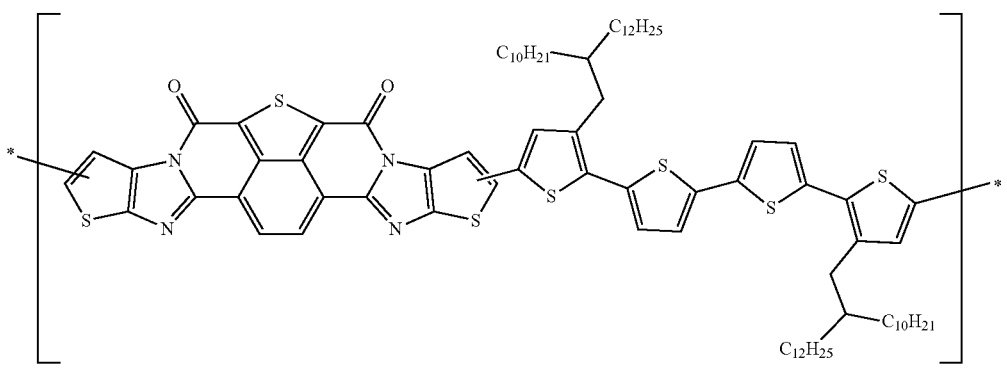
F-6

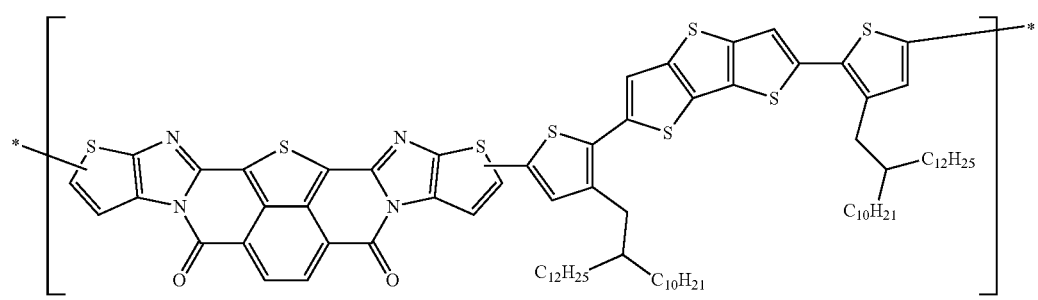
F-7
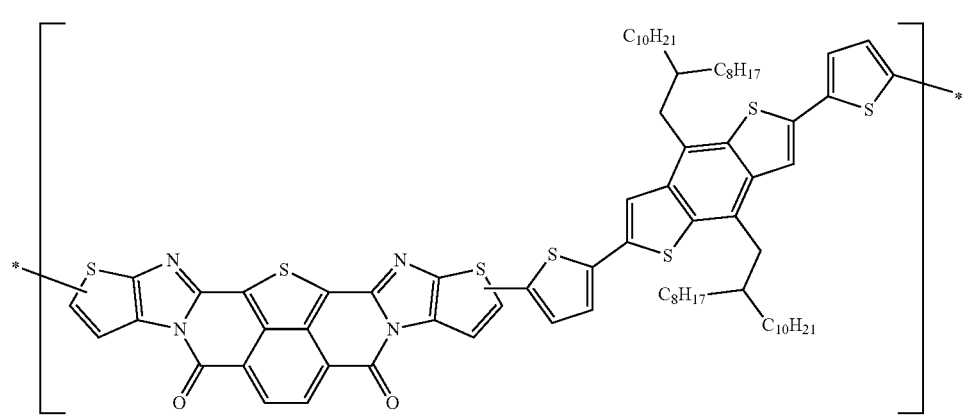
F-8
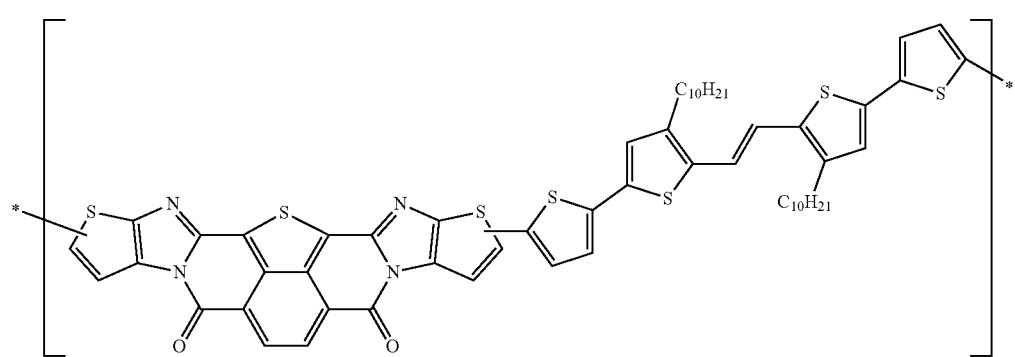
F-9
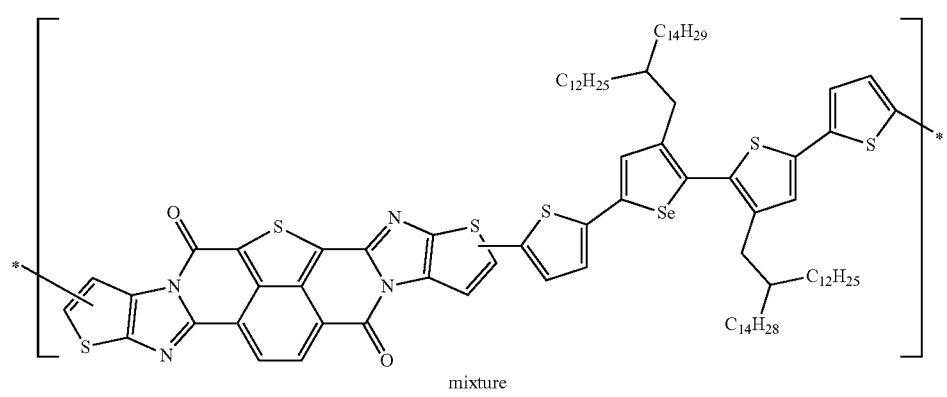
F-10
mixture

F-11
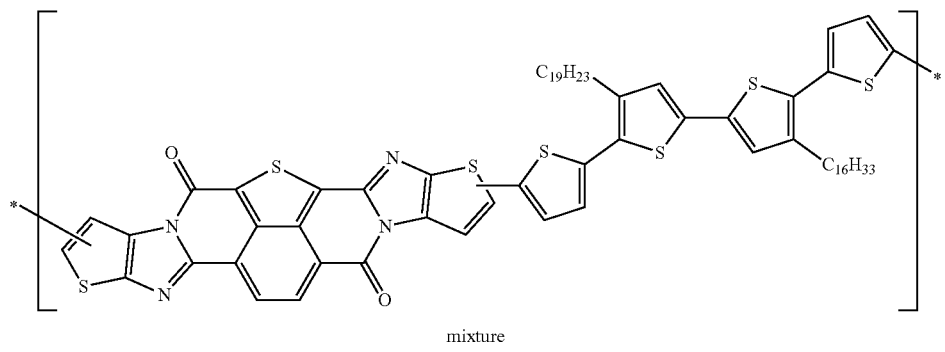
mixture
F-12
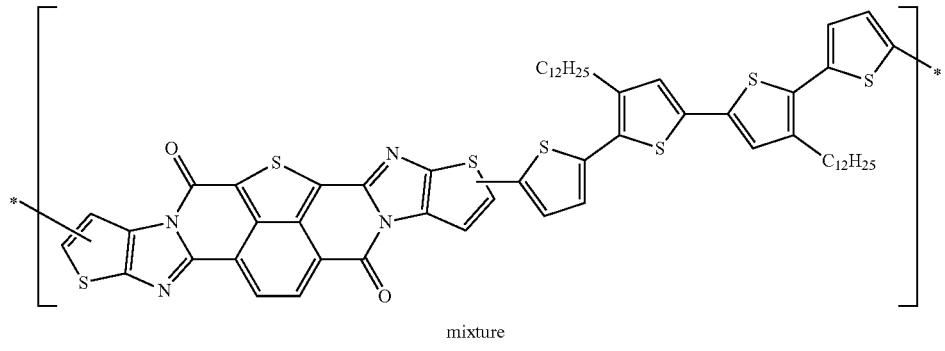
mixture
F-13
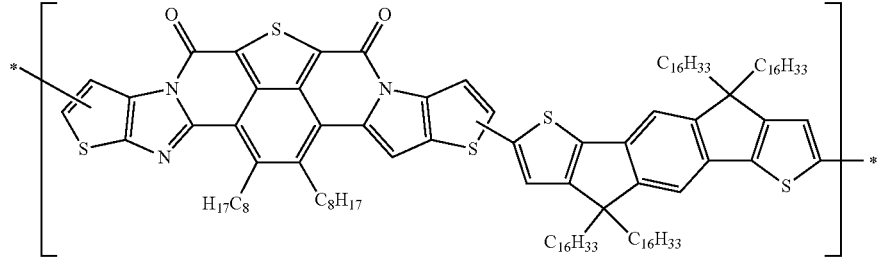
F-14
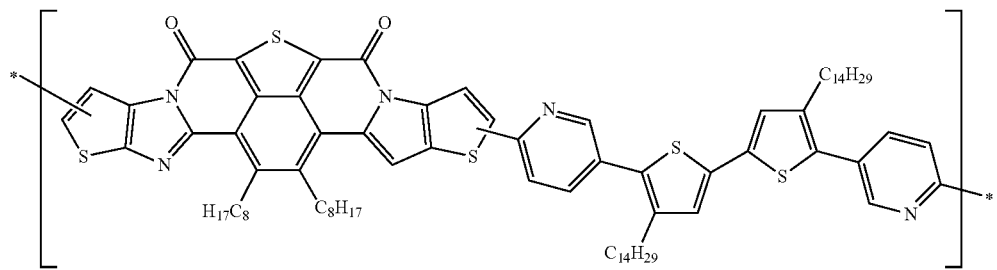
F-15
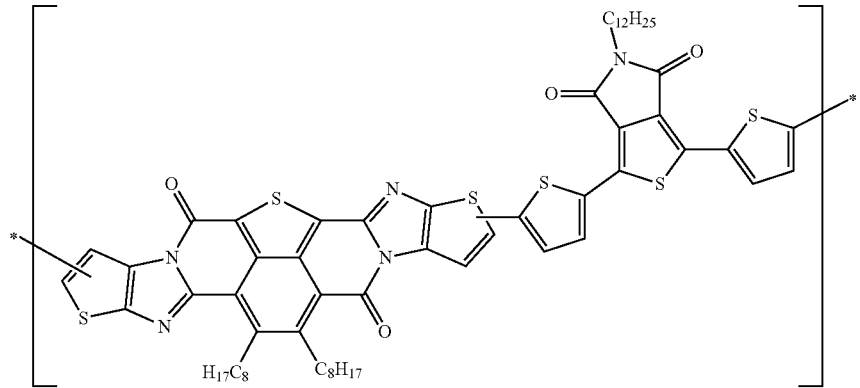

-continued
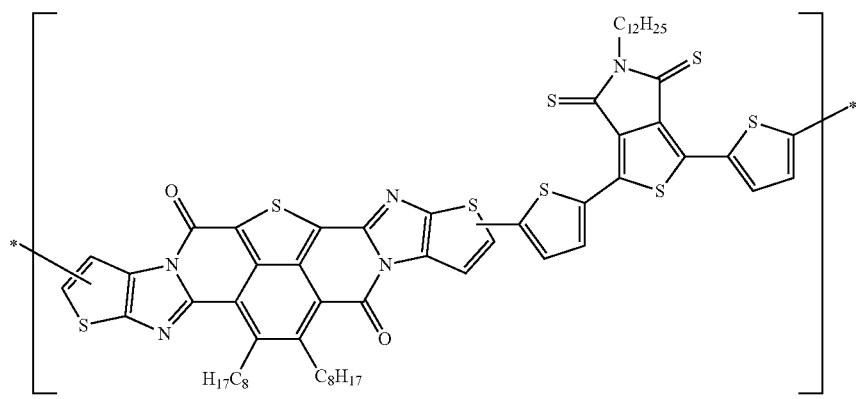
F-16
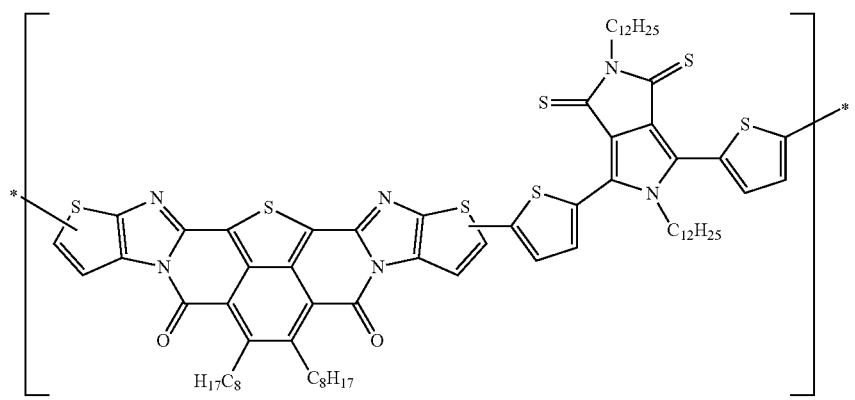
F-17
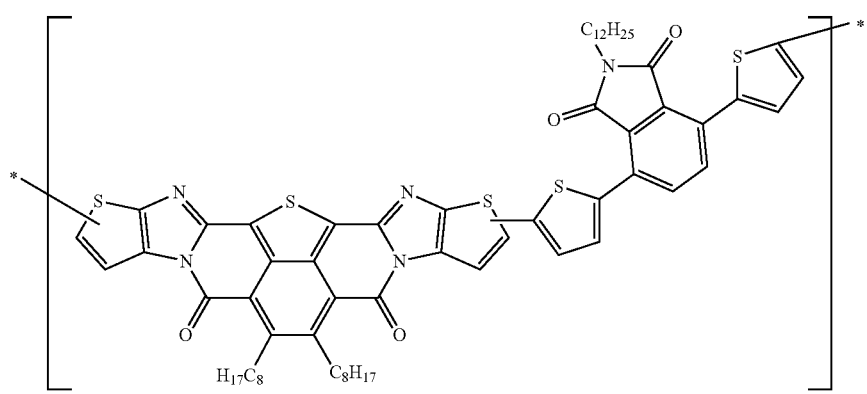
F-18
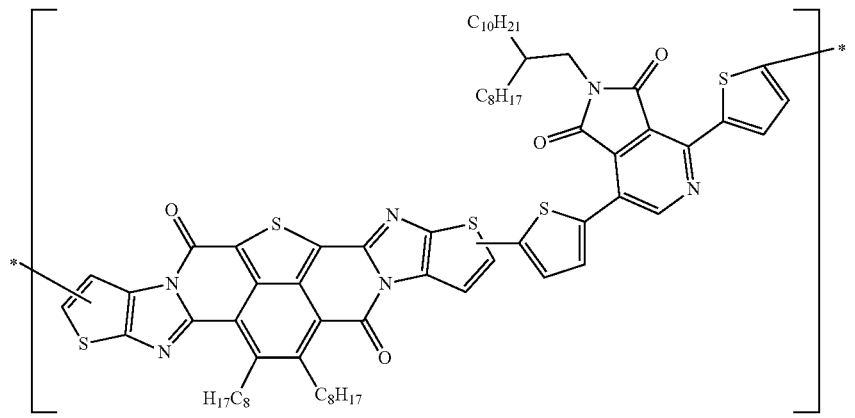
F-19

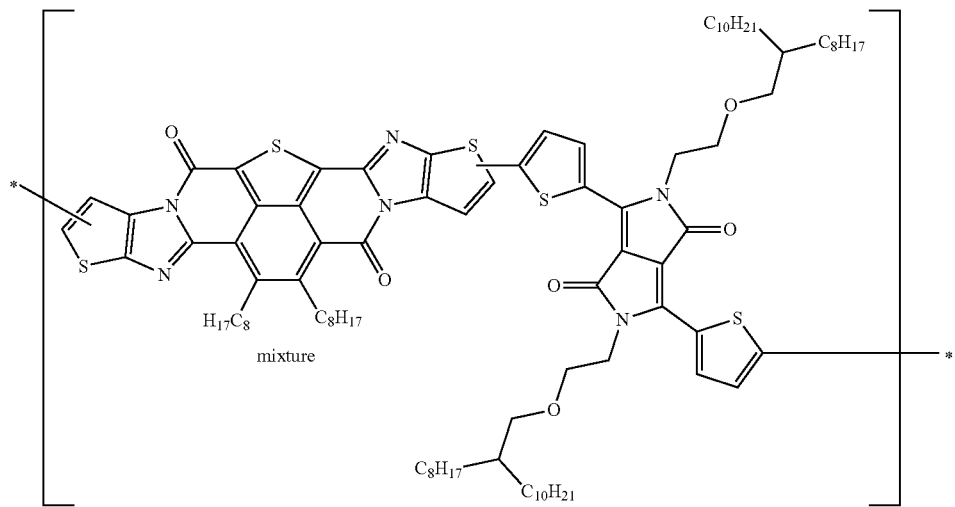
F-20
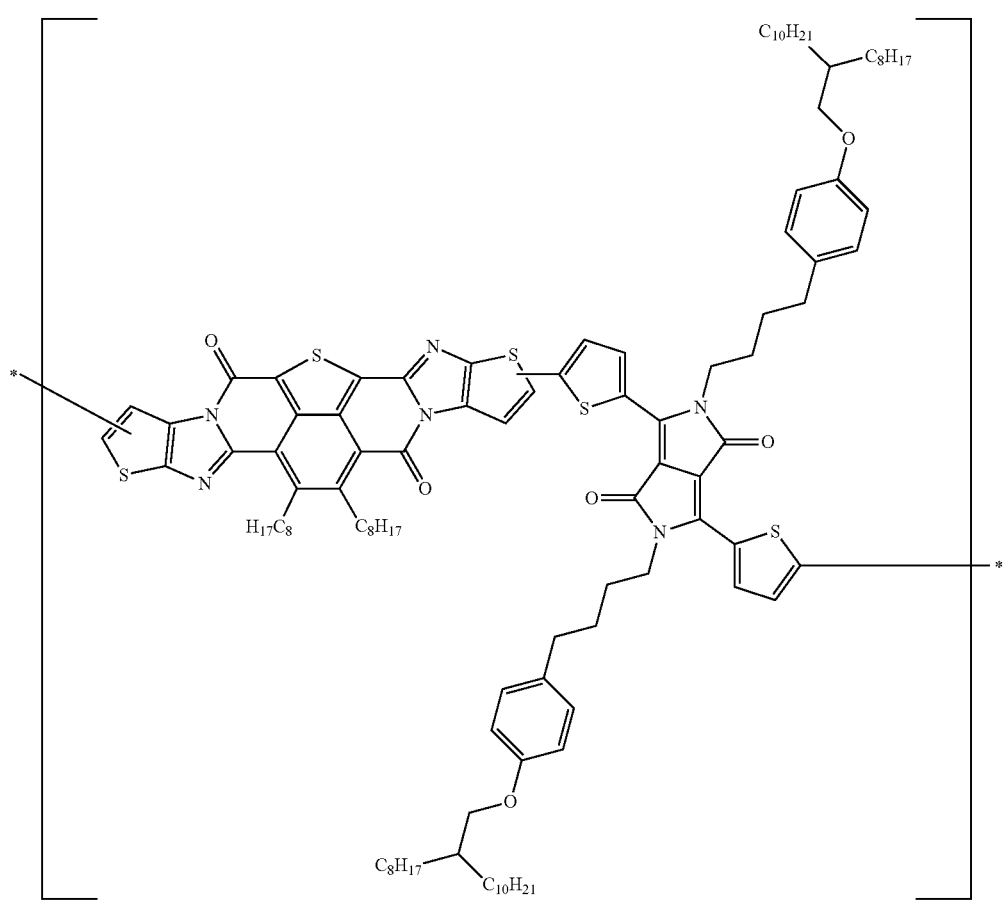
F-21

-continued
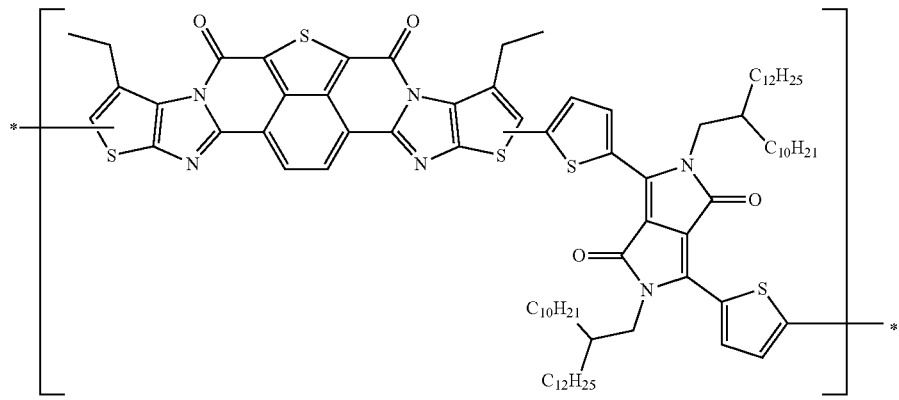
G-1
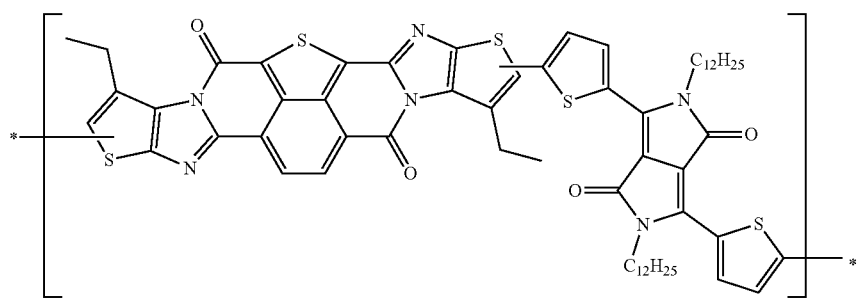
G-2
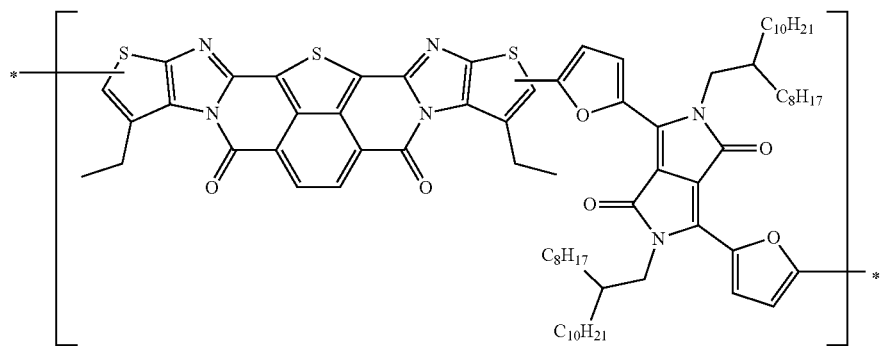
G-3
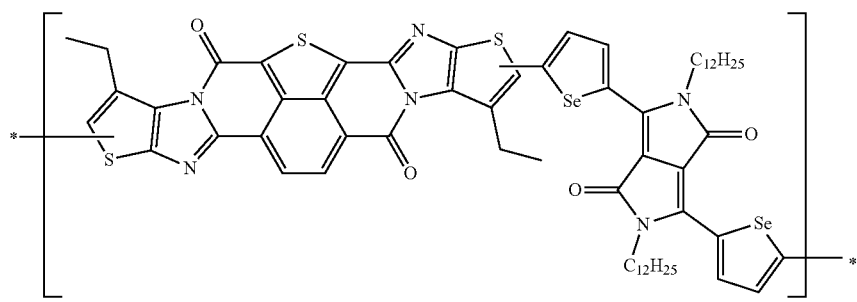
G-4

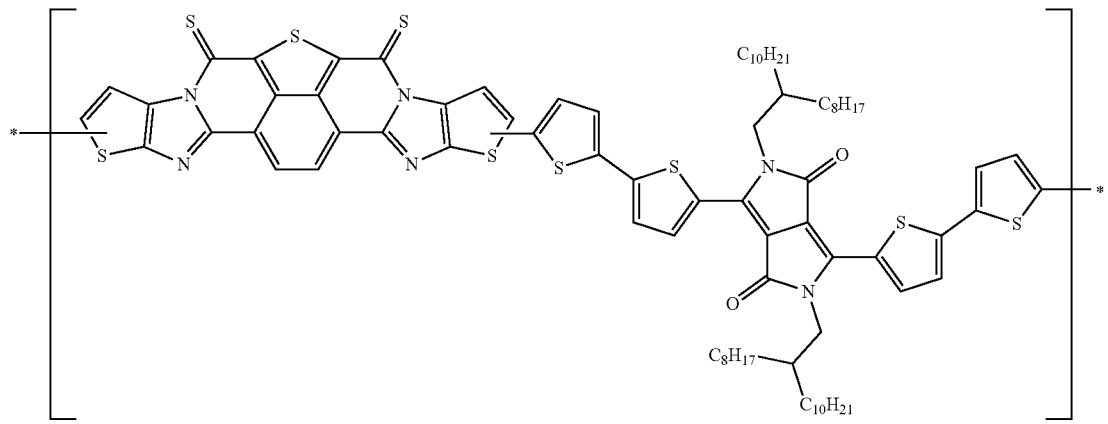
G-5
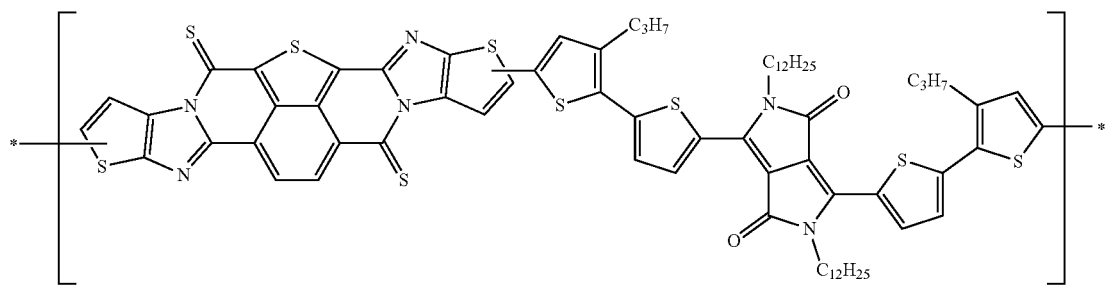
G-6
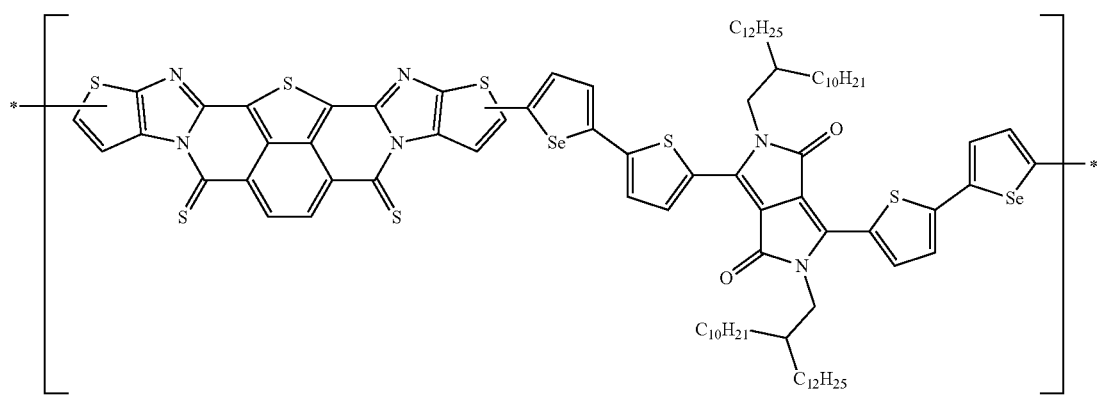
G-7
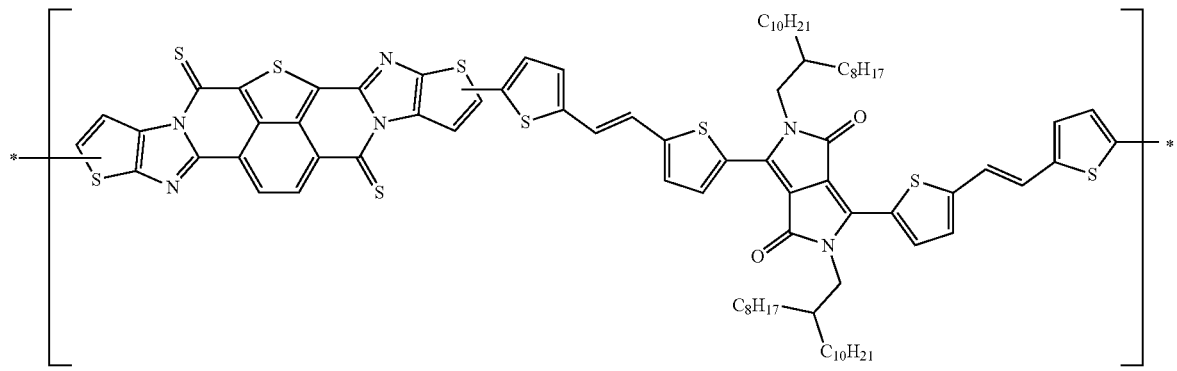
G-8

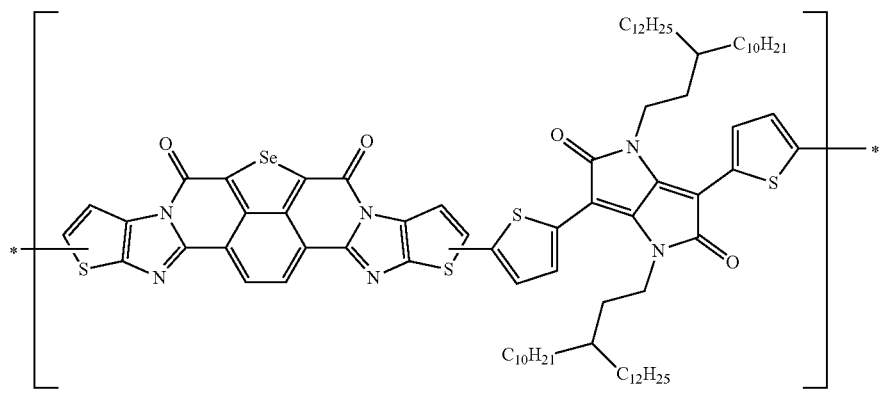
G-9
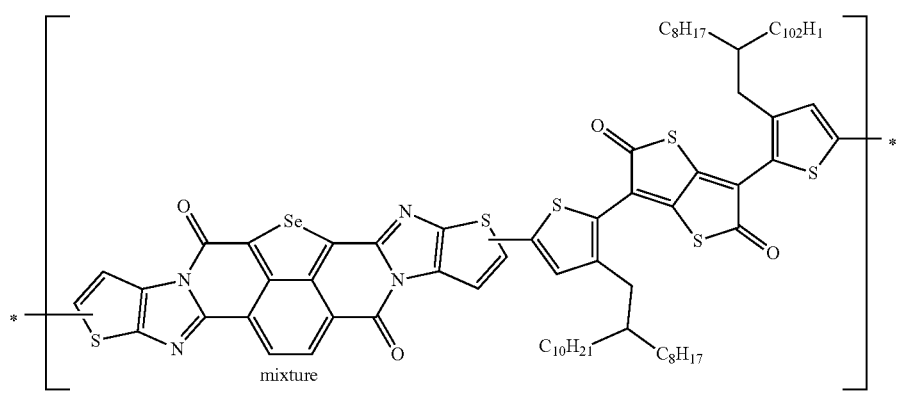
G-10
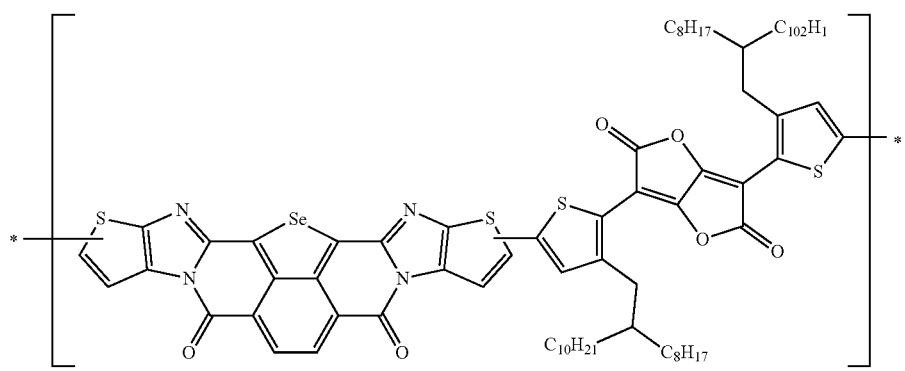
G-11

-continued
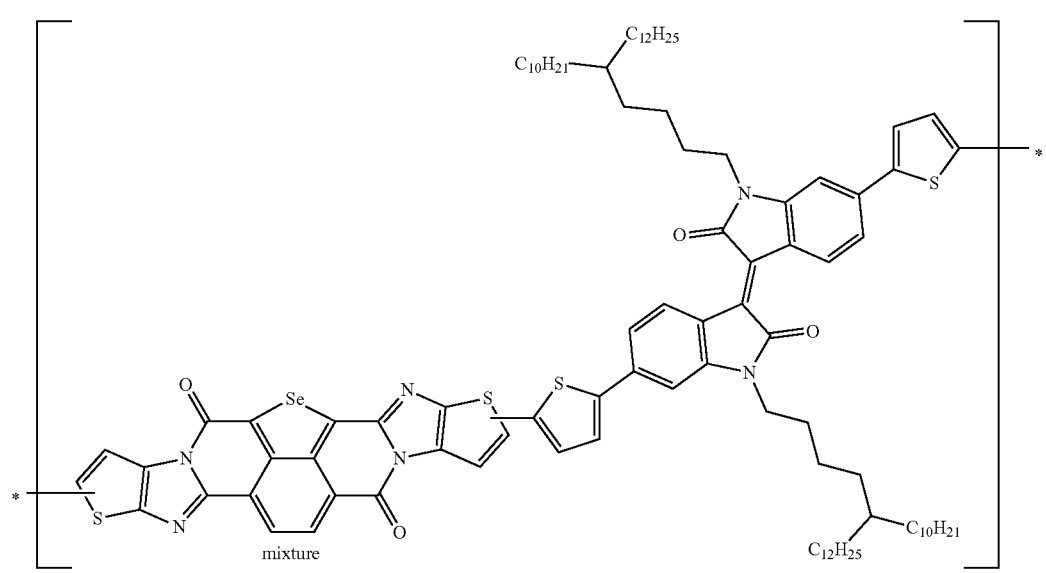
G-12
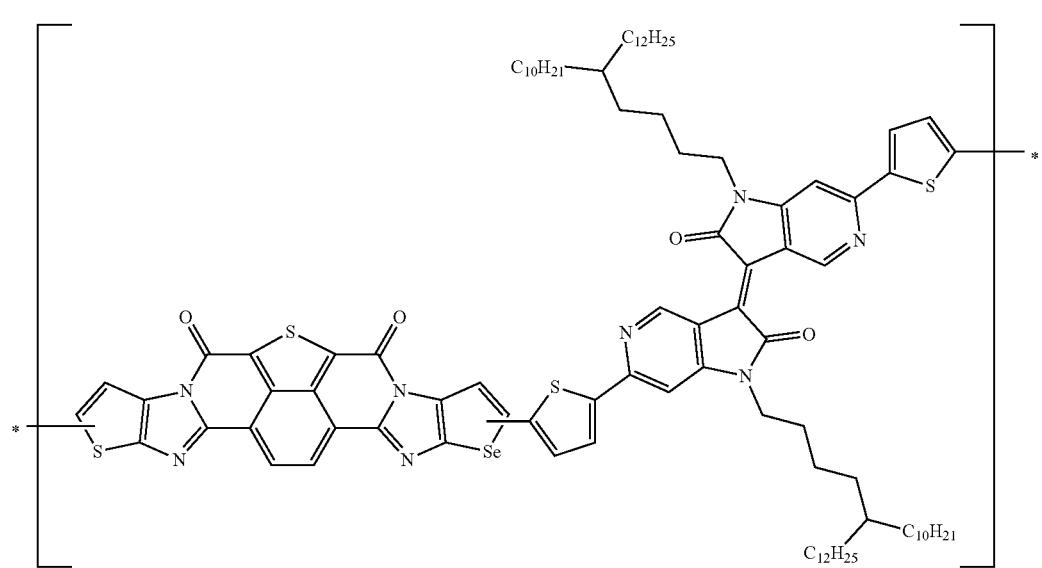
G-13
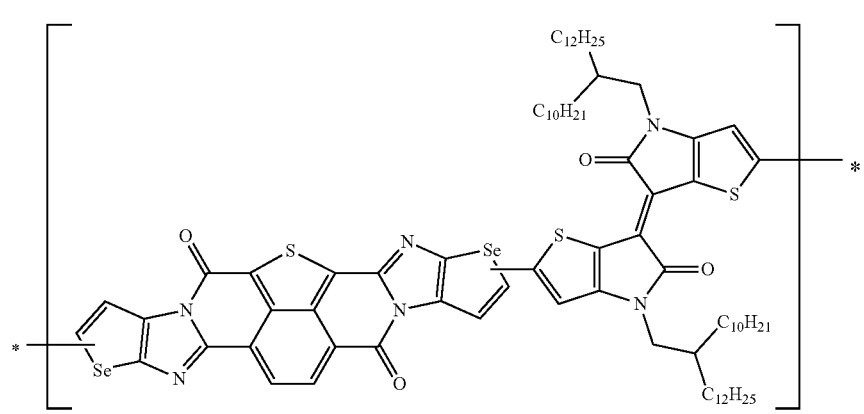
G-14

G-15
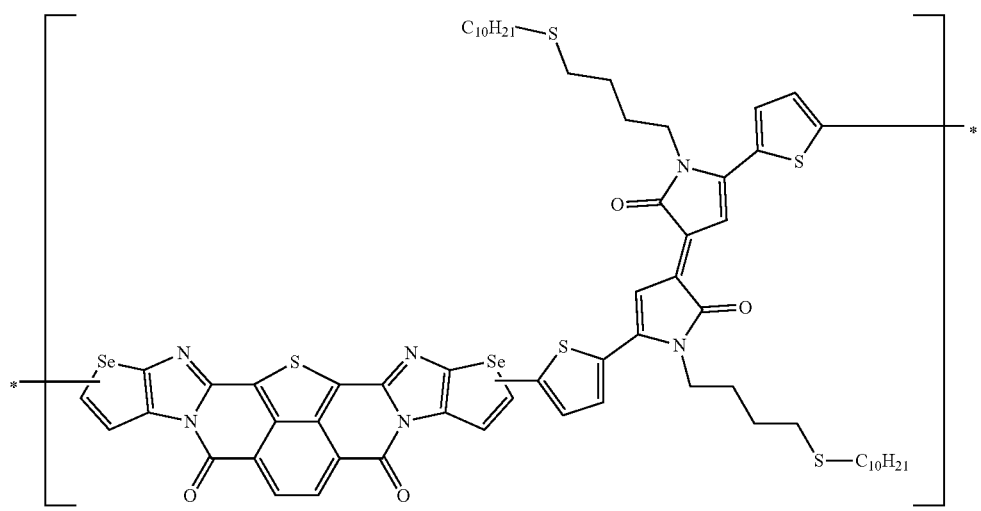
G-16
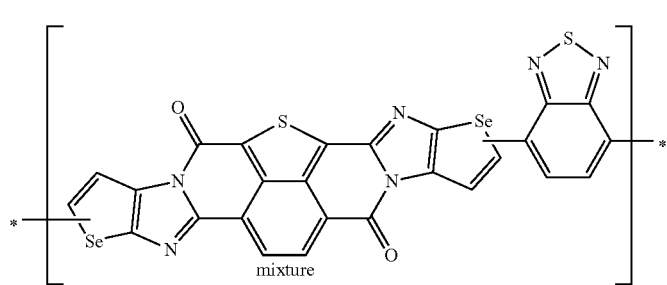
G-17
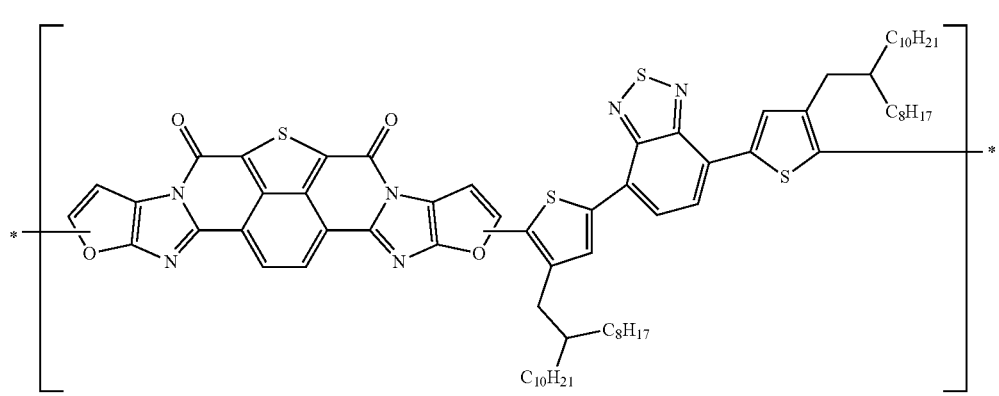
G-18
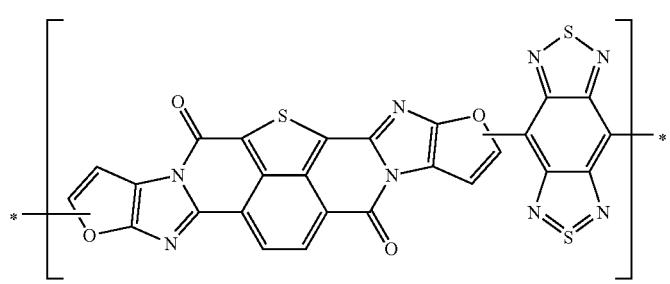

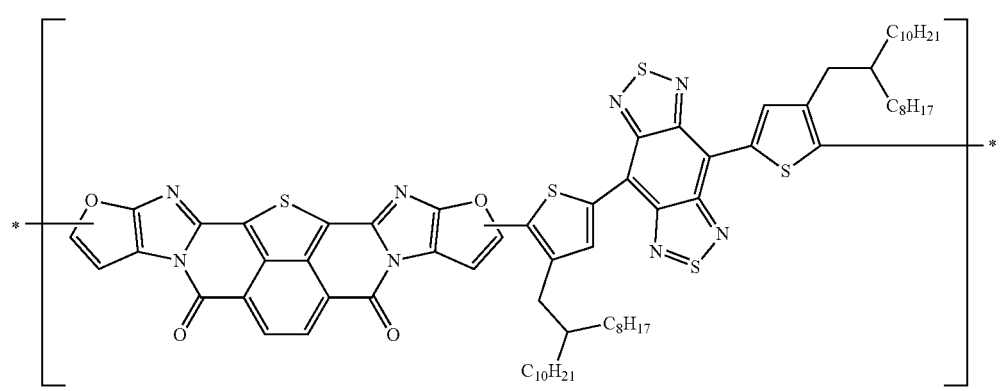
G-19
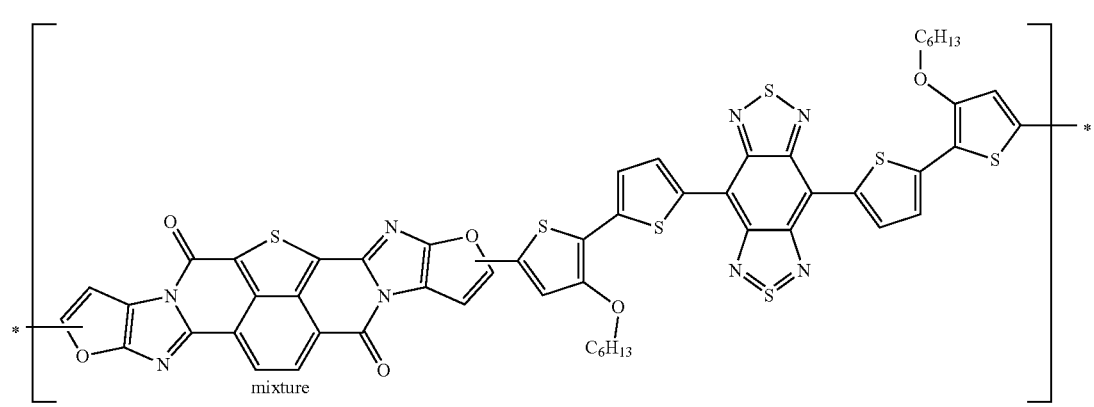
G-20
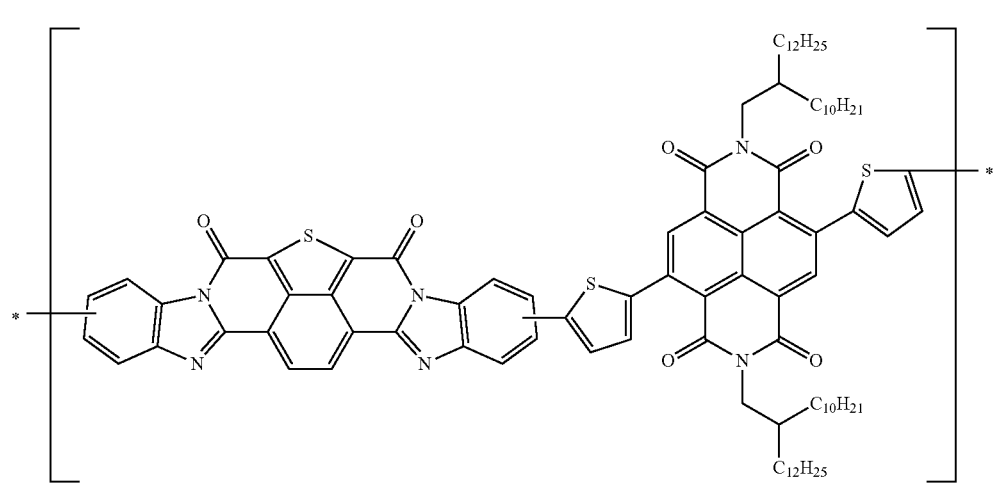
H-1

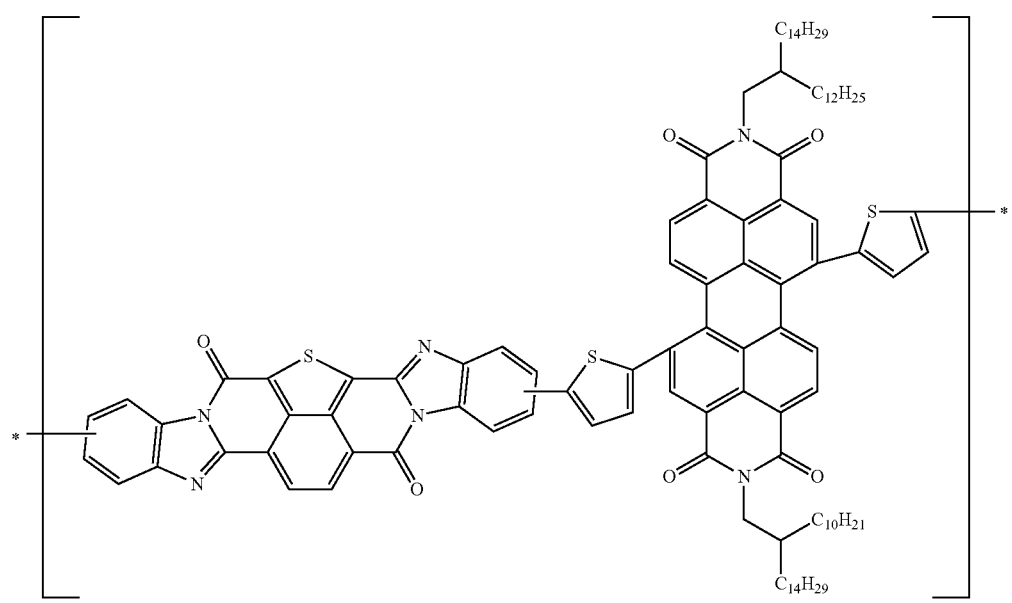
H-2
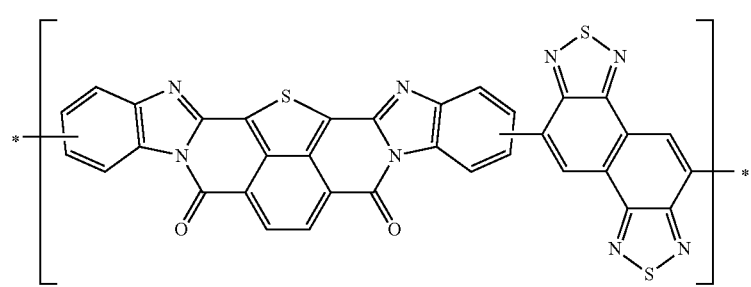
H-3
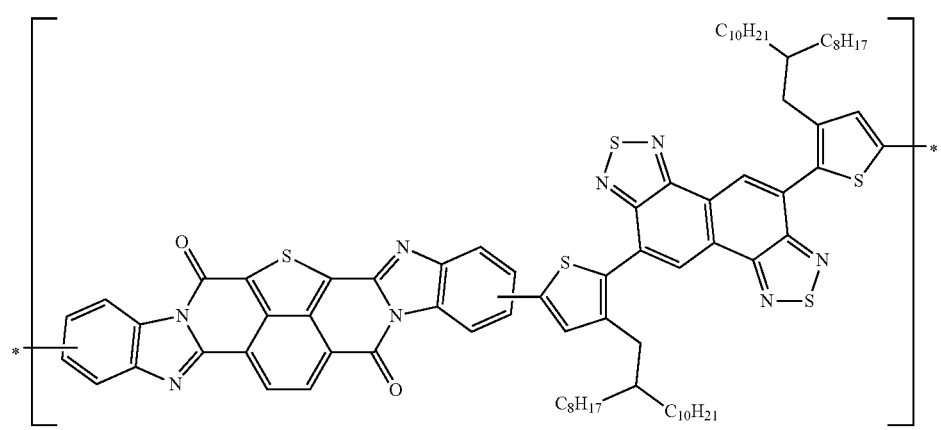
H-4
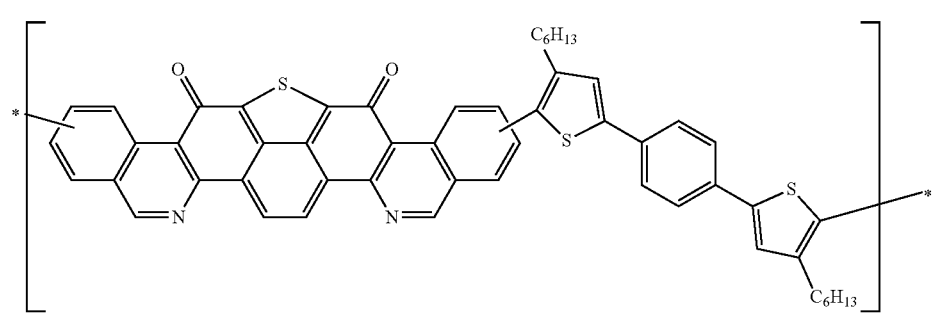
H-5

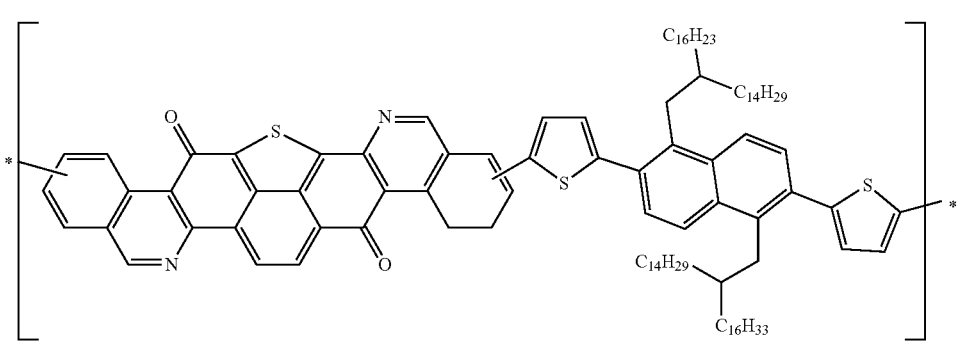
H-6
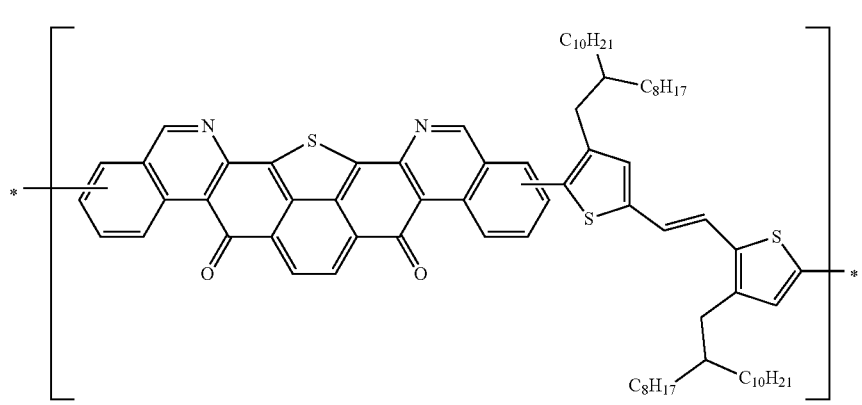
H-7
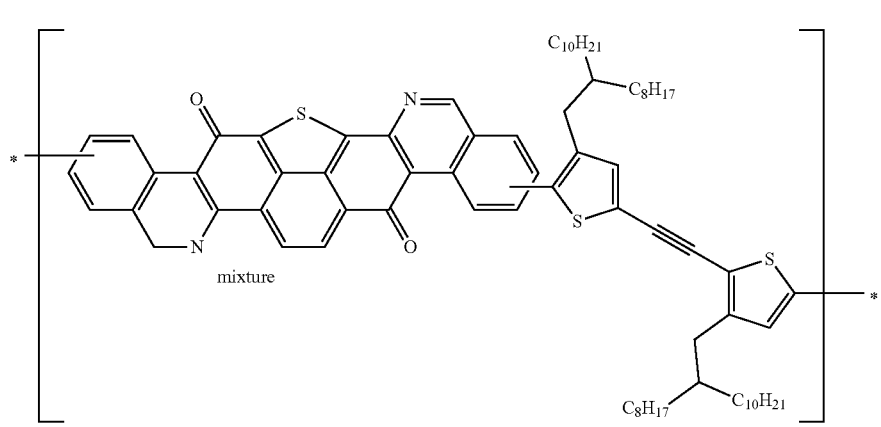
H-8
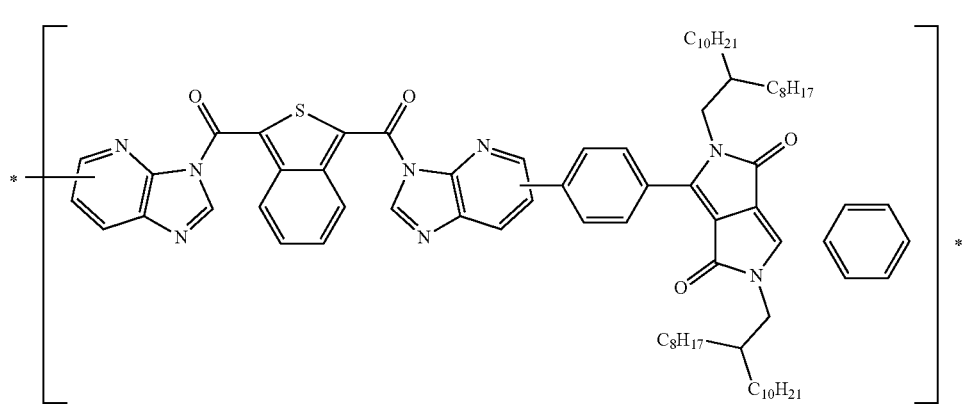
H-9

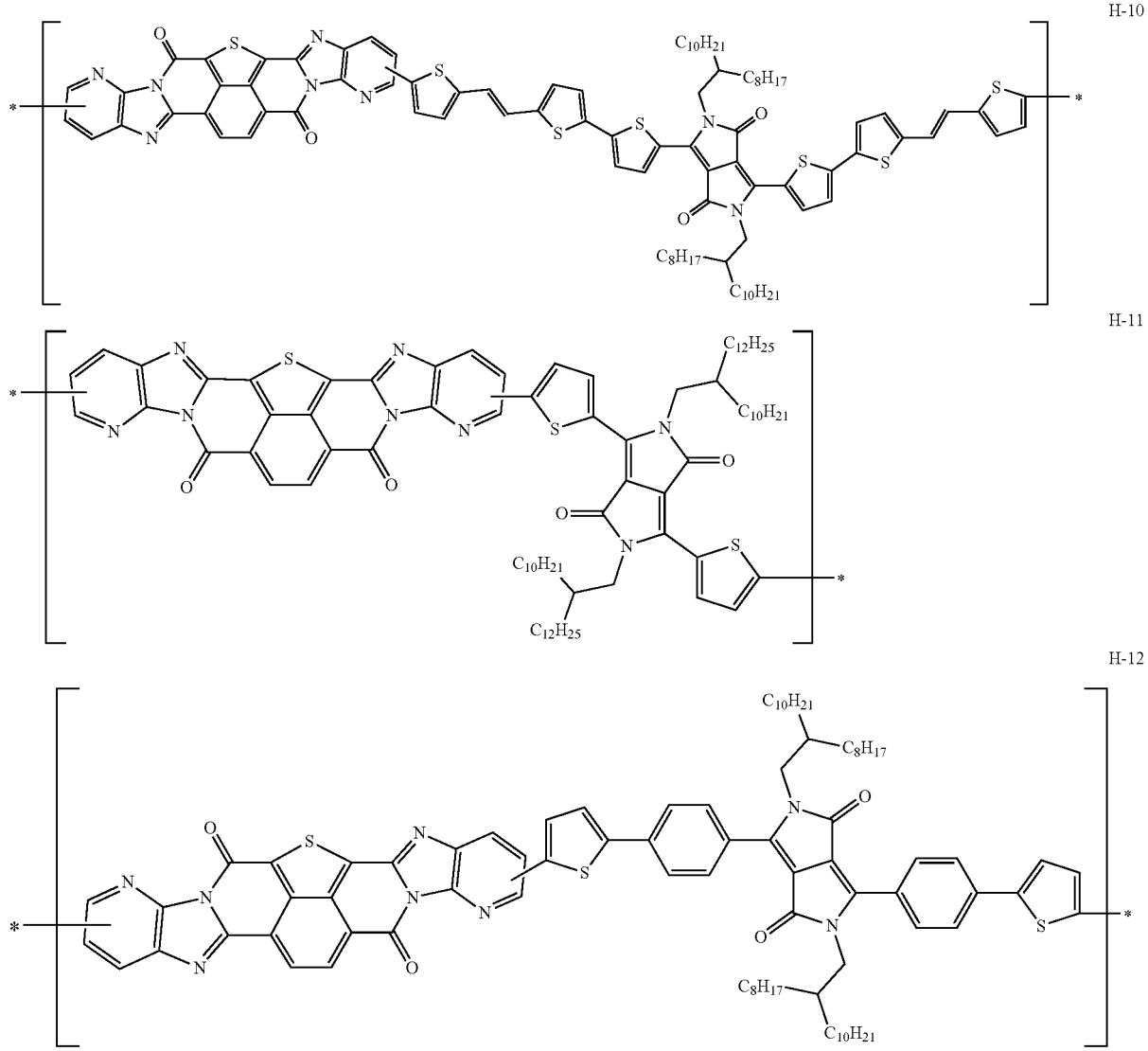

In a case where the organic semiconductor layer contains at least one compound represented by Formulae (1) to (3), the content of the compound represented by any one of Formulae (1) to (3) in the organic semiconductor layer is preferably 10 mass % or more, more preferably 30 mass % or more, and even more preferably 50 mass % or more in total. The total of the contents of the compounds represented by Formulae (1) to (3) in the organic semiconductor layer can be 100 mass %. In a case where the organic semiconductor film contains a binder or the like described below, for example, the total content is preferably 90 mass % or less and more preferably 80 mass % or less.

In a case where the organic semiconductor layer is an aspect of containing at least one structural unit represented by any one of Formulae (8) to (10), the content of the polymer having at least one structural unit represented by any one of Formulae (8) to (10) in the organic semiconductor layer is preferably 10 mass % or more, more preferably 30 mass % or more, and even more preferably 50 mass % or more in total. The total of the contents of the polymer having at least one structural unit represented by any one of Formulae (8) to (10) in the organic semiconductor layer can be 100 mass %. In a case where the organic semiconductor film contains a binder or the like described below, for example, the total content is preferably 90 mass % or less and more preferably 80 mass % or less.

A compound represented by any one of Formulae (1) to (3) and a polymer having at least one structural units represented by any one of Formulae (8) to (10) are collectively referred to as the "organic semiconductor used in the present invention".

In addition to the organic semiconductor used in the present invention, the organic semiconductor layer may contain a binder or an additive. As the additive, an additive that is generally used in the organic semiconductor layer may be used without particular limitation. The binder is described below.

(Binder)

As the binder, a binder that is generally used in the organic semiconductor layer may be used without particular limitation.

Examples of the binder include an insulating polymer such as polystyrene, poly(α-methylstyrene), polyvinylcinnamate, poly(4-divinylbenzene), poly(4-vinylphenol), poly(4-methylstyrene), polycarbonate, polyarylate, polyester, polyamide, polyimide, polyurethane, polysiloxane, polysulfone, polymethyl methacrylate, polymethyl acrylate, cellulose, polyethylene, or polypropylene, and copolymers thereof, a semiconductive polymer such as polysilane, polycarbazole, polyarylamine, polyfluorene, polythiophene, polypyrrole, polyaniline, polyparaphenylene vinylene, polyacene, or polyheteroacene, and copolymers thereof, rubber, and a thermoplastic elastomer.

Among these, a polymer compound having a benzene ring (polymer having a repeating unit having a benzene ring group) is preferable. The content of the repeating unit having a benzene ring group is not particularly limited, but is preferably 50 mol % or more, more preferably 70 mol % or more, and even more preferably 90 mol % or more with respect to the total repeating units. The upper limit is not particularly limited, but examples of the upper limit include 100 mol %.

The weight-average molecular weight of the binder is used as polymer is not particularly limited, and preferably 1,000 to 10,000,000, more preferably 3,000 to 5,000,000, and even more preferably 5,000 to 3,000,000.

The binder and the additive may be contained singly, and two or more kinds thereof may be contained, respectively.

The content of the binder in the organic semiconductor layer can be appropriately set without particular limitation. For example, the content is preferably 90 mass % or less, more preferably 70 mass % or less, and even more preferably 50 mass % or less. The content of the binder in the organic semiconductor layer can be 0 mass % or more, and for example, is preferably 10 mass % or more, more preferably 15 mass % or more, and even more preferably 20 mass % or more.

The content of the additive in the organic semiconductor layer is preferably 10 mass % or less, more preferably 5 mass % or less, and even more preferably 1 mass % or less.

The film thickness of the organic semiconductor layer can be appropriately adjusted depending on the applied organic semiconductor element, and for example, is preferably 10 to 500 nm and more preferably 20 to 200 nm.

(Method of Forming Organic Semiconductor Layer)

For example, the organic semiconductor layer can be formed by preparing a composition (hereinafter, also referred to as the "organic semiconductor composition of the present invention") obtained by dissolving the organic semiconductor used in the present invention in a solvent, coating the substrate with the composition, and depositing the organic semiconductor used in the present invention. More preferably, the substrate is coated with the organic semiconductor composition according to the embodiment of the present invention to form the coating film, and the coating film is dried to form the organic semiconductor layer. The organic semiconductor composition can contain a binder and/or an additive. The content of the binder and the additive in the organic semiconductor composition may be appropriately adjusted depending on the aspect of the organic semiconductor layer to be formed.

In the present invention, the expression "coating the substrate with the organic semiconductor composition" includes an aspect of applying the organic semiconductor composition over the substrate through another layer provided on the substrate, in addition to an aspect of directly the organic semiconductor composition to the substrate. Another layer (a layer that is in contact with an organic semiconductor layer and becomes a base of the organic semiconductor layer) to be coated with the organic semiconductor composition is inevitably determined according to the structure of the organic thin film transistor element. For example, in the case of a bottom gate type, the layer is a gate insulating film, and in the case of a top gate type (top gate-bottom contact type and top gate-top contact type), the layer is a source electrode or a drain electrode.

Well-known methods can be used as the coating method with the organic semiconductor composition, and examples thereof include a bar coating method, a spin coating method, a knife coating method, a doctor blade method, an ink jet printing method, a flexographic printing method, a gravure printing method, or a screen printing method. As the coating method with the organic semiconductor composition, a method (so-called gap cast method) of forming an organic semiconductor film disclosed in JP2013-207085A and a method (a so-called edge casting method and a continuous edge casting method) of manufacturing an organic semiconductor thin film disclosed in WO2014/175351 A and the like can be suitably applied.

In the drying (drying treatment), conditions can be appropriately selected according to the kind of each component included in the organic semiconductor composition. Although natural drying may be used, in view of improving productivity, a heat treatment is preferable. The heat treatment conditions cannot be definitively determined, but for example, the heating temperature is preferably 30° C. to 250° C., more preferably 40° C. to 200° C., and even more preferably 50° C. to 150° C., and the heating time is preferably 10 to 300 minutes and more preferably 20 to 180 minutes.

The method of preparing the organic semiconductor composition according to the present invention is not particularly limited, and a general preparation method may be employed. For example, it is possible to prepare the organic semiconductor composition of the present invention by adding respective components in a predetermined amount to the solvent and appropriately performing a stirring treatment.

The solvent is not particularly limited as long as the solvent dissolves or disperses the above polymer, and examples thereof include an inorganic solvent and an organic solvent. Among these, an organic solvent is preferable. The solvent may be used singly, and two or more kinds thereof may be used in combination.

The organic solvent is not particularly limited, and examples thereof include a hydrocarbon solvent such as hexane, octane, and decane, an aromatic hydrocarbon solvent such as toluene, xylene, mesitylene, ethylbenzene, decalin, 1-methylnaphthalene, tetralin, and anisole, a ketone solvent such as acetone, methyl ethyl ketone, methyl isobutyl ketone, and cyclohexanone, a halogenated hydrocarbon solvent such as dichloromethane, chloroform, tetrachloromethane, dichloroethane, trichloroethane, tetrachloroethane, chlorobenzene, dichlorobenzene, and chlorotoluene, an ester solvent such as ethyl acetate, butyl acetate, amyl acetate, and ethyl lactate, an alcohol solvent such as methanol, propanol, butanol, pentanol, hexanol, cyclohexanol, methyl cellosolve, ethyl cellosolve, and ethylene glycol, an ether solvent such as butoxybenzene, dibutyl ether, tetrahydrofuran, and dioxane, an amide solvent such as N,N-dimethylformamide and N,N-dimethylacetamide, an imide solvent such as 1-methyl-2-pyrrolidone and 1-methyl-2-imidazolidinone, a sulfoxide solvent such as dimethylsulfoxide, and a nitrile solvent such as acetonitrile.

The content ratio of the solvent in the organic semiconductor composition is preferably 90 to 99.99 mass %, more preferably 95 to 99.99 mass %, and even more preferably 96 to 99.95 mass %.

(Sealing Layer)

As described above, the organic semiconductor layer contains the organic semiconductor used in the present invention, and exhibits high heat resistance. Accordingly, even in a case where a heating step such as formation of a sealing layer or the like is performed after the organic semiconductor is provided, carrier mobility can be maintained at a desired level.

Accordingly, in view of durability, the organic thin transistor element according to the embodiment of the present invention preferably includes a sealing layer as an outermost layer. As a result, both of the excellent carrier mobility and the excellent durability can be sufficiently achieved.

For the sealing layer, a sealing agent (composition for forming a sealing layer) generally used for an organic TFT element can be used.

The sealing agent is preferably heated and dried to form a layer. The heating conditions at this point cannot be definitively determined, depending on the kind of the sealing agent and the like, but for example, the heating temperature is preferably 50° C. to 200° C., and more preferably 100° C. to 175° C. Other conditions such as the heating time are appropriately determined according to the kind of the sealing agent and the like.

The thickness of the sealing layer is not particularly limited but is preferably 0.2 to 10 μm.

—Bottom Gate-Top Contact-Type Organic Thin Film Transistor Element—

Figure 2:
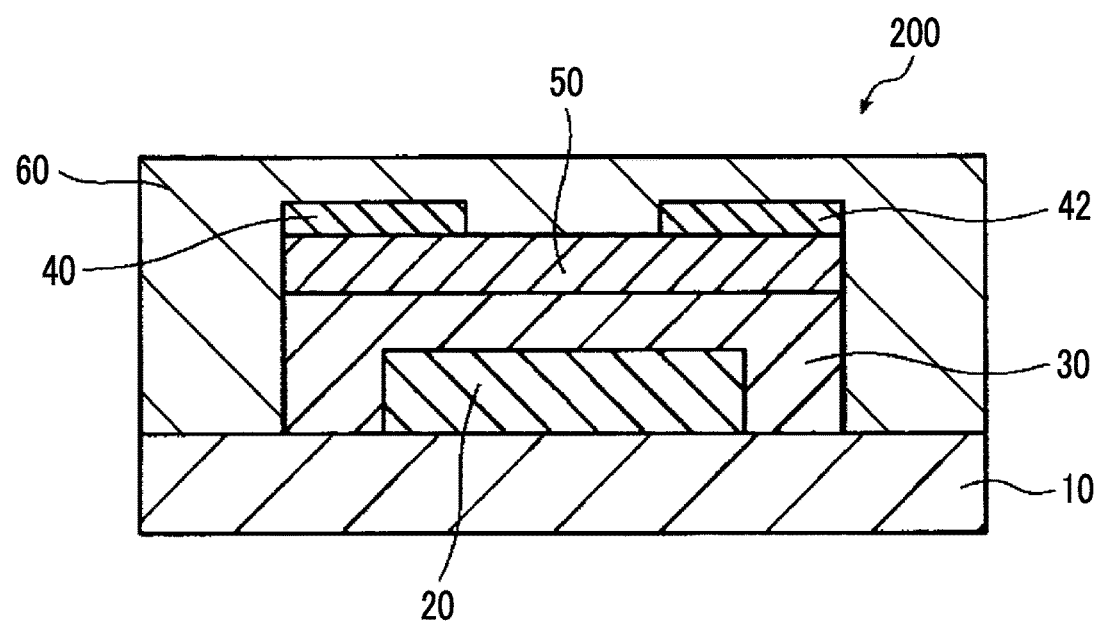
FIG. 2 is a cross-sectional schematic view illustrating a bottom gate-top contact-type organic thin film transistor element which is an example of the semiconductor element according to the embodiment of the present invention.

FIG. 2 is a cross-sectional schematic view indicating a bottom gate-top contact-type organic thin film transistor element 200 which is an example of the semiconductor element of the present invention.

As illustrated in FIG. 2, the organic thin film transistor element 200 has a base material 10, a gate electrode 20, a gate insulating film 30, a source electrode 40, a drain electrode 42, an organic semiconductor film 50, and a sealing layer 60.

The organic thin film transistor element 200 is the same as the organic thin film transistor element 100 except that the layer configuration (lamination aspect) is different. Accordingly, the substrate, the gate electrode, the gate insulating film, the source electrode, the drain electrode, the organic semiconductor layer, and the sealing layer are the same as those of the bottom gate-bottom contact-type organic thin film transistor element, and thus descriptions thereof are omitted.

EXAMPLES

The present invention is more specifically described based on the examples, according to the present invention is not limited to the following examples. In the present examples, Et represents ethyl, Me represents methyl, Ph represents phenyl, Bu represents butyl, TMEDA represents tetramethylethylenediamine, Ac represents acetyl, and Cp represents cyclopentadienyl. Also, DMF represents N,N-dimethylformamide, THF represents tetrahydrofuran, DMSO represents dimethylsulfoxide, NBS represents N-bromosuccinimide, NMP represents N-methyl-2-pyrrolidone, DME represents dimethylether, and TBAF represents tetrabutylammonium fluoride.

Synthesis of Intermediate 1

J. Mater. Chem., 2012, Book 22, p. 23514, Org. Lett. 2012, Book 14, p. 3100, and the like were referred to, and according to Scheme 1, an intermediate 1 (3.4 g, 12.4 mmol) was obtained from a compound 1-1 (20 g, 115 mmol).

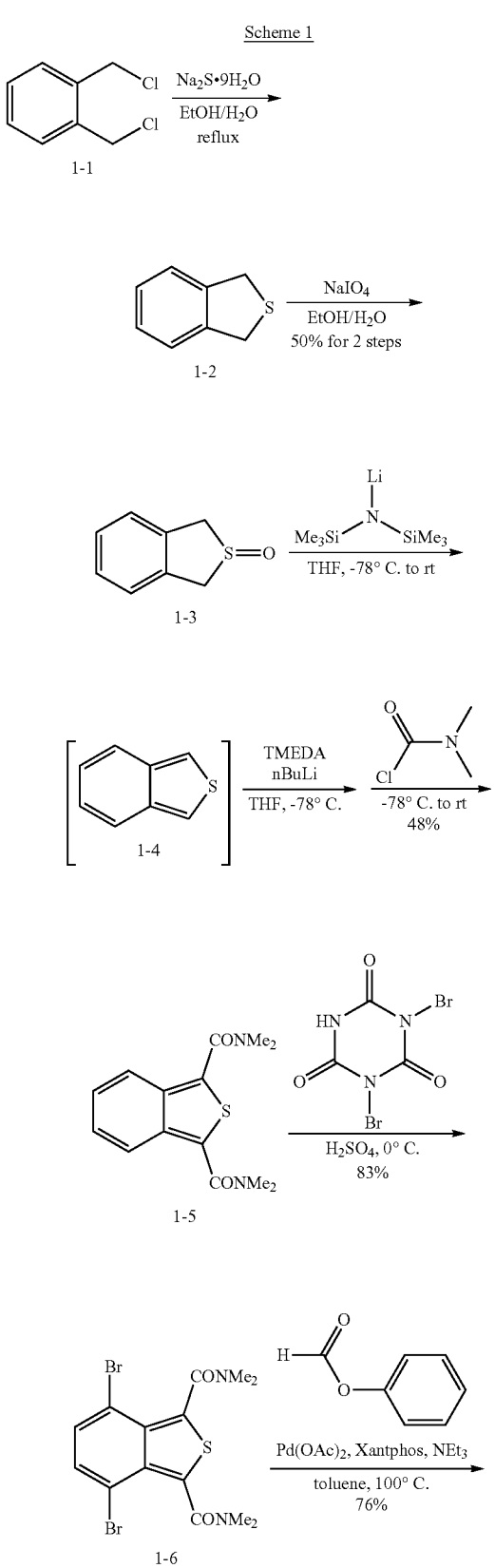

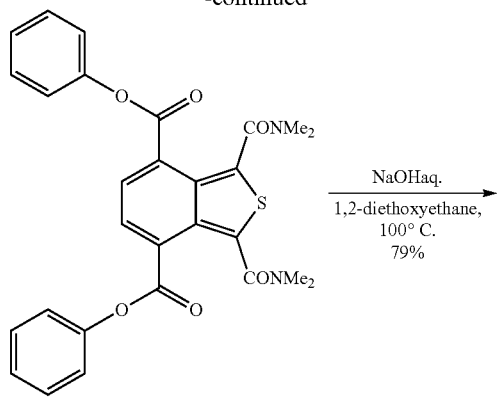
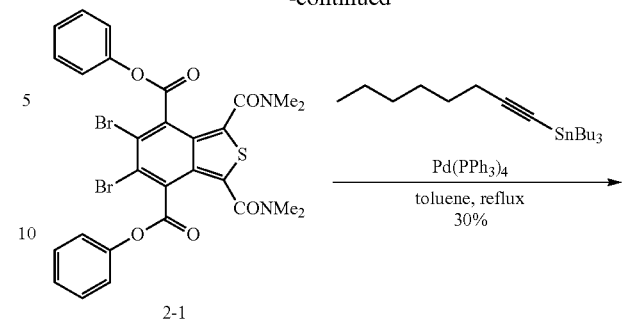
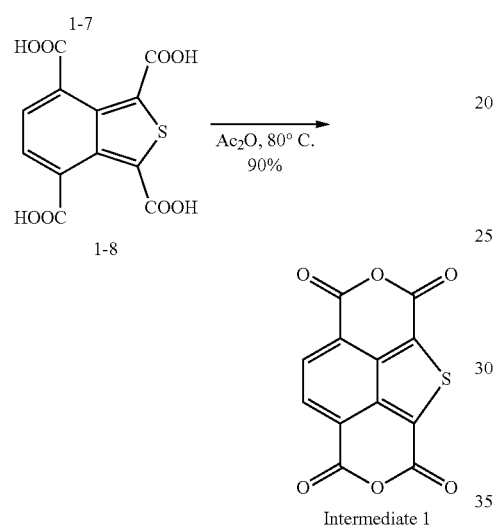
Synthesis of Intermediate 2
Tetrahedron Letters, 2013, Book 54, p. 3171 and the like was referred to, to obtain an intermediate 2 (573 mg, 1.15 mmol) and the like, from a compound 1-7 (5.0 g, 9.68 mmol) according to Scheme 2.
In Scheme 2, Ph represents phenyl, and rt is 25° C.
Scheme 2
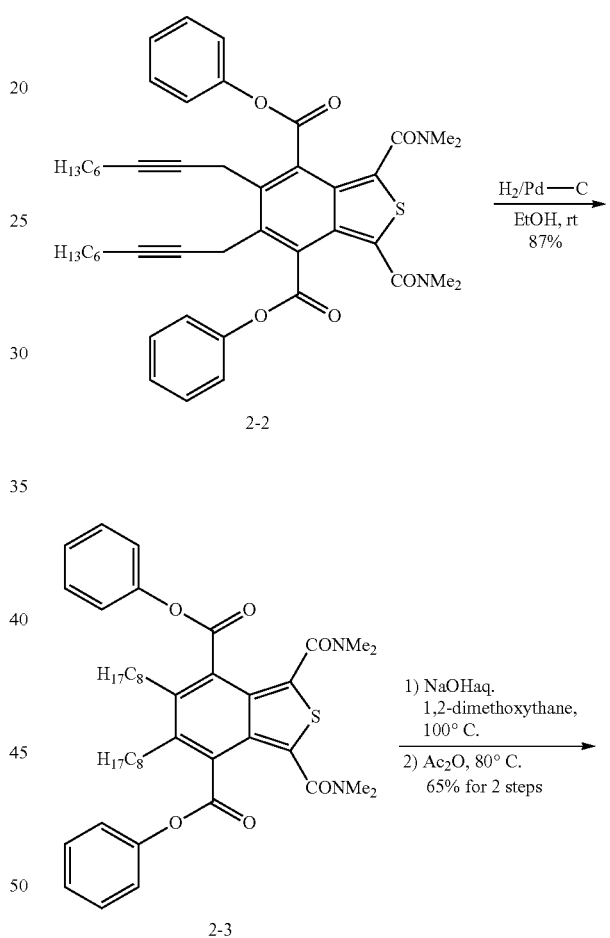
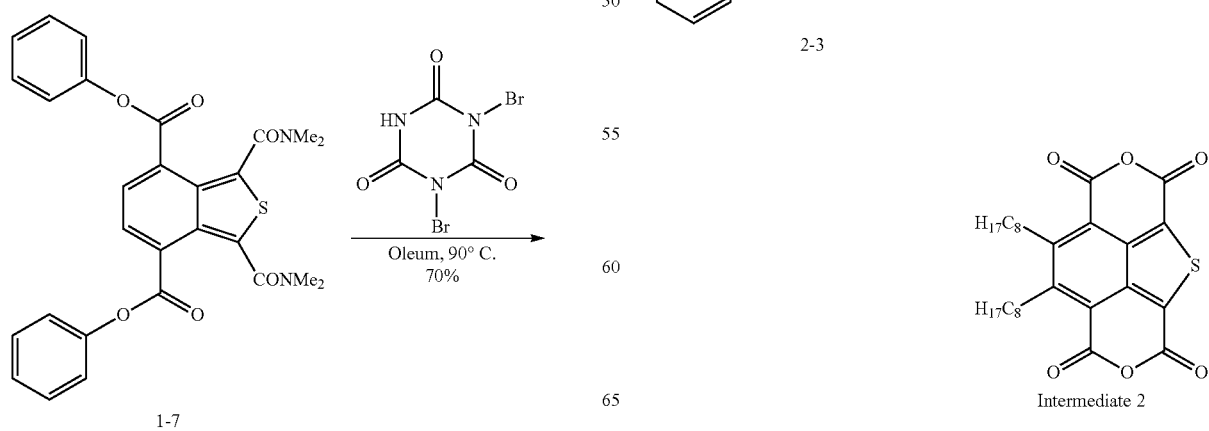

Synthesis of Compounds 3-8 to 3-10

J. Org. Chem. 1988, Book 53, p. 3978, and the like were referred to, and according to Scheme 3, a compound 3-8 (344 mg, 0.800 mmol), a compound 3-9 (413 mg, 0.960 mmol), and a compound 3-10 (310 mg, 0.720 mmol) were synthesized from the intermediate 1 (2 g, 7.29 mmol). The compounds 3-8, 3-9, and 3-10 were separated by silica gel column chromatography.

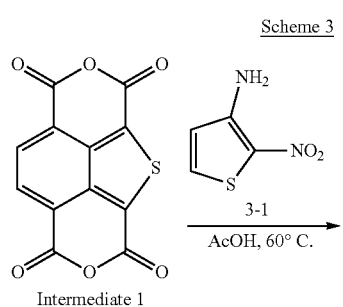

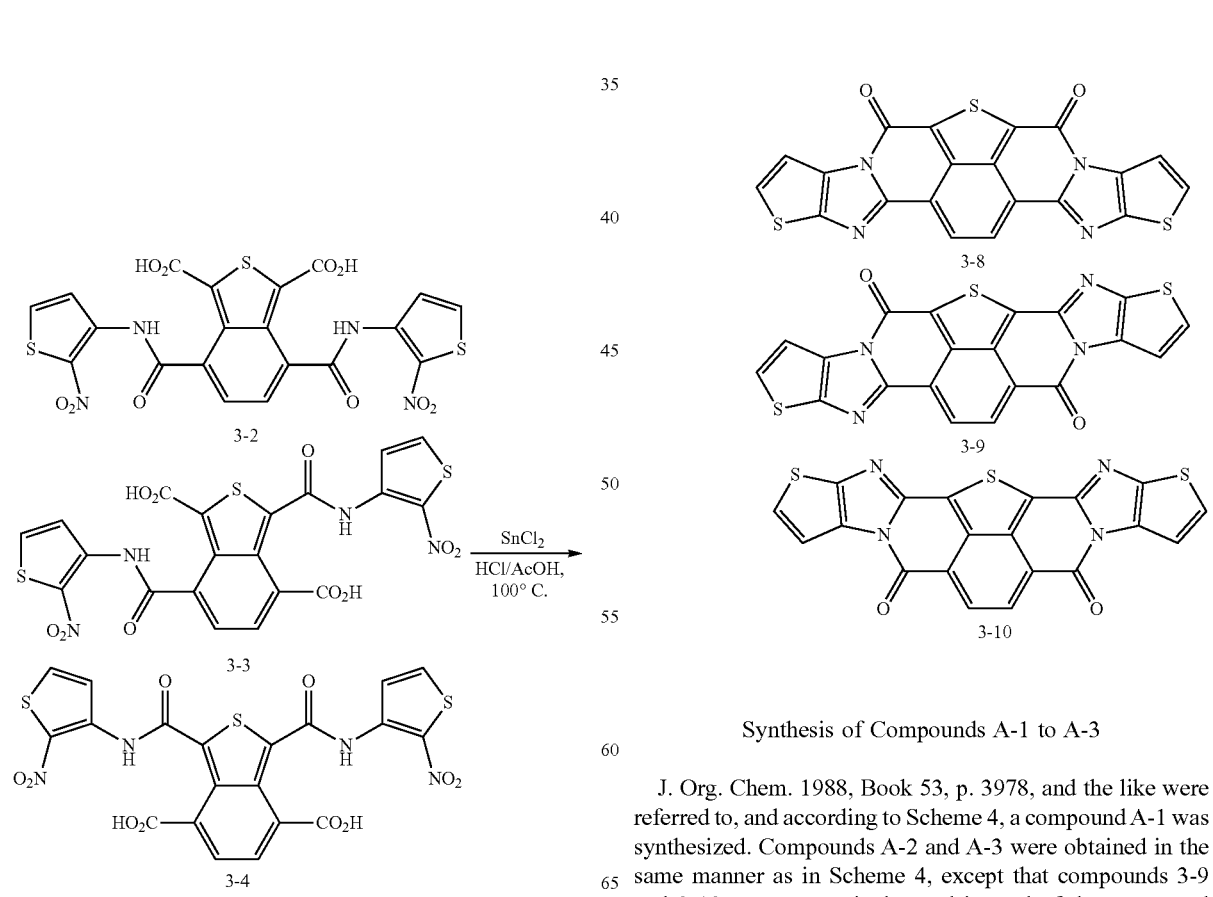

Synthesis of Compounds A-1 to A-3

J. Org. Chem. 1988, Book 53, p. 3978, and the like were referred to, and according to Scheme 4, a compound A-1 was synthesized. Compounds A-2 and A-3 were obtained in the same manner as in Scheme 4, except that compounds 3-9 and 3-10 were respectively used instead of the compound 3-8.

Scheme 4

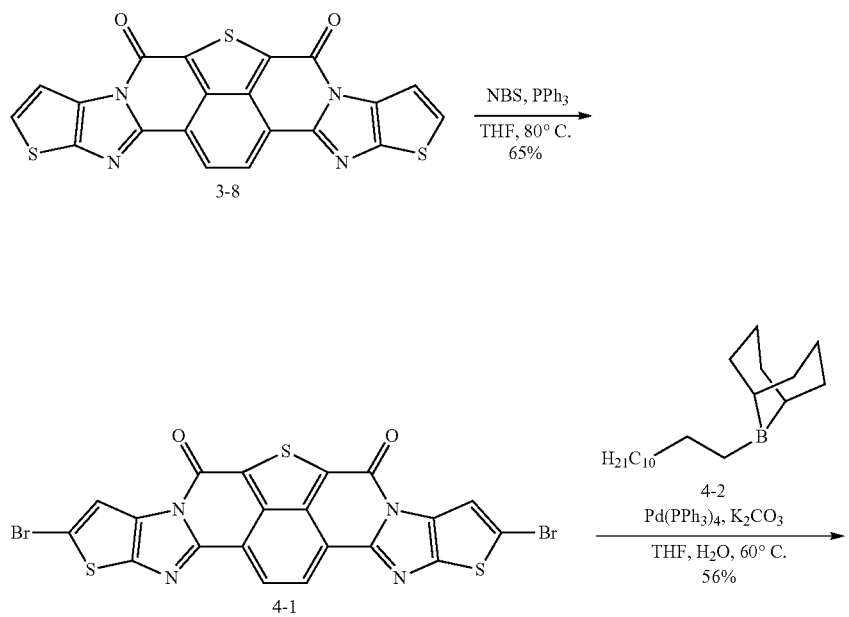

Synthesis of Compound A-4

A compound A-4 was obtained in the same manner as in Schemes 3 and 4, except that an intermediate 2 was used instead of the intermediate 1.

Synthesis of Compound A-5

Chem. Pharm. Bull. 1995, Book 43, p. 162, and the like were referred to, and according to Scheme 5, a compound 5-3 was synthesized.

Scheme 5

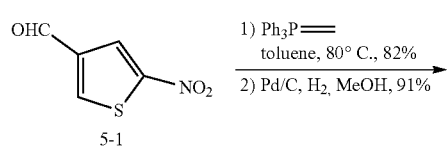

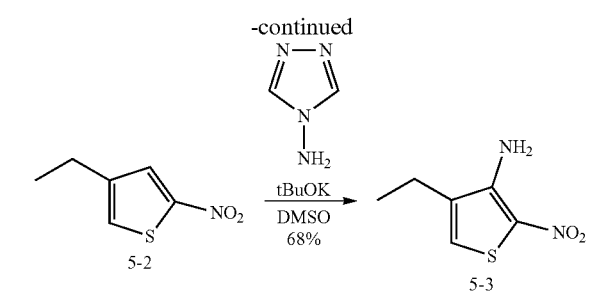

A compound A-5 was obtained in the same manner as in Schemes 3 and 4, except that the compound 5-3 was used instead of the compound 3-1. The isomers were separated by silica gel column chromatography.

Synthesis of Compound A-6

Tetrahedron Letters, 2013, Book 54, p. 7103, and the like were referred to, and according to Scheme 6, a compound A-6 (74.8 mg, 0.0936 mmol) was obtained from a compound A-1 (100 mg, 0.130 mmol).

Scheme 6

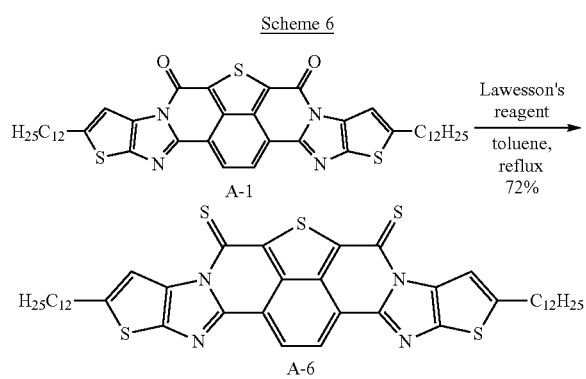

Synthesis of Compound A-7

According to Scheme 7, a compound A-7 (93.6 mg, 0.118 mmol) was obtained from the compound A-1 (100 mg, 0.153 mmol).

Scheme 7

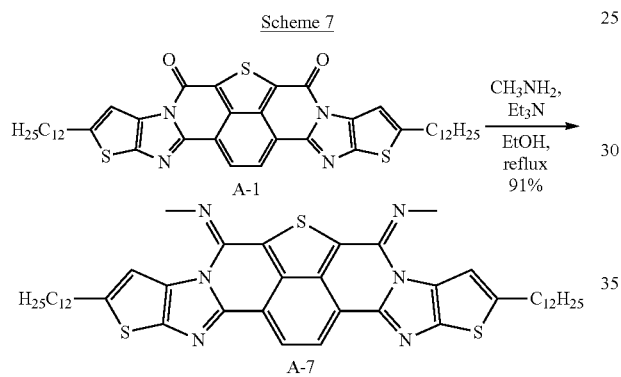

Synthesis of Compound A-8

Tetrahedron Letters, 1995, Book 36, p. 2393, and the like were referred to, and according to Scheme 8, a compound A-8 (44.6 mg, 0.0585 mmol) was synthesized from the compound A-1 (100 mg, 0.130 mmol).

Scheme 8

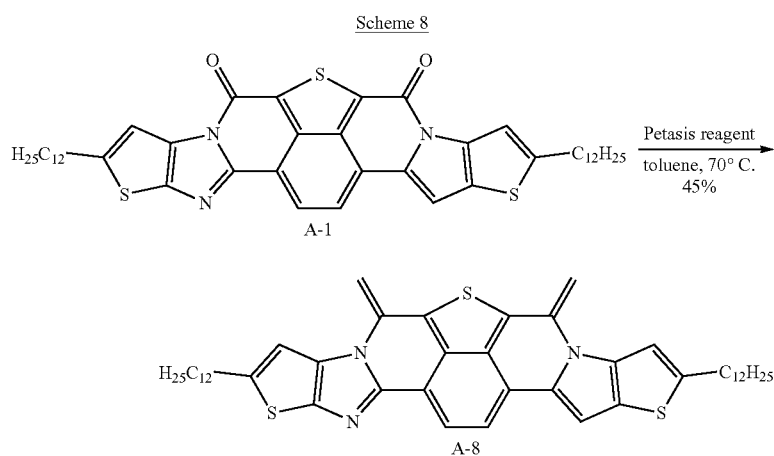

Synthesis of Compounds A-9 to A-11

Compounds A-9, A-10, and A-11 were obtained in the same manner as in the above scheme, except that compounds 6-1, 6-2, and 6-3 disclosed in Tetrahedron Letters, 1990, Book 31, p. 3155, Org. Lett. 2003, Book 5, p. 2519, or J. Am. Chem. Soc. 2009, Book 131, p. 6070 were respectively used instead of the compound 1-4. The isomers were separated by silica gel column chromatography.

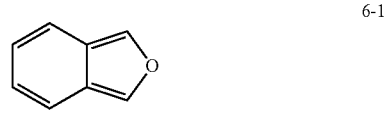

Synthesis of Compound A-12

Tetrahedron Letters 2014, Book 55, p. 795, and J. Heterocycl. Chem. 1990, Book 27, p. 1007, and the like were referred to, and according to Scheme 9, a compound A-12 (129 mg, 0.166 mmol) was obtained from the compound 7-2 (1 g, 2.83 mmol).

Scheme 9
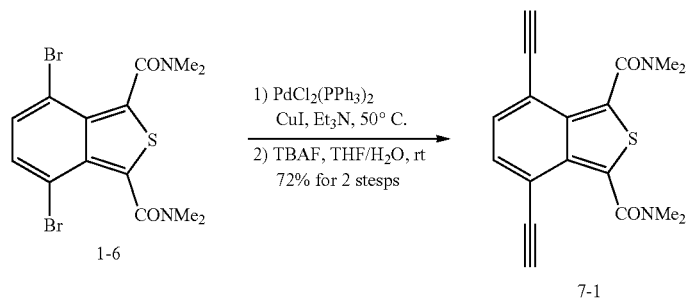
1-6
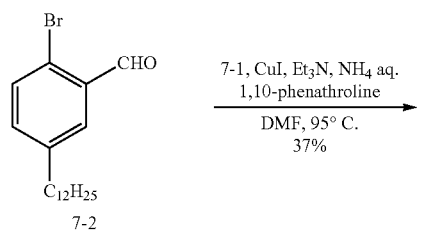
7-2
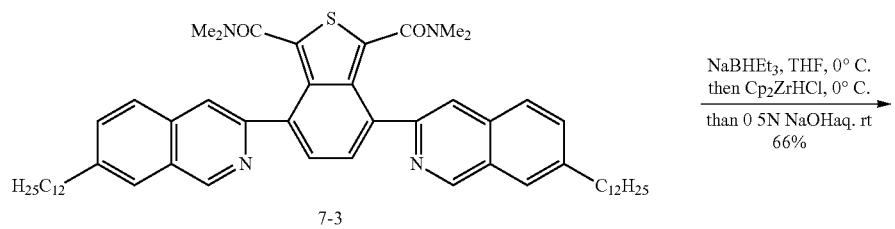
7-3
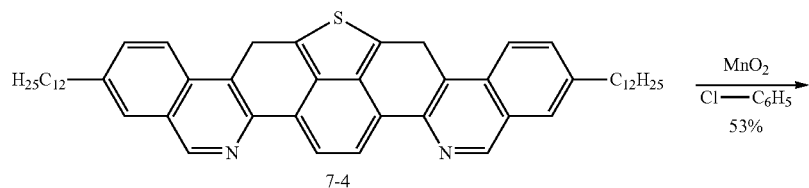
7-4
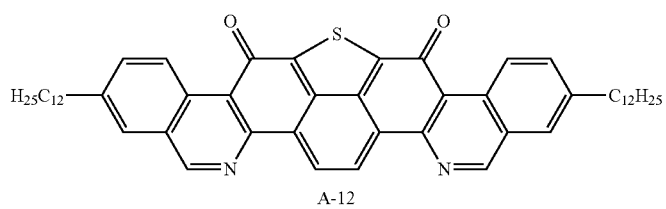
A-12

Synthesis of Compound A-13

Org. Lett. 2009, Book 11, p. 2679, Catal Commun, 2012, Book 27, p. 30, and the like were referred to, and according to Scheme 10, a compound A-13 (252 mg, 0.373 mmol) was obtained from the compound 8-1 (1 g, 4.04 mmol).

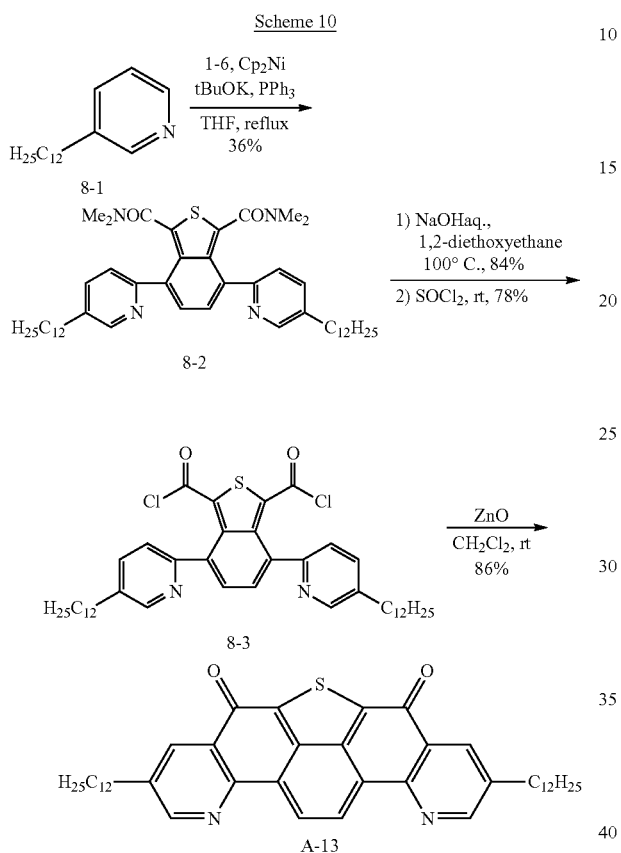

Synthesis of Compound A-14

J. Am. Chem. Soc. 2003, Book 125, p. 5274, and the like were referred to, and according to Scheme 11, a compound A-14 (402 mg, 0.614 mmol) was obtained from a compound 9-1 (1 g, 4.23 mmol).

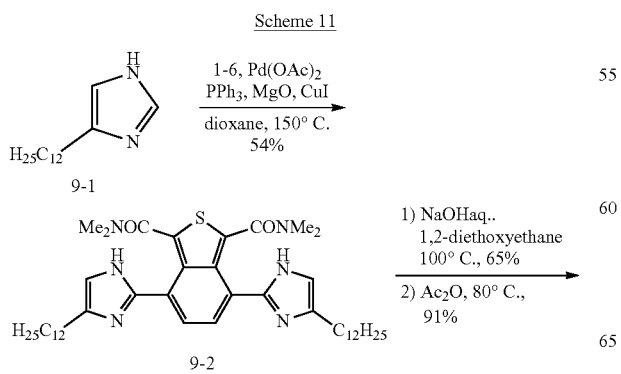

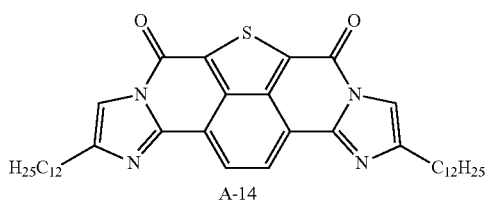

Synthesis of Compounds A-15 to A-17

Compounds A-15, A-16, and A-17 were obtained in the same manner as in Schemes 3 and 4, except that compounds 10-1, 10-2, and 10-3 were respectively used instead of the compound 3-1.

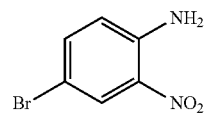

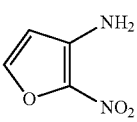

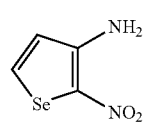

Synthesis of Compounds A-18 to A-26

Compounds A-18 to A-26 were obtained in the same manner as in Scheme 4, except that raw materials corresponding to the compounds A-18 to A-26 were respectively used instead of the compound 4-2. The isomers were separated by silica gel column chromatography.

Synthesis of Compound A-27

A compound A-27 was obtained in the same manner as in Schemes 3 and 4, except that the compound 11-1 was used instead of the compound 3-1. The isomers were separated by silica gel column chromatography.

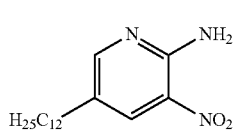

Comparative Synthesis Example 1
Comparative compounds 1 and 2 were synthesized according to the following scheme.
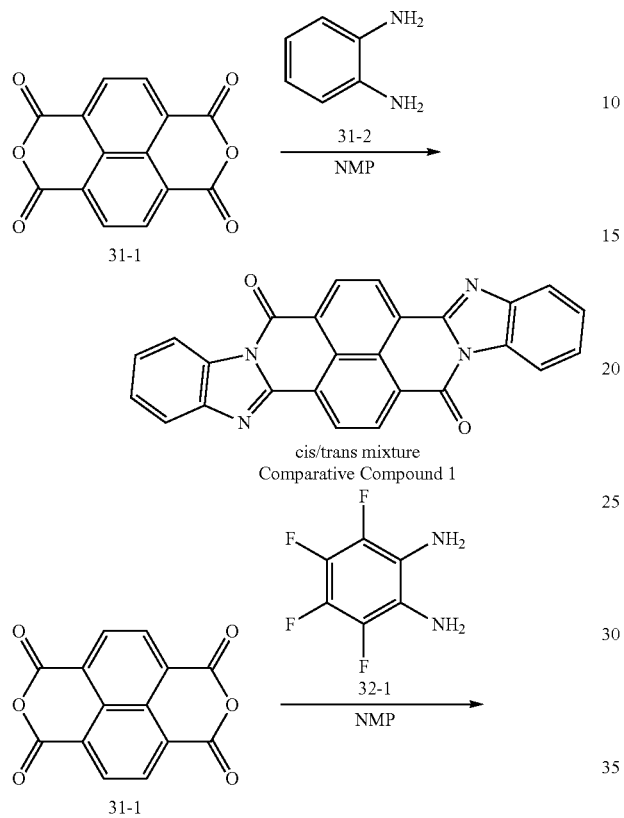
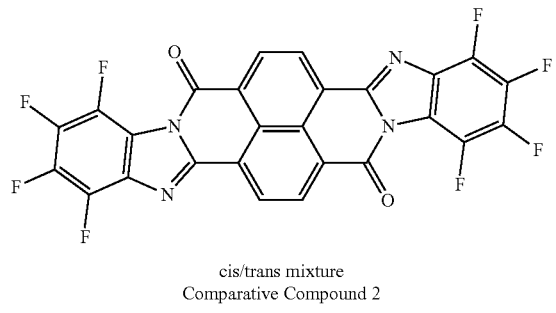
Structures of the obtained compound A-1 to A-27 and the obtained comparative compounds 1 and 2 are provided below.
A-1
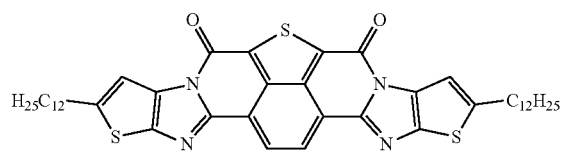
A-2
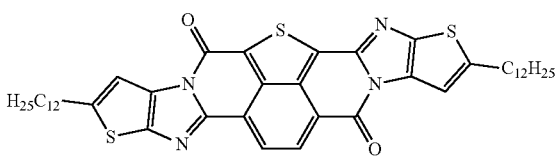
A-3
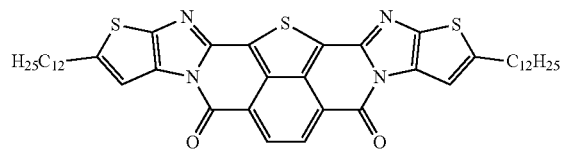
A-4
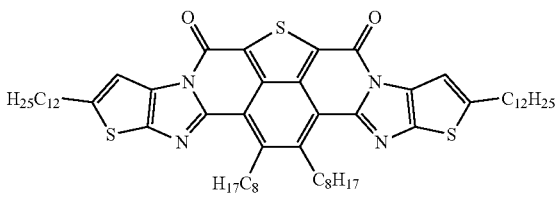
A-5
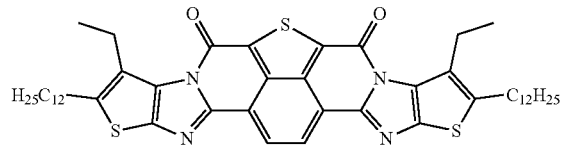
A-6
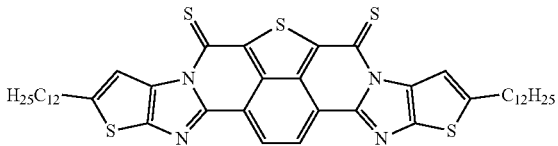

-continued
A-7
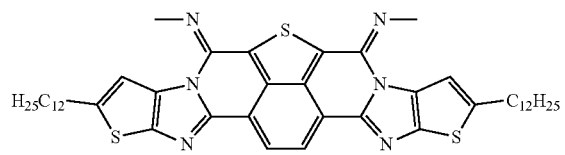
A-8
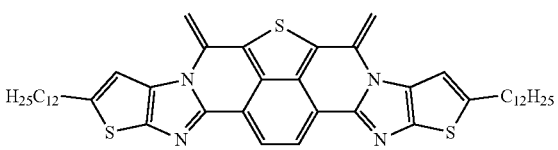
A-9
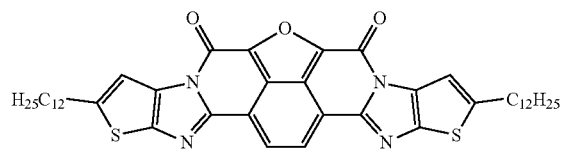
A-10
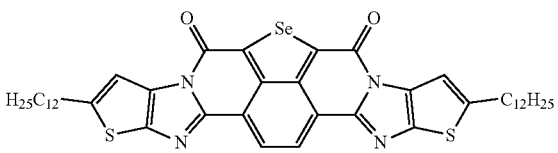
A-11
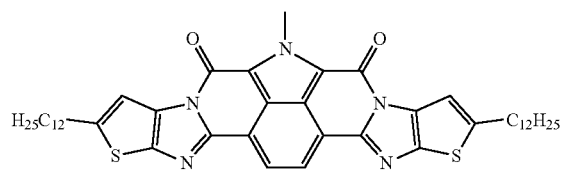
A-12
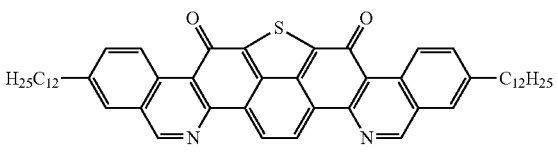
A-13
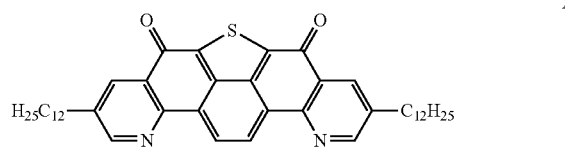
A-14
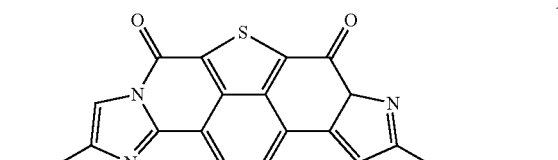
A-15
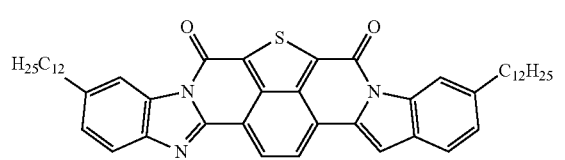
A-16
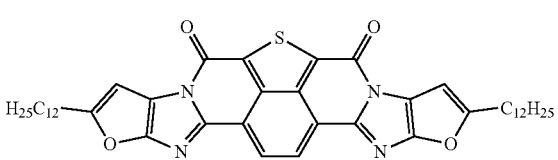
A-17
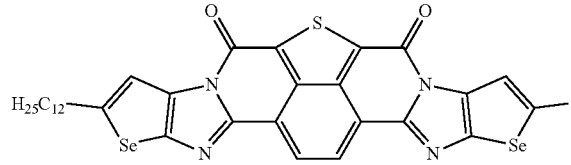
A-18
A-19
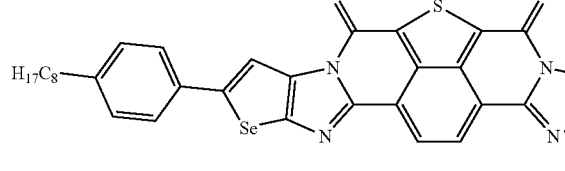
A-20
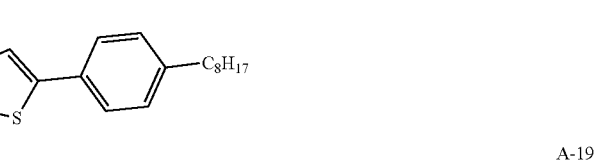
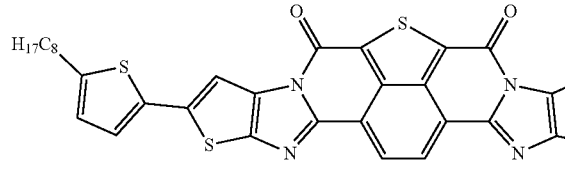

-continued
A-21
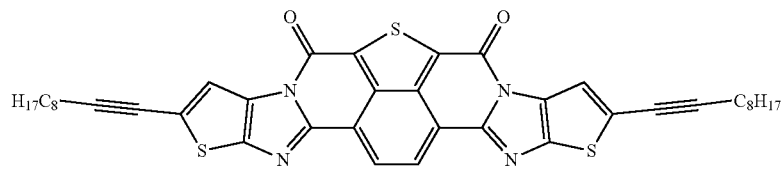
A-22
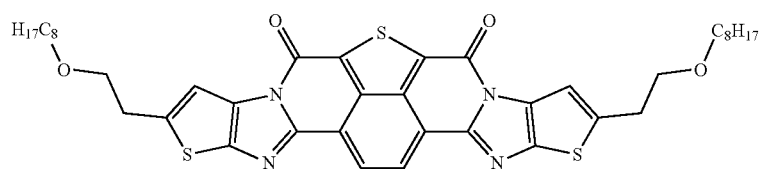
A-23
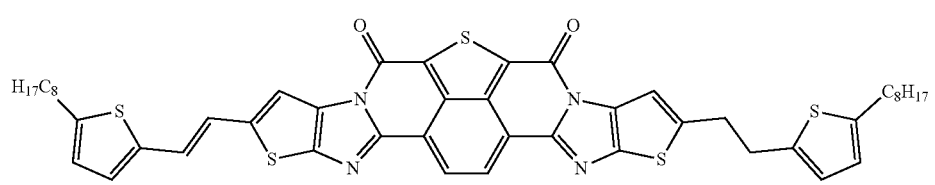
A-24
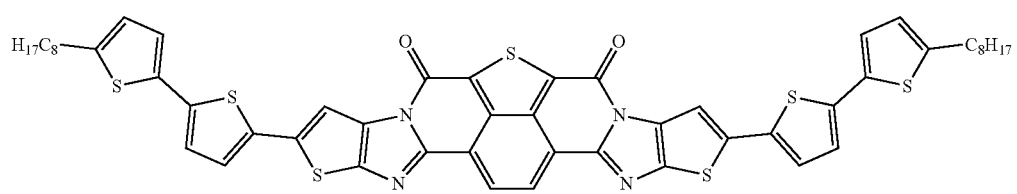
A-25
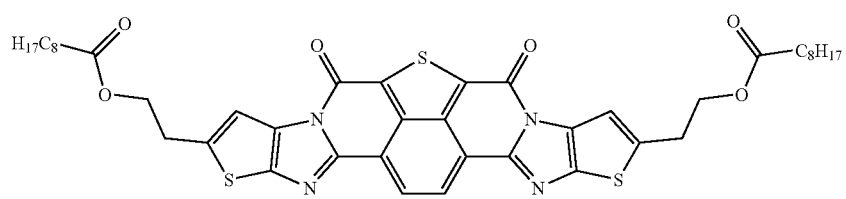
A-26
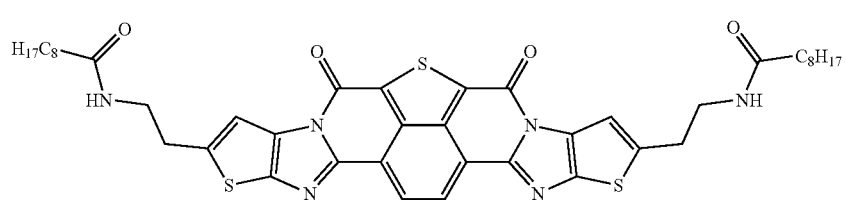
A-27
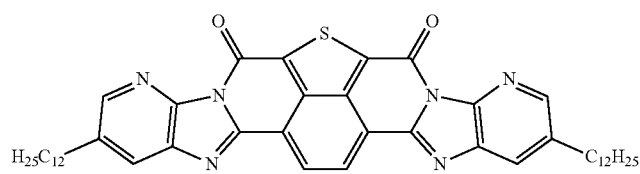

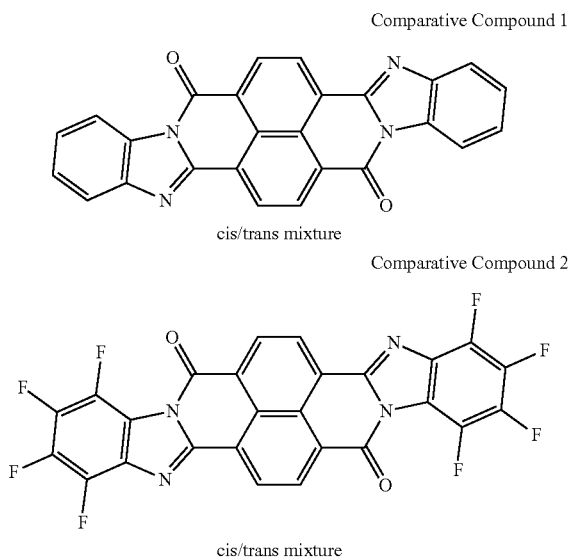

Comparative Compound 1 cis/trans mixture

Comparative Compound 2 cis/trans mixture

Each of the above organic semiconductor compounds and comparative compounds was examined for purity (area ratio of absorption strength at 254 nm) by high performance liquid chromatography (TSKgel ODS-100Z manufactured by Tosoh Corporation), and the purity was 99.0% or more.

[Manufacturing of Bottom Gate-Top Contact Element by Vapor Deposition Process]

A surface of a 10 mm×10 mm substrate on the thermal oxide film side in which a SiO 2 thermal oxide film of 500 nm was formed on the surface of an n-type silicon substrate (having a thickness of 0.4 mm) was subjected to ultraviolet light (UV)-ozone cleaning and was treated with β-phenytillymethoxysilane.

Films were formed on the β-phenylitylmethoxysilane-treated surface of this substrate by vapor deposition with the compounds presented in the following table at a deposition rate of 0.05 nm/s so as to have a film thickness of 40 nm.

By attaching a mask on the obtained organic semiconductor film and performing vapor deposition of 2 nm of F4-TCNQ and 40 nm of a gold electrode as a charge injection acceptor, organic thin film transistor elements 1-1 to 1-31 (hereinafter, also referred to as "elements 1-1 to 1-31") for FET characteristic measurement, and comparative organic thin film transistor elements 1-1 and 1-2 (hereinafter, also referred to as "comparative elements 1-1 and 1-2") were obtained.

[Evaluation of Carrier Mobility]

With respect to the FET characteristic of each organic thin film transistor element (elements 1-1 to 1-31 and comparative elements 1-1 and 1-2), the carrier mobility under atmospheric pressure was evaluated by using a semiconductor parameter analyzer (4156C manufactured by Agilent Technologies, Inc.) connected to a semi-auto prober (AX-2000 manufactured by Vector Semiconductor Co., Ltd.).

The carrier mobility μ was obtained by applying a voltage of −50 V between the source electrode and the drain electrode of each organic thin film transistor element (FET element), changing the gate voltage in the range of 20 V to −150 V, and using an expression $I_d=(W/2\,L)\mu C_i(V_g-V_{th})^2$ (in the expression, L represents a gate length, W represents a gate width, $C_i$ represents a capacitance per unit area of an insulating layer, $V_g$ represents a gate voltage, and $V_{th}$ represents a threshold voltage) representing drain current $I_d$, and was evaluated by the following evaluation standards.

—Evaluation of Carrier Mobility—

AA: 1.0 cm²/Vs or more
A: 0.8 cm²/Vs or more and less than 1.0 cm²/Vs
B: 0.6 cm²/Vs or more and less than 0.8 cm²/Vs
C: 0.4 cm²/Vs or more and less than 0.6 cm²/Vs
D: 0.2 cm²/Vs or more and less than 0.4 cm²/Vs
E: 0.1 cm/Vs or more and less than 0.2 cm²/Vs
F: 0.05 cm²/Vs or more and less than 0.1 cm²/Vs
G: Less than 0.05 cm²/Vs The results thereof are presented in the following table.

[Evaluation of Heat Resistance]

Each of the elements 1-1 to 1-31 and the comparative elements 1-1 and 1-2 was heated at 150° C. for 30 minutes in the atmosphere, and then the carrier mobility was evaluated in the same manner as described above. A maintenance rate (%) of the carrier mobility was calculated by applying the carrier mobility before and after heating to the following equation.

Maintenance rate (%) of carrier mobility=100×{carrier mobility(after heating)/carrier mobility(before heating)}

The maintenance rate of the carrier mobility was applied to the following evaluation standards to evaluate the heat resistance.

—Evaluation Standard of Maintenance Rate of Carrier Mobility (Heat Resistance)—

AA: The maintenance rate of the carrier mobility was 90% or more
A: The maintenance rate of the carrier mobility was 80% or more and less than 90%
B: The maintenance rate of the carrier mobility was 70% or more and less than 80%
C: The maintenance rate of the carrier mobility was 60% or more and less than 70%
D: The maintenance rate of the carrier mobility was 50% or more and less than 60%
E: The maintenance rate of the carrier mobility was 40% or more and less than 50%
F: The maintenance rate of the carrier mobility was 30% or more and less than 40%
G: The maintenance rate of the carrier mobility was less than 30%

The results thereof are presented in the following table.

TABLE 1

| | Element No. | Compound in organic semiconductor layer | Carrier mobility | Heat resistance |
|---|---|---|---|---|
| Example 1-1 | Element 1-1 | A-1 | AA | AA |
| Example 1-2 | Element 1-2 | A-2 | AA | AA |
| Example 1-3 | Element 1-3 | A-3 | AA | AA |
| Example 1-4 | Element 1-4 | A-1/A-2 = 1/1 (Mass ratio) | AA | AA |
| Example 1-5 | Element 1-5 | A-2/A-3 = 1/1 (Mass ratio) | AA | AA |

TABLE 1-continued

| | Element No. | Compound in organic semiconductor layer | Carrier mobility | Heat resistance |
|---|---|---|---|---|
| Example 1-6 | Element 1-6 | A-1/A-3 = 1/1 (Mass ratio) | AA | AA |
| Example 1-7 | Element 1-7 | A-1/A-2/A-3 = 1/1/1 (Mass ratio) | AA | AA |
| Example 1-8 | Element 1-8 | A-4 | AA | AA |
| Example 1-9 | Element 1-9 | A-5 | AA | AA |
| Example 1-10 | Element 1-10 | A-6 | AA | AA |
| Example 1-11 | Element 1-11 | A-7 | E | E |
| Example 1-12 | Element 1-12 | A-8 | E | E |
| Example 1-13 | Element 1-13 | A-9 | AA | AA |
| Example 1-14 | Element 1-14 | A-10 | AA | AA |
| Example 1-15 | Element 1-15 | A-11 | AA | AA |
| Example 1-16 | Element 1-16 | A-12 | B | B |
| Example 1-17 | Element 1-17 | A-13 | D | D |
| Example 1-18 | Element 1-18 | A-14 | D | D |
| Example 1-19 | Element 1-19 | A-15 | B | A |
| Example 1-20 | Element 1-20 | A-16 | AA | AA |
| Example 1-21 | Element 1-21 | A-17 | AA | AA |
| Example 1-22 | Element 1-22 | A-18 | AA | AA |
| Example 1-23 | Element 1-23 | A-19 | AA | AA |
| Example 1-24 | Element 1-24 | A-20 | AA | AA |
| Example 1-25 | Element 1-25 | A-21 | AA | AA |
| Example 1-26 | Element 1-26 | A-22 | AA | AA |
| Example 1-27 | Element 1-27 | A-23 | AA | AA |
| Example 1-28 | Element 1-28 | A-24 | AA | AA |
| Example 1-29 | Element 1-29 | A-25 | A | A |
| Example 1-30 | Element 1-30 | A-26 | A | A |
| Example 1-31 | Element 1-31 | A-27 | C | C |
| Comparative Example 1-1 | Comparative element 1-1 | Comparative compound 1 | G | G |
| Comparative Example 1-2 | Comparative element 1-2 | Comparative compound 2 | G | G |

As presented in Table 1, even in a case where the organic semiconductor layer was an element including a compound having a fused polycyclic structure, in a case where the structure of the compound was out of the range determined in the present invention, the carrier mobility was inferior, and the heat resistance, as a result (Comparative Examples 1-1 and 1-2).

Meanwhile, it is understood that an element in which a compound having a structure determined in the present invention was used for the organic semiconductor layer had excellent carrier mobility and also excellent heat resistance (Examples 1-1 to 1-31).

[Preparation of Organic Semiconductor Composition]

Each compound presented in the following table, a composition obtained by mixing poly α-methylstyrene at a mass ratio of 1:1, and toluene as a solvent were mixed to prepare a solution (organic semiconductor composition) containing a compound at a concentration of 0.1 mass %. This solution was heated to 40° C. and used to form the following element.

[Manufacturing of Bottom Gate-Bottom Contact Element Using Polymer Binder]

By casting (drop cast method) the organic semiconductor composition prepared above on a substrate for the field effect transistor (FET) characteristic measurement heated to 40° C. in a nitrogen atmosphere, the organic thin film transistor elements 2-1 to 2-31 (hereinafter, referred to "elements 2-1 to 2-31"), and comparative organic thin film transistor elements 2-1 and 2-2 (hereinafter, also referred to as "comparative elements 2-1 and 2-2") were obtained.

As the substrate for FET characteristic measurement, a silicon substrate having a bottom gate and bottom contact structure comprising chromium/gold (gate width W=100 mm, gate length L=100 m) disposed in a comb shape as source and drain electrodes and $SiO_2$ (film thickness of 500 nm) as an insulating film was used.

The carrier mobility and the heat resistance of each of the obtained elements were evaluated in the same manner as described above.

TABLE 2

| | Element No. | Compound in organic semiconductor layer | Carrier mobility | Heat resistance |
|---|---|---|---|---|
| Example 2-1 | Element 2-1 | A-1 | AA | AA |
| Example 2-2 | Element 2-2 | A-2 | AA | AA |
| Example 2-3 | Element 2-3 | A-3 | AA | AA |
| Example 2-4 | Element 2-4 | A-1/A-2 = 1/1 (Mass ratio) | AA | AA |
| Example 2-5 | Element 2-5 | A-2/A-3 = 1/1 (Mass ratio) | AA | AA |
| Example 2-6 | Element 2-6 | A-1/A-3 = 1/1 (Mass ratio) | AA | AA |
| Example 2-7 | Element 2-7 | A-1/A-2/A-3 = 1/1/1 (Mass ratio) | AA | AA |
| Example 2-8 | Element 2-8 | A-4 | AA | AA |

TABLE 2-continued

| | Element No. | Compound in organic semiconductor layer | Carrier mobility | Heat resistance |
|---|---|---|---|---|
| Example 2-9 | Element 2-9 | A-5 | AA | AA |
| Example 2-10 | Element 2-10 | A-6 | AA | AA |
| Example 2-11 | Element 2-11 | A-7 | E | E |
| Example 2-12 | Element 2-12 | A-8 | E | E |
| Example 2-13 | Element 2-13 | A-9 | AA | AA |
| Example 2-14 | Element 2-14 | A-10 | AA | AA |
| Example 2-15 | Element 2-15 | A-11 | AA | AA |
| Example 2-16 | Element 2-16 | A-12 | B | B |
| Example 2-17 | Element 2-17 | A-13 | D | D |
| Example 2-18 | Element 2-18 | A-14 | D | D |
| Example 2-19 | Element 2-19 | A-15 | B | A |
| Example 2-20 | Element 2-20 | A-16 | AA | AA |
| Example 2-21 | Element 2-21 | A-17 | AA | AA |
| Example 2-22 | Element 2-22 | A-18 | AA | AA |
| Example 2-23 | Element 2-23 | A-19 | AA | AA |
| Example 2-24 | Element 2-24 | A-20 | AA | AA |
| Example 2-25 | Element 2-25 | A-21 | AA | AA |
| Example 2-26 | Element 2-26 | A-22 | AA | AA |
| Example 2-27 | Element 2-27 | A-23 | AA | AA |
| Example 2-28 | Element 2-28 | A-24 | AA | AA |
| Example 2-29 | Element 2-29 | A-25 | A | A |
| Example 2-30 | Element 2-30 | A-26 | A | A |
| Example 2-31 | Element 2-31 | A-27 | C | C |
| Comparative Example 2-1 | Comparative element 2-1 | Comparative compound 1 | G | G |
| Comparative Example 2-2 | Comparative element 2-2 | Comparative compound 2 | G | G |

As presented in Table 2, even in a case where the organic semiconductor layer was an element including a compound having a fused polycyclic structure, in a case where the structure of the compound was out of the range determined in the present invention, the carrier mobility was inferior, and the heat resistance, as a result (Comparative Examples 2-1 and 2-2).

Meanwhile, it is understood that an element in which a compound having a structure determined in the present invention was used for the organic semiconductor layer had excellent carrier mobility and also excellent heat resistance (Examples 2-1 to 2-31).

Synthesis of Compound 12-1

According to Scheme 12, the compound 3-8 (2 g, 4.65 mmol) was obtained from the compound 12-1 (1.83 g, 3.11 mmol).

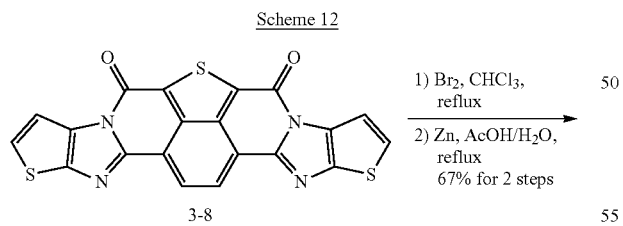

Scheme 12

1) Br$_2$, CHCl$_3$, reflux
2) Zn, AcOH/H$_2$O, reflux
67% for 2 steps

Synthesis of Compounds 13-1 and 13-2

Compounds 13-1 and 13-2 were obtained from the compounds 3-9 and 3-10 in the same manner as in Scheme 12.

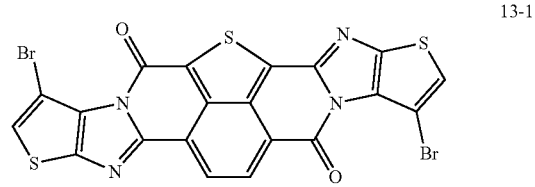

13-1

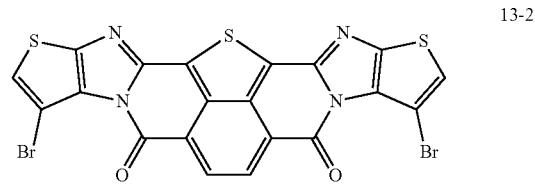

13-2

Synthesis of Compounds 14-1 to 14-3

Compounds 14-1 to 14-3 were obtained from the intermediate in the synthesis of the compound A-4.

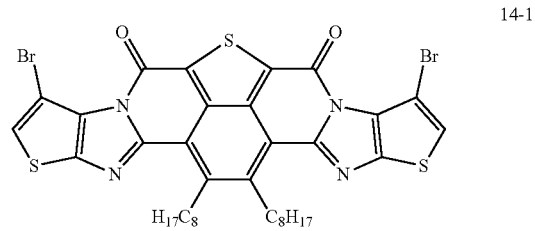

14-1

-continued

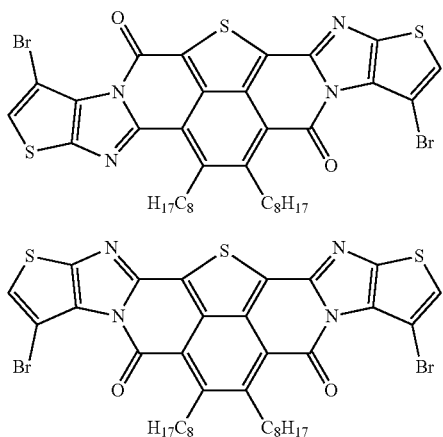

14-2

14-3

Synthesis of Polymer B-1

With reference to U.S. Pat. No. 9,293,708B, as described below, a polymer B-1 (1.41 g) was synthesized from a compound 12-1/4-1 (1 g in total) according to Scheme 13 at the reaction temperature of 80° C. and the reaction time of two minutes. The weight-average molecular weight (Mw) of the polymer B-1 (a) was 3000.

The preparation amounts of the compounds 12-1 and 4-1 were equal in mass ratio. Similarly, in the subsequent polymer synthesis, in a case where a plurality of compounds were used as a constituent component of the structural unit represented by any one of Formulae (8) to (10), the preparation amounts thereof were all equivalent in mass ratio.

A polymer B-1 was obtained in the same manner as in Scheme 13 except that the reaction temperature was 80° C. and the reaction time was 30 minutes. Mw of the polymer B-1 (b) was 12100.

The polymer B-1 was obtained in the same manner as in Scheme 13, except that the reaction temperature was 100° C. and the reaction time was three hours. Mw of the polymer B-1 (C) was 48700.

The polymer B-1 was obtained in the same manner as in Scheme 13, except that the reaction temperature was 120□ and the reaction time was three hours. Mw of the polymer B-1 (d) was 96200.

The polymer B-1 was obtained in the same manner as in Scheme 13, except that the reaction temperature was 120° C. and the reaction time was six hours. Mw of the polymer B-1 (e) was 145800.

Synthesis of Polymer B-2

A polymer B-2 was obtained in the same manner as in Scheme 13, except that compounds 13-2 and 16-1 were used instead of the compounds 12-1 and 4-1. The compound 16-1 was an intermediate of the compound A-1.

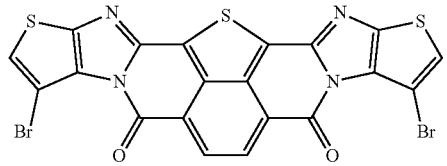

13-2

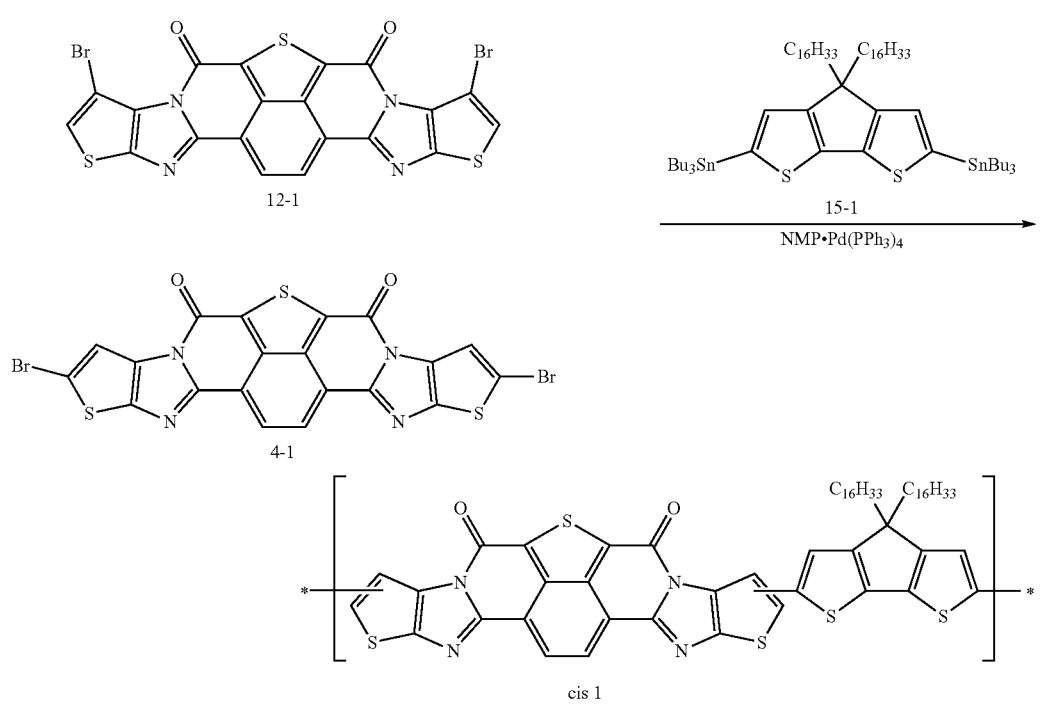

Scheme 13

B-1

16-1

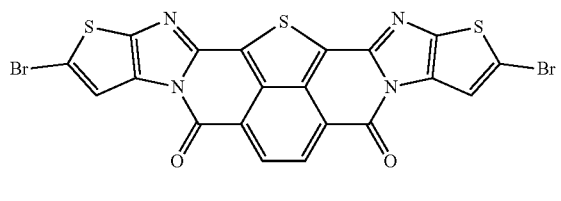

Synthesis of Polymer B-3

A polymer B-3 was obtained in the same manner as in Scheme 13, except that compounds 13-1 and 17-1 were used instead of the compounds 12-1 and 4-1. The compound 17-1 was an intermediate of the compound A-2.

13-1

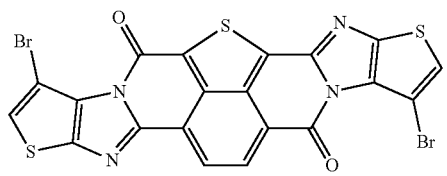

17-1

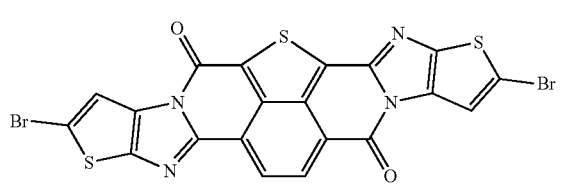

Synthesis of Polymer B-4

A polymer B-4 was obtained in Scheme 13 by using the compounds 12-1, 4-1, 13-2, 16-1, 13-1, and 17-1.

Synthesis of Polymer B-5

A polymer B-5 was obtained in the same manner as in Scheme 13, except that compounds 18-1, 18-2, and 18-3 were used instead of the compounds 12-1 and 4-1. The compounds 18-1, 18-2, and 18-3 each were an intermediate of the compound A-15.

18-1

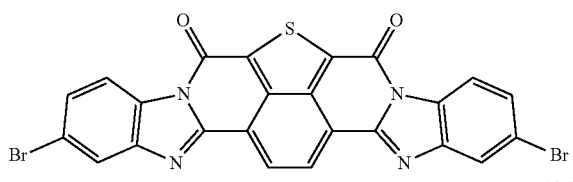

18-2

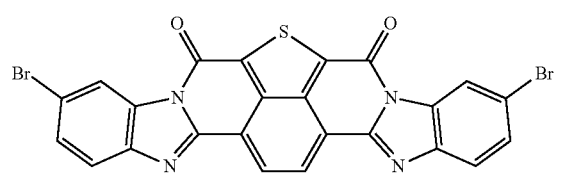

18-3

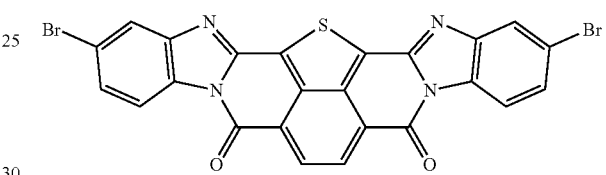

Synthesis of Polymer B-6

A polymer B-6 was obtained in the same manner as in Scheme 13, except that compounds 19-1, 19-2, and 19-3 were used instead of the compounds 12-1 and 4-1. The compounds 19-1, 19-2, and 19-3 each were an intermediate of the compound A-15.

19-1

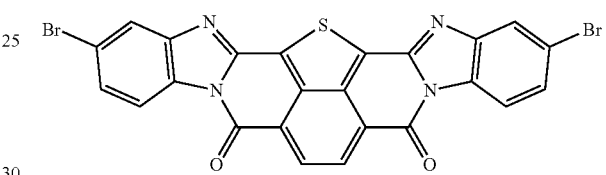

19-2

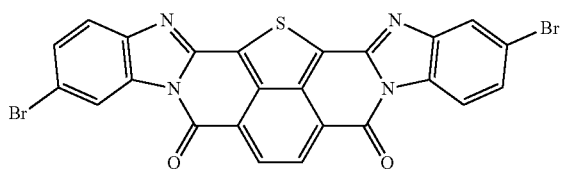

19-3

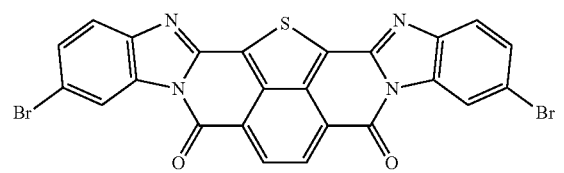

Synthesis of Polymer B-7

A polymer B-7 was obtained in the same manner as in Scheme 13, except that compounds 20-1, 20-2, and 20-3 were used instead of the compounds 12-1 and 4-1. The compounds 20-1, 20-2, and 20-3 each were an intermediate of the compound A-15.

20-1

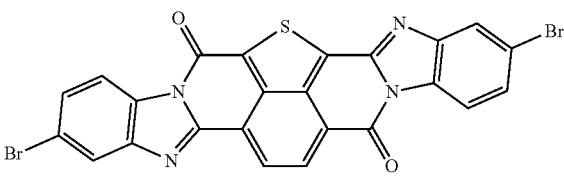

-continued

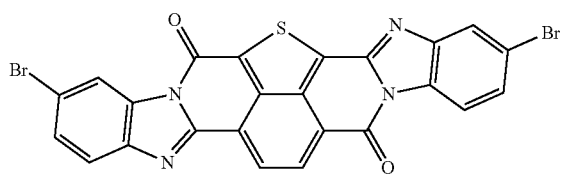
20-2

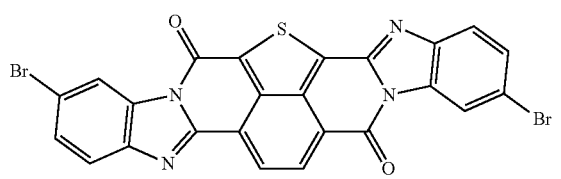
20-3

Synthesis of Polymer B-8

A polymer B-8 was obtained in Scheme 13 by using compounds 18-1, 18-2, 18-3, 19-1, 19-2, 19-3, 20-1, 20-2, and 20-3.

Synthesis of Polymer B-9

A polymer B-9 was obtained in the same manner as in Scheme 13, except that the compounds 14-1 and 21-1 were used instead of the compounds 12-1 and 4-1, and a compound 21-2 synthesized with reference to J. Polym. Sci., A Polym. Chem. 2013, Book 51, p. 1933, and the like was of the compound 15-1. The compound 21-1 was an intermediate of the compound A-4.

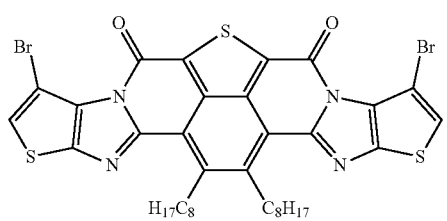
14-1

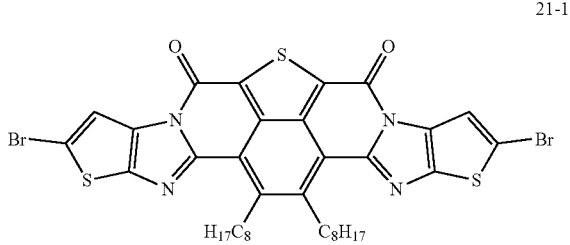
21-1

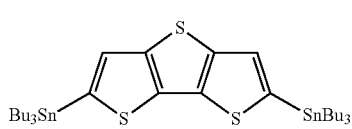
21-2

Synthesis of Polymer B-10

A polymer B-10 was obtained in the same manner as in Scheme 13, except that compounds 14-3 and 22-1 were used instead of the compounds 12-1 and 4-1, and a compound 21-2 was used instead of the compound 15-1.

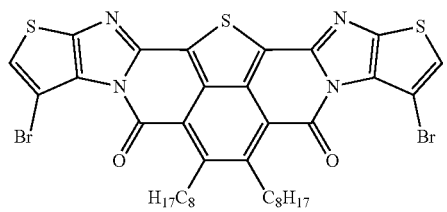
14-3

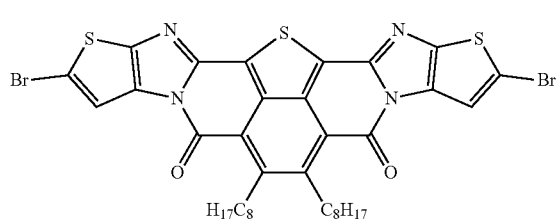
22-1

Synthesis of Polymer B-11

A polymer B-11 was obtained in the same manner as in Scheme 13, except that the compounds 14-2 and 23-1 were used instead of the compounds 12-1 and 4-1, and a compound 21-2 was used instead of the compound 15-1.

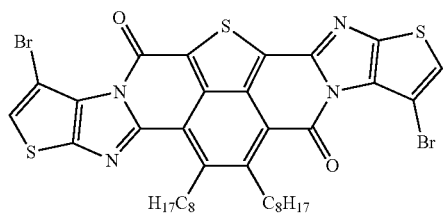
14-2

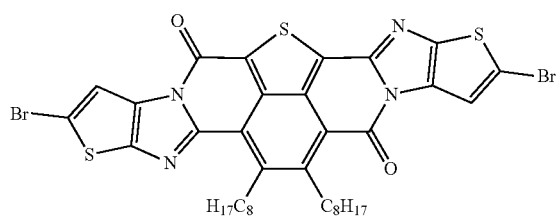
23-1

Synthesis of Polymer B-12

In Scheme 13, a polymer B-12 was obtained in the same manner as in Scheme 13, except that the compounds 14-1, 21-1, 14-2, 22-1, 14-3, and 23-1 were used, and a compound 21-2 was used instead of the compound 15-1.

Synthesis of Polymer B-13

In Scheme 13, a polymer B-13 was obtained in the same manner as in Scheme 13, except that the compounds 12-1, 4-1, 13-2, 16-1, 13-1, and 17-1 were used, and a compound 24-1 synthesized with reference to J. Am. Chem. Soc. 2013, Book 135, p. 4656, and the like was used instead of the compound 15-1.

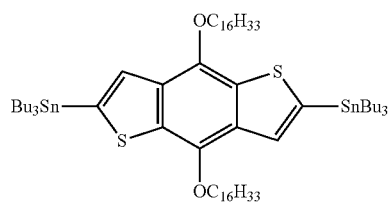

24-1

Synthesis of Polymer B-14

In Scheme 13, a polymer B-14 was obtained in the same manner as in Scheme 13, except that the compounds 14-1, 21-1, 14-2, 22-1, 14-3, and 23-1 were used instead of the compounds 12-1 and 4-1, and a compound 25-1 synthesized with reference to Molecules 2012, Book 17, p. 12163 was used instead of the compound 15-1.

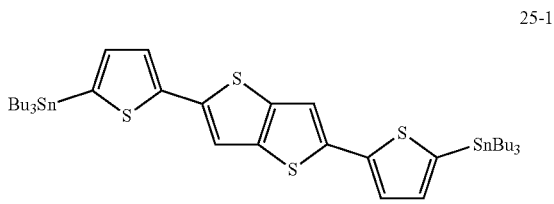

25-1

Synthesis of Polymer B-15

In Scheme 13, a polymer B-15 was synthesized in the same manner as in Scheme 13, except that the compounds 14-1, 21-1, 14-2, 22-1, 14-3, and 23-1 were used instead of compounds 12-1 and 4-1, and a compound 26-1 synthesized in U.S. Pat. No. 8,519,150B was used instead of the compound 15-1.

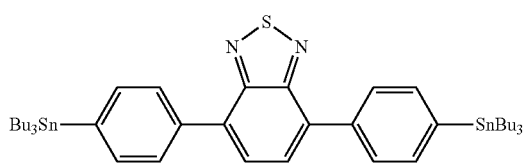

26-1

Synthesis of Polymer B-16

In Scheme 13, a polymer B-16 was synthesized in the same manner as in Scheme 13, except that the compounds 14-1, 21-1, 14-2, 22-1, 14-3, and 23-1 were used instead of the compounds 12-1 and 4-1, and a compound 27-1 synthesized with reference to J. Org. Chem. 2003, Book 68, p. 9813 was used instead of the compound 15-1.

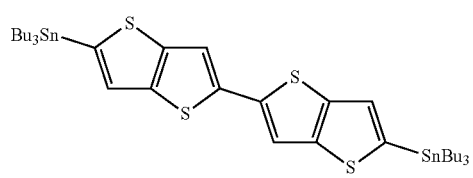

27-1

Synthesis of Polymer B-17

In Scheme 13, a polymer B-17 was synthesized in the same manner as in Scheme 13, except that the compounds 14-1, 21-1, 14-2, 22-1, 14-3, and 23-1 were used instead of the compounds 12-1 and 4-1, and a compound 28-1 synthesized with reference to Macromolecules 2013, Book 46, p. 1337 was used instead of the compound 15-1.

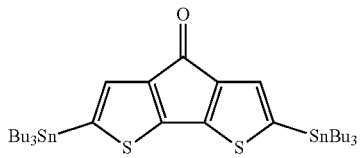

28-1

Synthesis of Polymer B-18

According to Scheme 14, a polymer B-18 (1.02 g) was synthesized by using compounds 14-1/21-1/14-3/22-1/14-2/23-1 (1 g in total) and using a compound 29-1 synthesized with reference to J. Ame. Chem. Soc. 2011, Book 133, p. 11442 at the reaction temperature of 100° C. and the reaction time of three hours.

Scheme 14
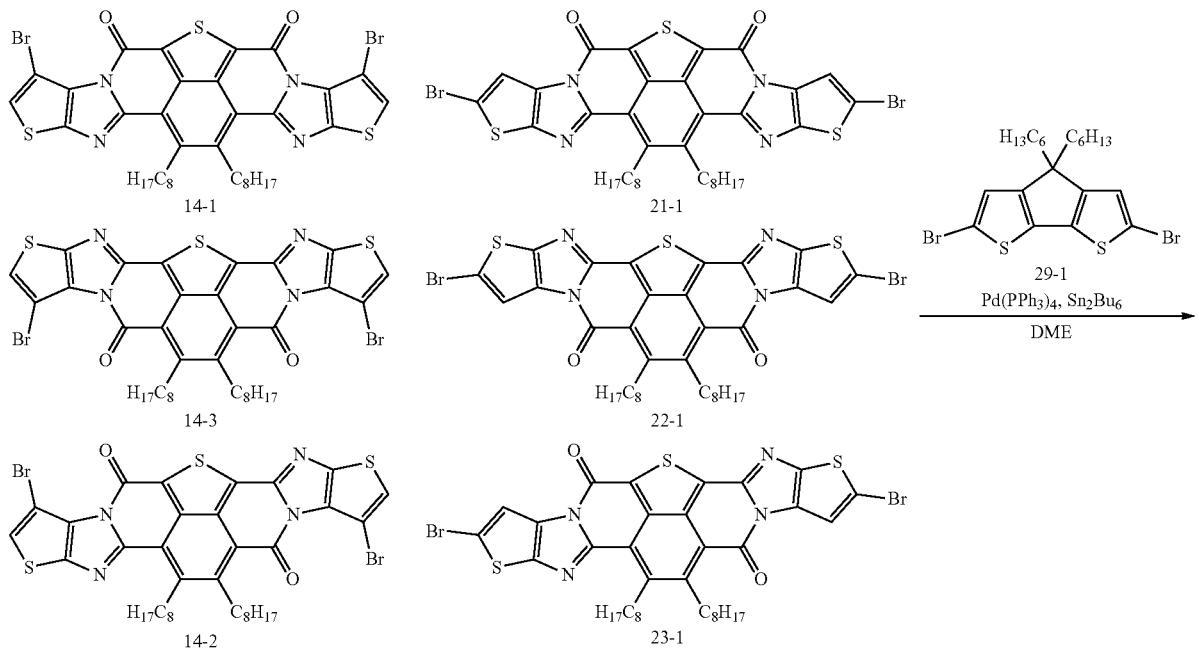
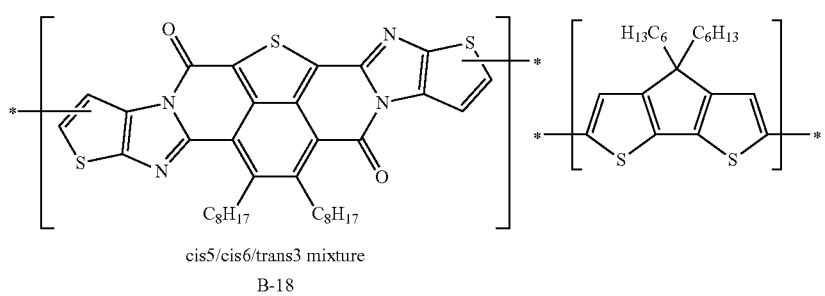
cis5/cis6/trans3 mixture
B-18
Synthesis of Polymer B-19
In Scheme 13, a polymer B-19 was synthesized in the same manner as in Scheme 13, except that the compounds 14-1, 21-1, 14-3, 22-1, 14-2, and 23-1 were used instead of the compounds 12-1 and 4-1, and a compound 30-1 synthesized with reference to Tetrahedron Letters, 2013, Book 22, pg. 2795 was used instead of the compound 15-1.
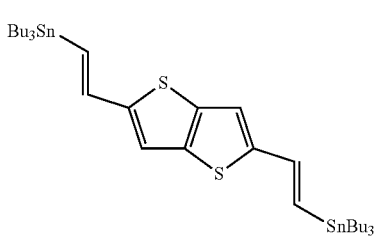

Synthesis of Polymer B-20
A polymer B-20 (1.34 g) was synthesized from compounds 12-1/4-1/13-2/16-1/13-1/17-1 (1 g in total) according to Scheme 15 at temperature of 100° C. and the reaction time of three hours.
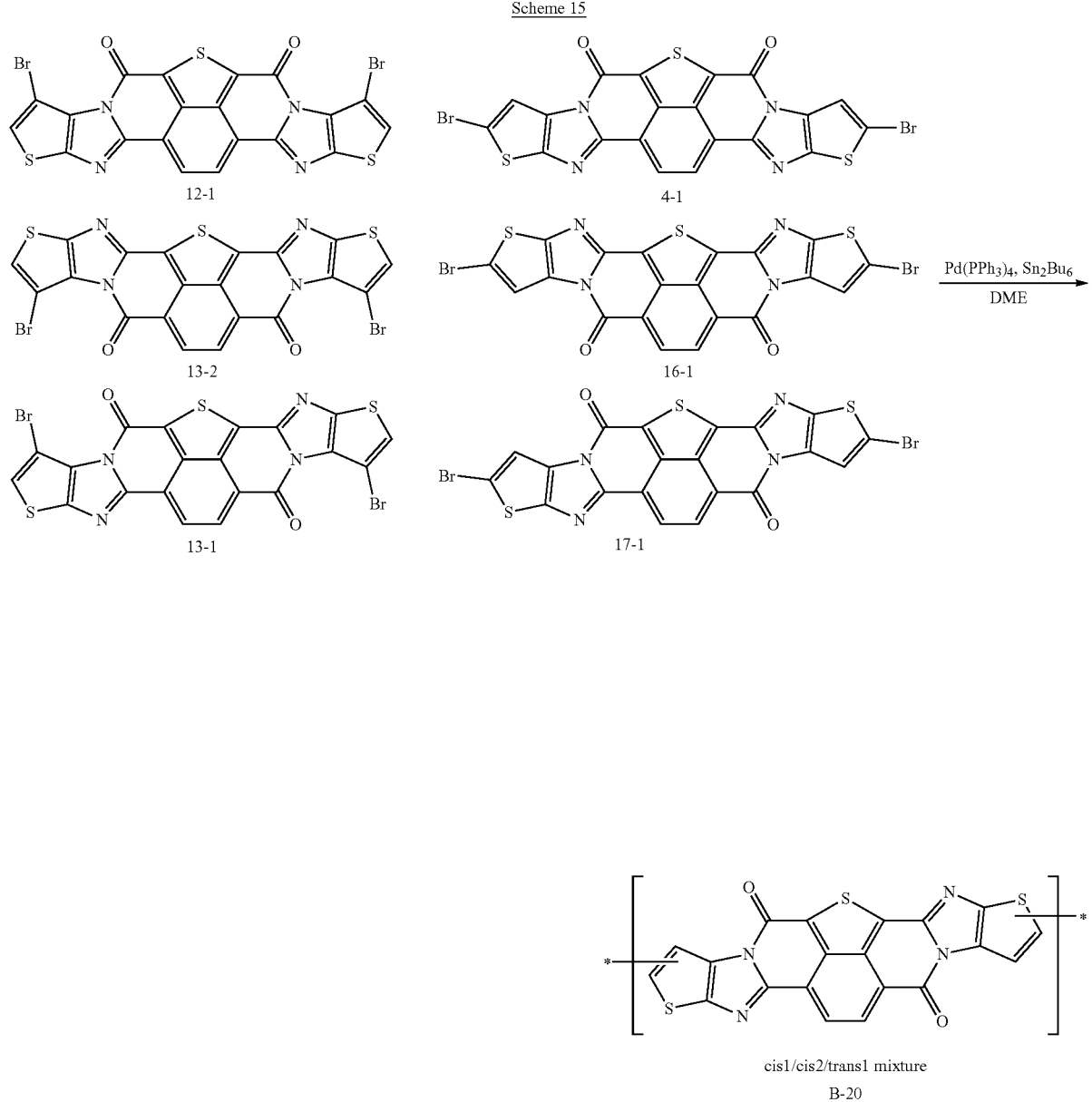

Comparative Synthesis Example 2

Comparative polymers 3 and 4 were synthesized according to the following scheme.

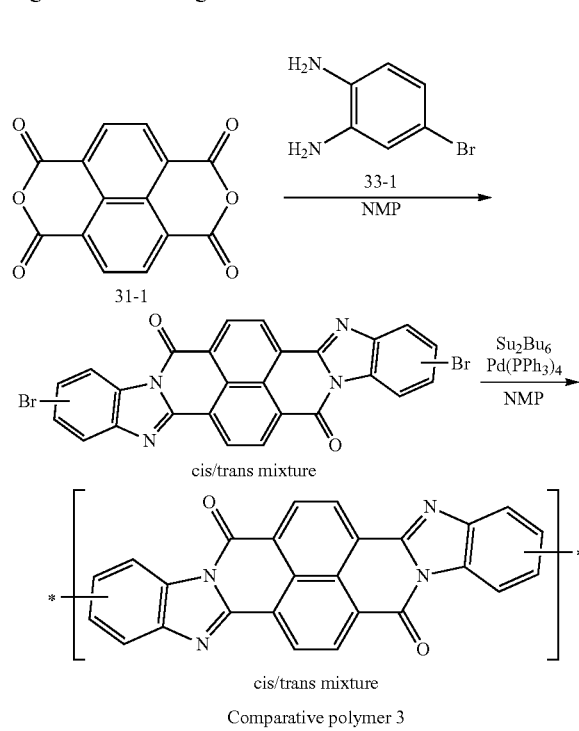

Comparative polymer 3

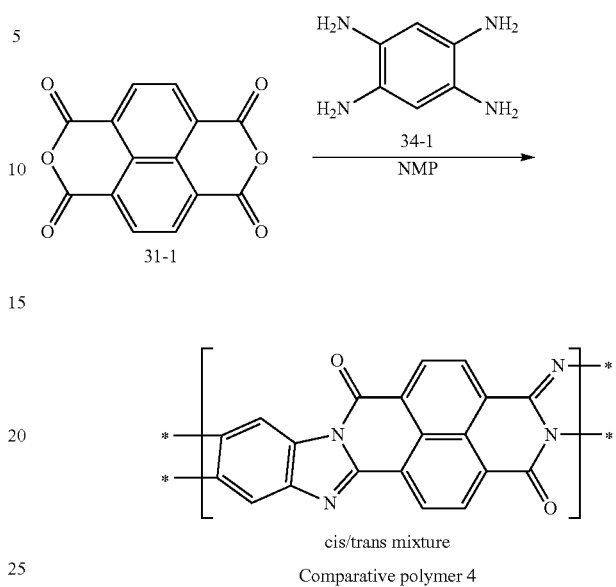

Comparative polymer 4

Structures of the obtained compound B-1 to B-20 and the obtained comparative polymer 3 and 4 are provided below. A mixture of a cis isomer and a trans isomer is described using the structure of the trans isomer for convenience of description.

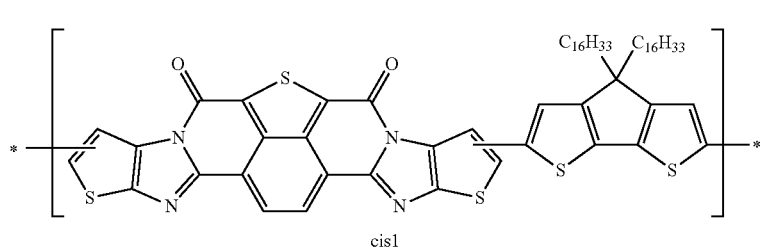

B-1

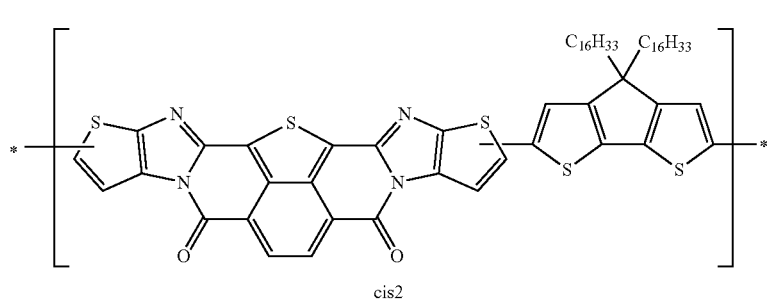

B-2

-continued
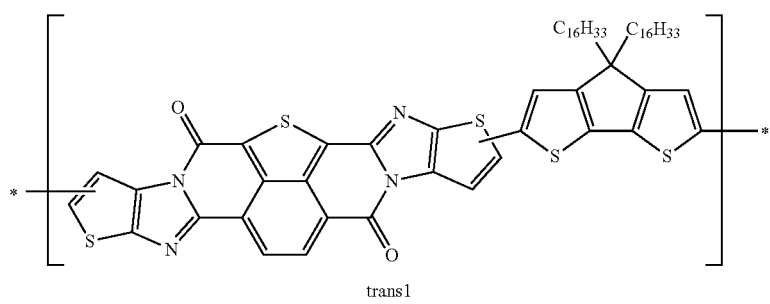
trans1
B-3
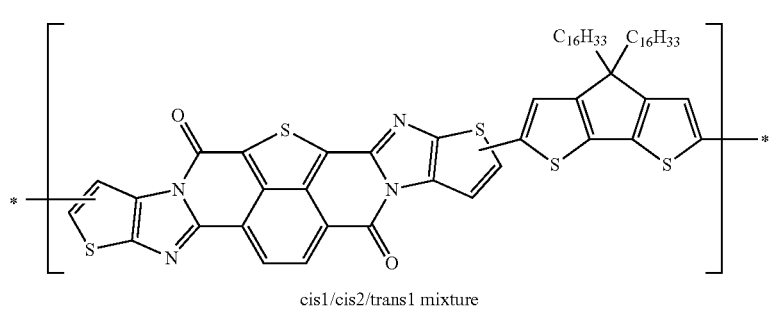
cis1/cis2/trans1 mixture
B-4
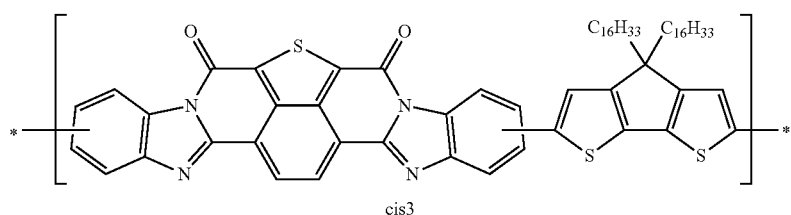
cis3
B-5
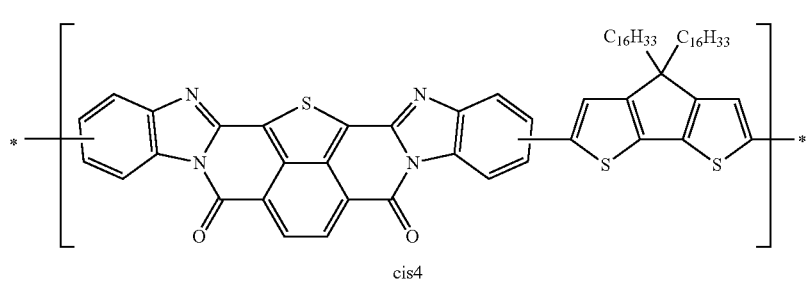
cis4
B-6
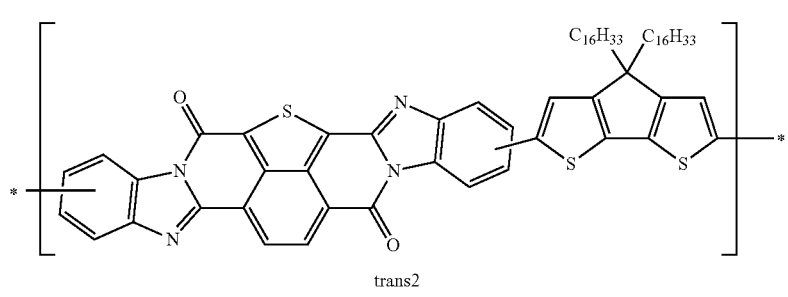
trans2
B-7

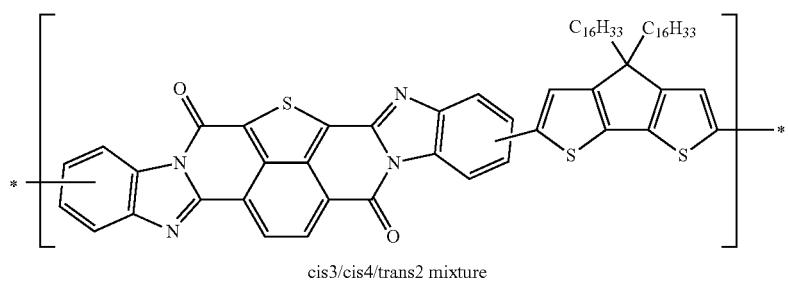
B-8
cis3/cis4/trans2 mixture
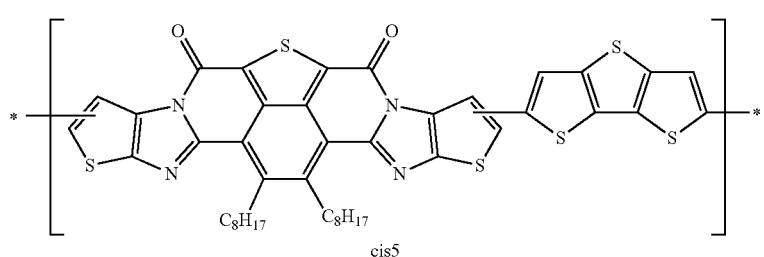
B-9
cis5
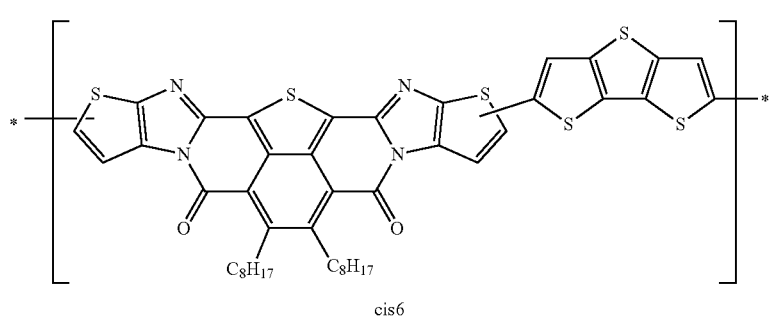
B-10
cis6
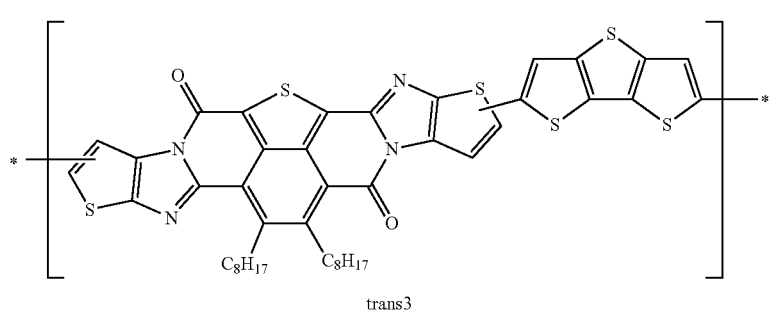
B-11
trans3
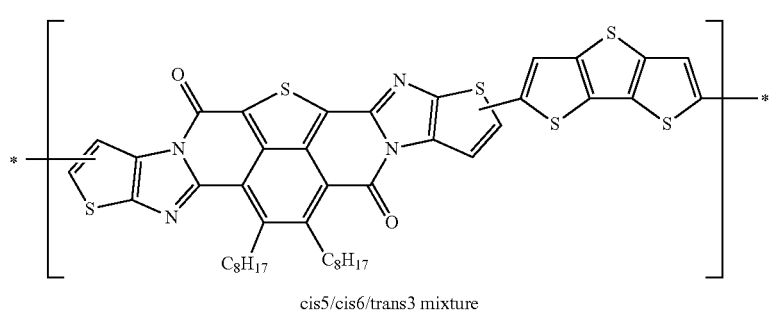
B-12
cis5/cis6/trans3 mixture -continued
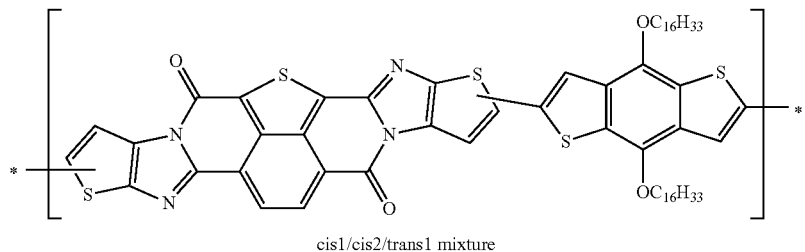
B-13
cis1/cis2/trans1 mixture
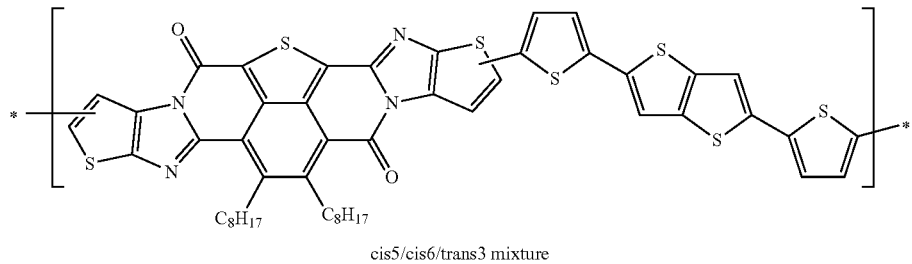
B-14
cis5/cis6/trans3 mixture
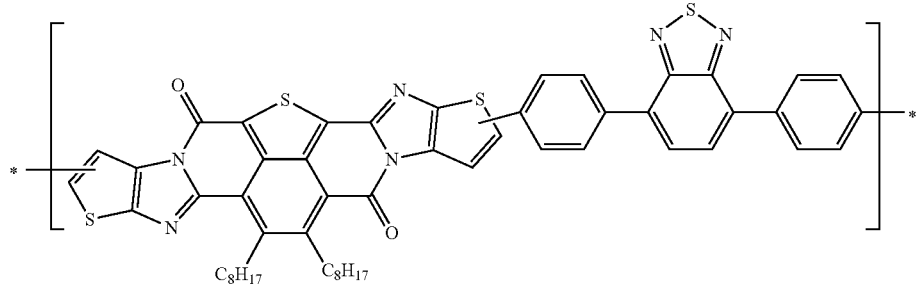
B-15
cis5/cis6/trans3 mixture
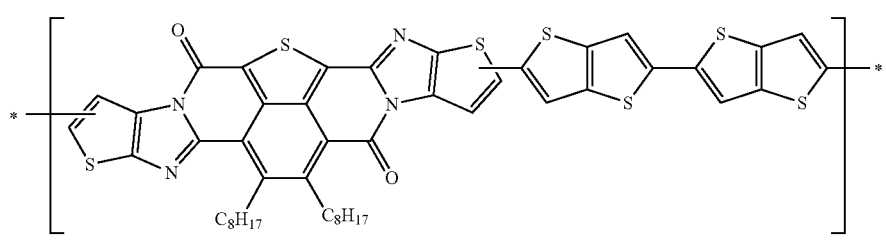
B-16
cis5/cis6/trans3 mixture
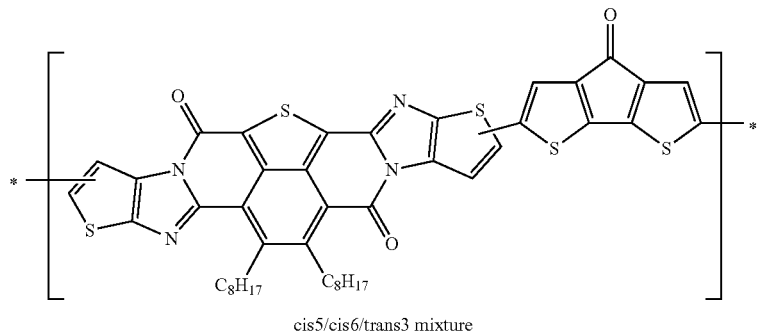
B-17
cis5/cis6/trans3 mixture -continued

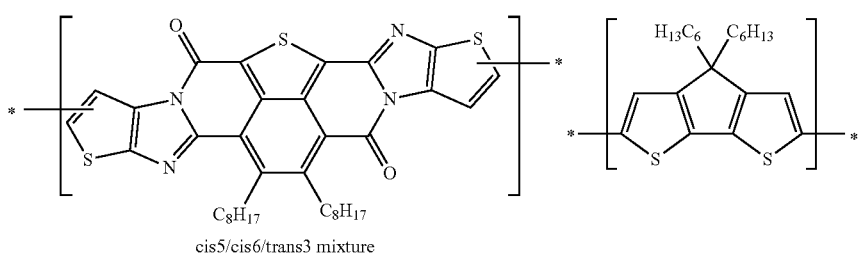

B-18 cis5/cis6/trans3 mixture

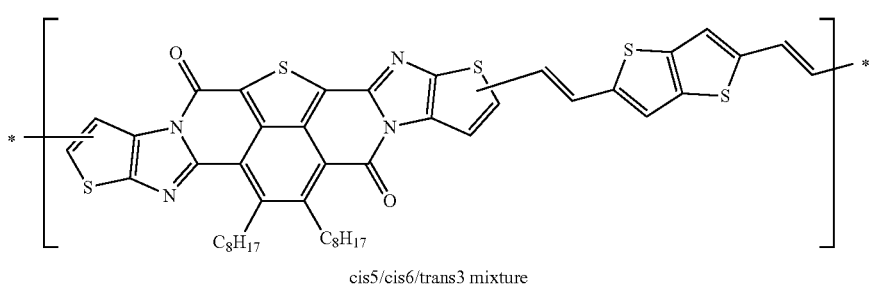

B-19 cis5/cis6/trans3 mixture

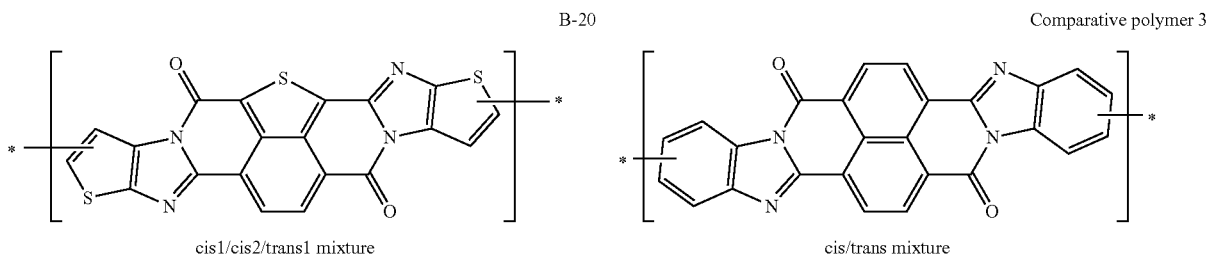

B-20     Comparative polymer 3 cis1/cis2/trans1 mixture     cis/trans mixture

Comparative polymer 4

cis/trans mixture

Preparation of Organic Semiconductor Composition 0.1 mass % solution of the polymer B-1 was prepared by mixing the polymer B-1 (a) synthesized above and toluene as a solvent and heated to 40° C., so as to obtain an organic semiconductor polymer composition 1.

The organic semiconductor polymer compositions 2 to 24 and the comparative polymer compositions 1 and 2 were prepared in the same manner, except that each polymer of the polymers B-1 (b) to (e), and B-2 to B-20, and the comparative polymers 3 and 4 was used instead of the polymer B-1(a).

[Manufacturing of Bottom Gate-Bottom Contact Type Element by Coating Process]

The organic thin film transistor element 3-1 (hereinafter, referred to as an "element 3-1") was obtained by casting (drop cast method) the organic semiconductor polymer composition 1 on a substrate for the field effect transistor (FET) characteristic measurement heated to 40° C. in a nitrogen atmosphere.

As the substrate for FET characteristic measurement, a silicon substrate having a bottom gate and bottom contact structure comprising chromium/gold (gate width W=100 mm, gate length L=100 μm) disposed in a comb shape as source and drain electrodes and $SiO_2$ (film thickness of 500 nm) as an insulating film was used.

Organic thin film transistor elements 3-2 to 3-24 (hereinafter, also referred to as "elements 3-2 to 3-24") and comparative organic thin film transistor elements 3-1 and 3-2 (hereinafter, also referred to as "comparative elements 3-1 and 3-2) were manufactured in the same manner as in the manufacturing of the element 3-1 except that each of the organic semiconductor polymer compositions 2 to 24 and the comparative polymer compositions 1 and 2 was used instead of the organic semiconductor polymer composition 1. The obtained elements 3-1 to 3-24 and the obtained comparative elements 3-1 and 3-2 were respectively used as the organic thin film transistor elements in Examples 3-1 to 3-24, and Comparative Examples 3-1 and 3-2.

Evaluation of Carrier Mobility and Heat Resistance

With respect to each organic thin film transistor element (the elements 3-1 to 3-24 and the comparative elements 3-1 and 3-2), the carrier mobility and the heat resistance were evaluated in the same manner as in the evaluation of the elements 1-1 to 1-31 and the comparative elements 1-1 and 1-2. The results thereof are presented in the following table.

TABLE 3

| | Element No. | Kind of polymer in organic semiconductor layer and Mw thereof | | Carrier mobility | Heat resistance |
|---|---|---|---|---|---|
| Example 3-1 | Element 3-1 | B-1(a) | Mw: 3000 | AA | AA |
| Example 3-2 | Element 3-2 | B-1(b) | Mw: 12100 | AA | AA |
| Example 3-3 | Element 3-3 | B-1(c) | Mw: 48700 | AA | AA |
| Example 3-4 | Element 3-4 | B-1(d) | Mw: 96200 | AA | AA |
| Example 3-5 | Element 3-5 | B-1(e) | Mw: 145800 | AA | AA |
| Example 3-6 | Element 3-6 | B-2 | Mw: 61200 | AA | AA |
| Example 3-7 | Element 3-7 | B-3 | Mw: 57000 | AA | AA |
| Example 3-8 | Element 3-8 | B-4 | Mw: 34500 | AA | AA |
| Example 3-9 | Element 3-9 | B-5 | Mw: 87900 | A | AA |
| Example 3-10 | Element 3-10 | B-6 | Mw: 7100 | A | AA |
| Example 3-11 | Element 3-11 | B-7 | Mw: 11400 | A | AA |
| Example 3-12 | Element 3-12 | B-8 | Mw: 11800 | A | AA |
| Example 3-13 | Element 3-13 | B-9 | Mw: 9700 | AA | AA |
| Example 3-14 | Element 3-14 | B-10 | Mw: 125300 | AA | AA |
| Example 3-15 | Element 3-15 | B-11 | Mw: 78900 | AA | AA |
| Example 3-16 | Element 3-16 | B-12 | Mw: 23000 | AA | AA |
| Example 3-17 | Element 3-17 | B-13 | Mw: 79100 | AA | AA |
| Example 3-18 | Element 3-18 | B-14 | Mw: 134600 | AA | AA |
| Example 3-19 | Element 3-19 | B-15 | Mw: 4500 | A | A |
| Example 3-20 | Element 3-20 | B-16 | Mw: 29300 | C | B |
| Example 3-21 | Element 3-21 | B-17 | Mw: 81100 | D | D |
| Example 3-22 | Element 3-22 | B-18 | Mw: 54600 | E | D |
| Example 3-23 | Element 3-23 | B-19 | Mw: 39700 | B | B |
| Example 3-24 | Element 3-24 | B-20 | Mw: 141300 | E | E |
| Comparative Example 3-1 | Comparative element 3-1 | Comparative polymer 3 | Mw: 5200 | G | G |
| Comparative Example 3-2 | Comparative element 3-2 | Comparative polymer 4 | Mw: 7600 | F | F |

As presented in Table 3, even in a case where the organic semiconductor layer was an element including a polymer having a fused polycyclic structure, in a case where the structure of the polymer was out of the range determined in the present invention, the carrier mobility was inferior, and the heat resistance, as a result (Comparative Examples 3-1 and 3-2).

Meanwhile, it is understood that an element in which a polymer having a structure determined in the present invention was used for the organic semiconductor layer had excellent carrier mobility and also excellent heat resistance (Examples 3-1 to 3-24).

[Manufacturing of Bottom Gate-Bottom Contact Type Element by Flexographic Printing]

A coating solution was prepared by dissolving 0.5 mass % of the polymer B-1 (a), 0.5 mass % of poly α-methylstyrene, and 0.05% of BYK 323 (manufactured by BYK-Chemie GmbH) as a surfactant in tetralin, so as to obtain an organic semiconductor polymer composition 4-1. The organic semiconductor polymer compositions 4-2 to 4-24 and the comparative polymer compositions 4-1 and 4-2 were prepared in the same manner, except that each polymer of the polymers B-1 (b) to (e), and B-2 to B-20, and the comparative polymers 3 and 4 was used instead of the polymer B-1 (a).

In the same manner as in the manufacturing of the element 3-1, a bottom gate-bottom contact type substrate for FET characteristic measurement was prepared, and the organic semiconductor polymer composition 4-1 was printed thereon by a flexo printing method, so as to form an organic semiconductor layer. An organic thin film transistor element 4-1 (hereinafter, also referred to as an "element 4-1") was obtained.

Specific method of forming the organic semiconductor layer by a flexographic printing method is as described below.

A flexo aptitude testing machine F1 (manufactured by IDC Testing Systems Co., Ltd.) was used as a printing device, and 1.70% of AFP DSH (manufactured by Asahi Kasei Co., Ltd.)/solid image was used as a flexo resin plate. Printing was performed at the pressure between the printing plate and the substrate of 60 N, and a transportation speed of 0.4 m/sec, and drying was performed at 60° C. for two hours so to form an organic semiconductor layer (film thickness: 50 nm).

Organic thin film transistor elements 4-2 to 4-24 (hereinafter, also referred to as "elements 4-2 to 4-24") and comparative organic thin film transistor elements 4-1 and 4-2 (hereinafter, also referred to as "comparative elements 4-1 and 4-2") were respectively manufactured in the same manner as in the manufacturing of the element 4-1 except that each polymer composition of the organic semiconductor polymer compositions 4-2 to 4-24 and the comparative polymer compositions 4-1 and 4-2 was used instead of the organic semiconductor polymer composition 4-1. The obtained elements 4-1 to 4-24, and the obtained comparative elements 4-1 and 4-2 were respectively used as the organic thin film transistor elements in Examples 4-1 to 4-24, and Comparative Examples 4-1 and 4-2.

[Evaluation of Carrier Mobility and Heat Resistance]

With respect to each organic thin film transistor element (the elements 4-1 to 4-24 and the comparative elements 4-1 and 4-2), the carrier mobility and the heat resistance were evaluated in the same manner as in the evaluation of the elements 1-1 to 1-31 and the comparative elements 1-1 and 1-2. The results thereof are presented in the following table.

TABLE 4

| | Element No. | Polymer in organic semiconductor layer | | Carrier mobility | Heat resistance |
|---|---|---|---|---|---|
| Example 4-1 | Element 4-1 | B-1(a) | Mw: 3000 | AA | AA |
| Example 4-2 | Element 4-2 | B-1(b) | Mw: 12100 | AA | AA |
| Example 4-3 | Element 4-3 | B-1(c) | Mw: 48700 | AA | AA |
| Example 4-4 | Element 4-4 | B-1(d) | Mw: 96200 | AA | AA |
| Example 4-5 | Element 4-5 | B-1(e) | Mw: 145800 | AA | AA |
| Example 4-6 | Element 4-6 | B-2 | Mw: 61200 | AA | AA |
| Example 4-7 | Element 4-7 | B-3 | Mw: 57000 | AA | AA |
| Example 4-8 | Element 4-8 | B-4 | Mw: 34500 | AA | AA |
| Example 4-9 | Element 4-9 | B-5 | Mw: 87900 | A | AA |
| Example 4-10 | Element 4-10 | B-6 | Mw: 7100 | A | AA |
| Example 4-11 | Element 4-11 | B-7 | Mw: 11400 | A | AA |
| Example 4-12 | Element 4-12 | B-8 | Mw: 11800 | A | AA |
| Example 4-13 | Element 4-13 | B-9 | Mw: 9700 | AA | AA |
| Example 4-14 | Element 4-14 | B-10 | Mw: 125300 | AA | AA |
| Example 4-15 | Element 4-15 | B-11 | Mw: 78900 | AA | AA |
| Example 4-16 | Element 4-16 | B-12 | Mw: 23000 | AA | AA |
| Example 4-17 | Element 4-17 | B-13 | Mw: 79100 | AA | AA |
| Example 4-18 | Element 4-18 | B-14 | Mw: 134600 | AA | AA |
| Example 4-19 | Element 4-19 | B-15 | Mw: 4500 | A | A |
| Example 4-20 | Element 4-20 | B-16 | Mw: 29300 | C | B |
| Example 4-21 | Element 4-21 | B-17 | Mw: 81100 | D | D |
| Example 4-22 | Element 4-22 | B-18 | Mw: 54600 | E | D |
| Example 4-23 | Element 4-23 | B-19 | Mw: 39700 | B | B |
| Example 4-24 | Element 4-24 | B-20 | Mw: 141300 | E | E |
| Comparative Example 4-1 | Comparative element 4-1 | Comparative polymer 3 | Mw: 5200 | G | G |
| Comparative Example 4-2 | Comparative element 4-2 | Comparative polymer 4 | Mw: 7600 | F | F |

As presented in Table 4, even in a case where the organic semiconductor layer was an element including a polymer having a fused polycyclic structure, in a case where the structure of the polymer was out of the range determined in the present invention, the carrier mobility was inferior, and the heat resistance, as a result (Comparative Examples 4-1 and 4-2).

Meanwhile, it is understood that an element in which a polymer having a structure determined in the present invention was used for the organic semiconductor layer had excellent carrier mobility and also excellent heat resistance (Examples 4-1 to 4-24).

The present invention has been described with the embodiments thereof, any details of the description of the present invention are not limited unless described otherwise, and it is obvious that the present invention is widely construed without departing from the spirit and gist of the present invention disclosed in the accompanying claims.

The present application claims the priority of JP2017-071818 filed in Japan on Mar. 31, 2017, the contents of which are incorporated herein by reference, as a part of the description of the present specification.

EXPLANATION OF REFERENCES

10: substrate
20: gate electrode
30: gate insulating film
40: source electrode
42: drain electrode
50: organic semiconductor film
60: sealing layer
100, 200: organic thin film transistor element

What is claimed is:
1. An organic semiconductor element, comprising:
an organic semiconductor layer containing a compound represented by Formula (1), a compound represented by Formula (2), and/or a compound represented by Formula (3), or containing a polymer having at least one structural unit represented by any one of Formulae (8) to (10),

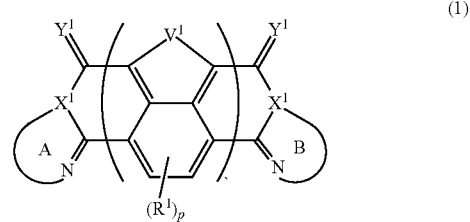

(1)

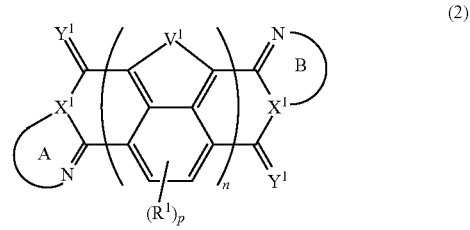

(2)

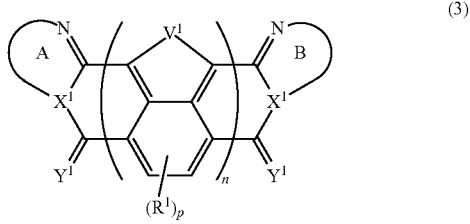

(3)

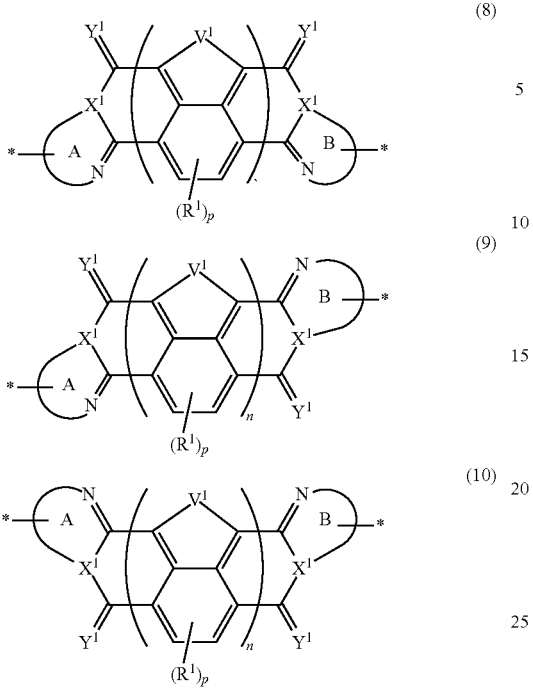

(8)

(9)

(10)

in each formula, X¹ represents a nitrogen atom or CR$^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, Y¹ represents an oxygen atom, a sulfur atom, CR$^b_2$, or NR$^c$, V¹ represents NR$^d$, an oxygen atom, a sulfur atom, or a selenium atom, R$^a$, R$^b$, R$^c$, and R$^d$ each represent a hydrogen atom or a substituent, R¹ represents a halogen atom or a group represented by Formula (W), and p is an integer of 0 to 2, n represents 1 or 2,

* represents a bonding site,

*-L-T                                    Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group,

* represents a bonding site, (L-1)

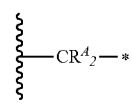

(L-2)

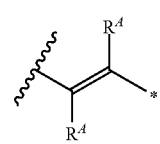

(L-3)

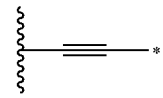

(L-4)

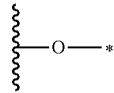

(L-5)

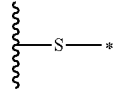

(L-6)

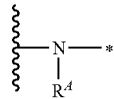

(L-7)

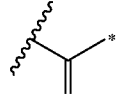

(L-8)

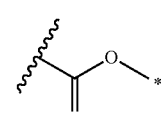

(L-9)

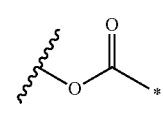

(L-10)

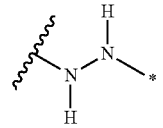

(L-11)

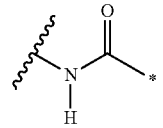

(L-12)

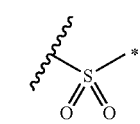

(L-13)

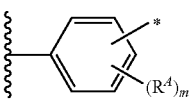

(L-14)

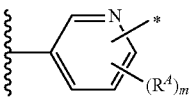

(L-15)

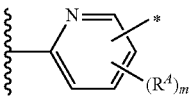

-continued

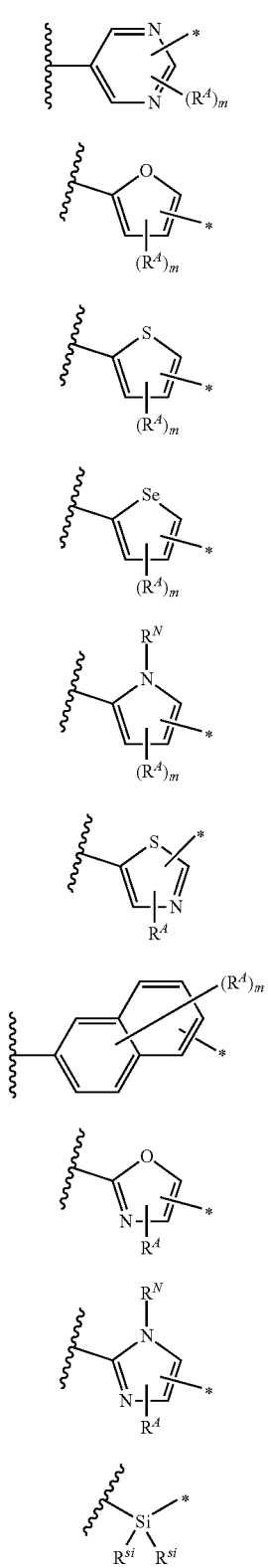

(L-16)
(L-17)
(L-18)
(L-19)
(L-20)
(L-21)
(L-22)
(L-23)
(L-24)
(L-25)

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25),
in Formulae (L-1), (L-2), (L-6), and (L-13) to (L-24), $R^A$ represents a hydrogen atom or a substituent,
in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6,
in Formulae (L-20) and (L-24), $R^N$ represents a hydrogen atom or a substituent, and
in Formula (L-25), $R^{si}$ represents a hydrogen atom, an alkyl group, an alkenyl group, or an alkynyl group.

2. The organic semiconductor element according to claim 1, wherein in Formulae (1) to (3), and (8) to (10), $Y^1$ represents an oxygen atom or a sulfur atom.

3. The organic semiconductor element according to claim 1, wherein rings A and B each are a fused ring structure represented by Formula (4) or (5),

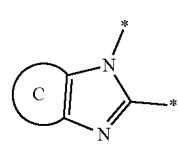

(4)

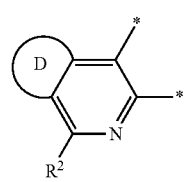

(5)

in each formula, rings C and D each represent a 5-membered aromatic ring or a 6-membered aromatic ring, or a fused ring including a 5-membered aromatic ring or a 6-membered aromatic ring,
$R^2$ represents a hydrogen atom, a halogen atom, or a group represented by Formula (W), and
* represents a bonding site,
here, in the fused ring structure represented by Formula (4) or (5) in Formulae (8) the (10), the rings C and D each have one bonding site for being incorporated into a polymer chain.

4. The organic semiconductor element according to claim 3, wherein the fused ring structure represented by Formula (4) is a fused ring structure represented by Formula (6) or (7),

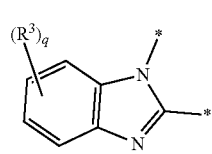

(6)

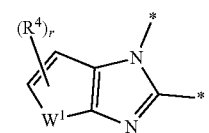

(7)

in each formula, $R^3$ and $R^4$ each represent a halogen atom or a group represented by Formula (W), q is an integer of 0 to 4, and r is an integer of 0 to 2, and $W^1$ represents a chalcogen atom, here, in the fused ring structure represented by Formula (6) or (7) in Formulae (8) to (10), one of the ring-constituting atoms of a ring which may have $R^3$ or $R^4$ has a bonding site to be incorporated into a polymer chain.

5. The organic semiconductor element according to claim 4, wherein the rings A and B each are a fused ring structure represented by Formula (7), here, in the fused ring structure represented by Formula (7) in Formulae (8) to (10), one of the ring-constituting atoms of the ring which may have $R^4$ has one bonding site for being incorporated into a polymer chain.

6. The organic semiconductor element according to claim 1, wherein, in Formula (W), L is a divalent group selected from Formulae (L-1), (L-2), (L-3), (L-4), (L-13), (L-17), and (L-18), or a group obtained by bonding two or more divalent groups selected from Formulae (L-1), (L-2), (L-3), (L-4), (L-13), (L-17), and (L-18).

7. The organic semiconductor element according to claim 1, wherein the polymer has a structure represented by Formula (G), $$*—Ar^1\text{-}(Vr)_{p3}\text{-}Ar^2—*\qquad\text{Formula (G)}$$

in Formula (G), $Ar^1$ and $Ar^2$ each represent a single bond, or is a vinylene group, an ethynylene group, an arylene group, or a heteroarylene group, or is a divalent group formed by linking two or more groups selected from the vinylene group, the ethynylene group, the arylene group, and the heteroarylene group, and Vr represents a divalent conjugated group having 2 to 40 carbon atoms, and p3 is an integer of 1 to 6.

8. The organic semiconductor element according to claim 7, wherein the polymers alternately have a structural unit represented by any one of Formulae (8) to (10) and a structure represented by Formula (G).

9. The organic semiconductor element according to claim 7, wherein, in Formula (G), Vr is a structure selected from Formulae ($V_D$-1) to ($V_D$-16) and ($V_A$-1) to ($V_A$-11),

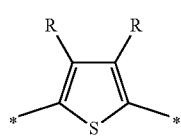

($V_D$-1)

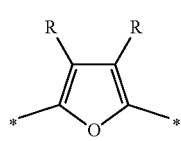

($V_D$-2)

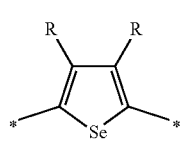

($V_D$-3)

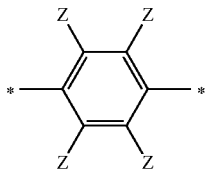

($V_D$-4)

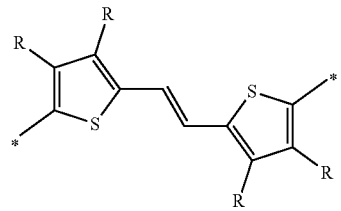

($V_D$-5)

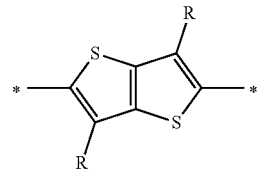

($V_D$-6)

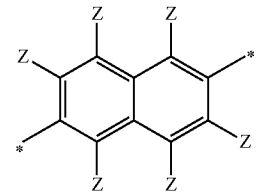

($V_D$-7)

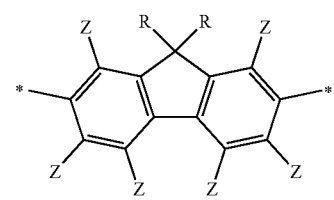

($V_D$-8)

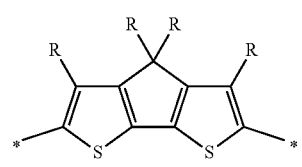

($V_D$-9)

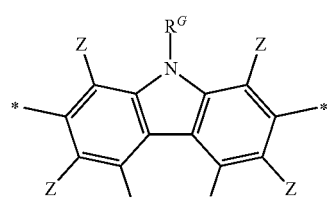

($V_D$-10)

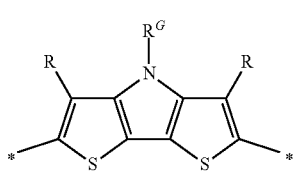

($V_D$-11)

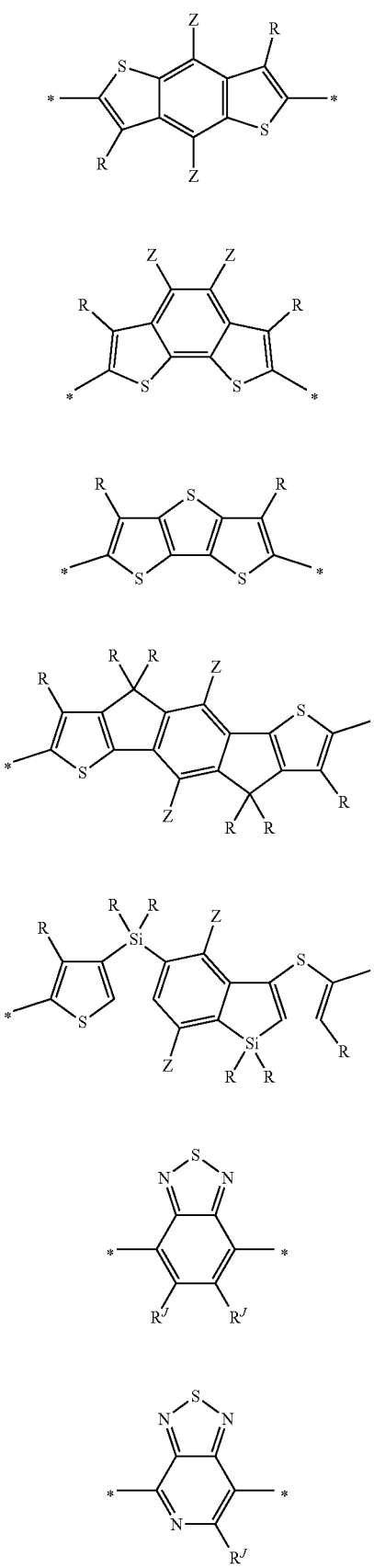
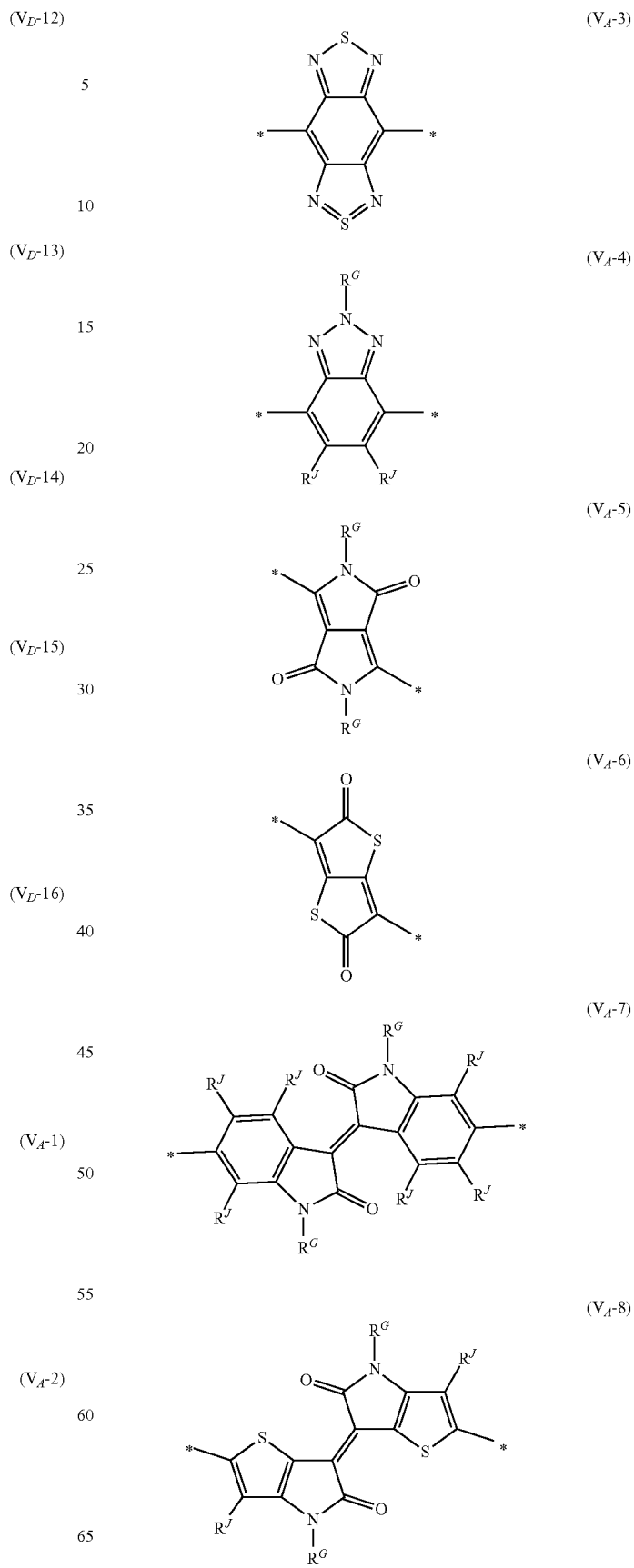

(V$_A$-9)

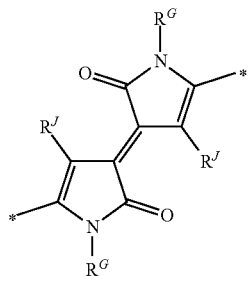

(V$_A$-10)

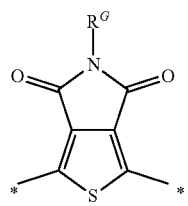

(V$_A$-11)

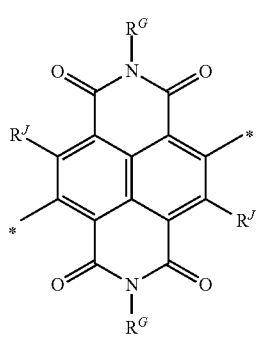

in each formula, R and Z each represent a hydrogen atom, a halogen atom, or an alkyl group, R$^G$ represents an alkyl group, R$^J$ represents a hydrogen atom, an alkyl group, a cyano group, or a halogen atom, and

* represents a bonding site.

10. The organic semiconductor element according to claim 7,
wherein p3 in Formula (G) is 1.

11. The organic semiconductor element according to claim 7,
wherein Ar$^1$ and Ar$^2$ each represent a single bond or a divalent group represented by Formula (Ar-1) or (Ar-2), (Ar-1)

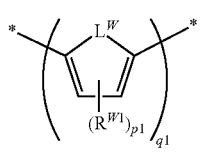

(Ar-2)

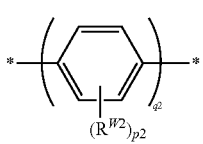

in each formula, R$^W$ represents an alkyl group, and p1 is an integer of 0 to 2, L$^W$ represents a chalcogen atom, R$^{W2}$ represents an alkyl group, and p2 is an integer of 0 to 4, q1 and q2 each are an integer of 1 to 4, and

* represents a bonding site.

12. The organic semiconductor element according to claim 7,
wherein Vr in Formula (G) represents a divalent group represented by any one of Formulae (V$_D$-1) to (V$_D$-16).

13. The organic semiconductor element according to claim 1,
wherein the organic semiconductor element is an organic thin film transistor element.

14. An organic semiconductor composition comprising:
a compound represented by Formula (1), a compound represented by Formula (2), and/or a compound represented by Formula (3), or a polymer having at least one structural unit represented by any one of Formulae (8) to (10); and
a solvent, (1)

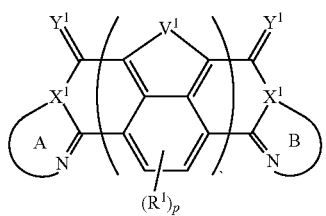

(2)

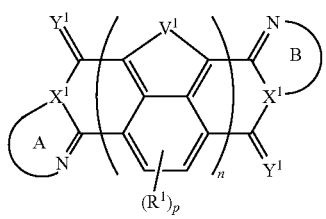

(3)

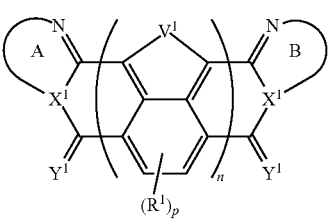

(8)

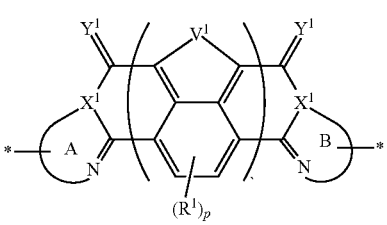

(9)

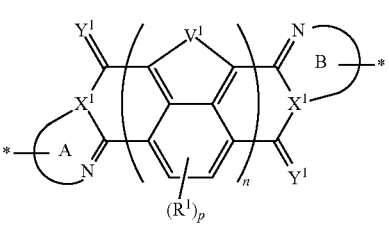

-continued

(10)
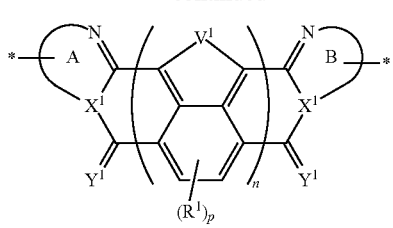

in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b{}_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, $R^1$ represents a halogen atom or a group represented by Formula (W), and p is an integer of 0 to 2, n represents 1 or 2, \* represents a bonding site, \*-L-T   Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group, \* represents a bonding site,

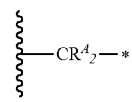 (L-1)

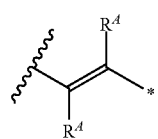 (L-2)

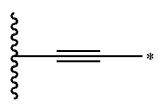 (L-3)

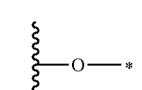 (L-4)

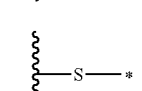 (L-5)

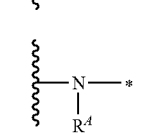 (L-6)

-continued

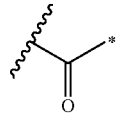 (L-7)

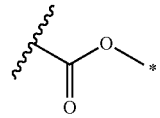 (L-8)

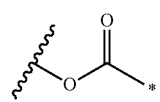 (L-9)

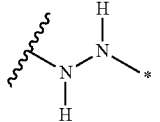 (L-10)

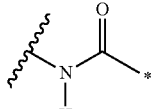 (L-11)

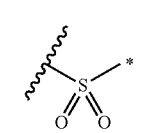 (L-12)

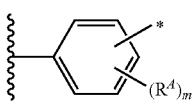 (L-13)

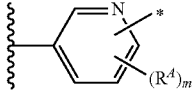 (L-14)

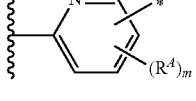 (L-15)

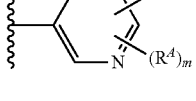 (L-16)

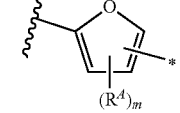 (L-17)

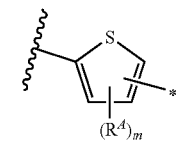 (L-18)

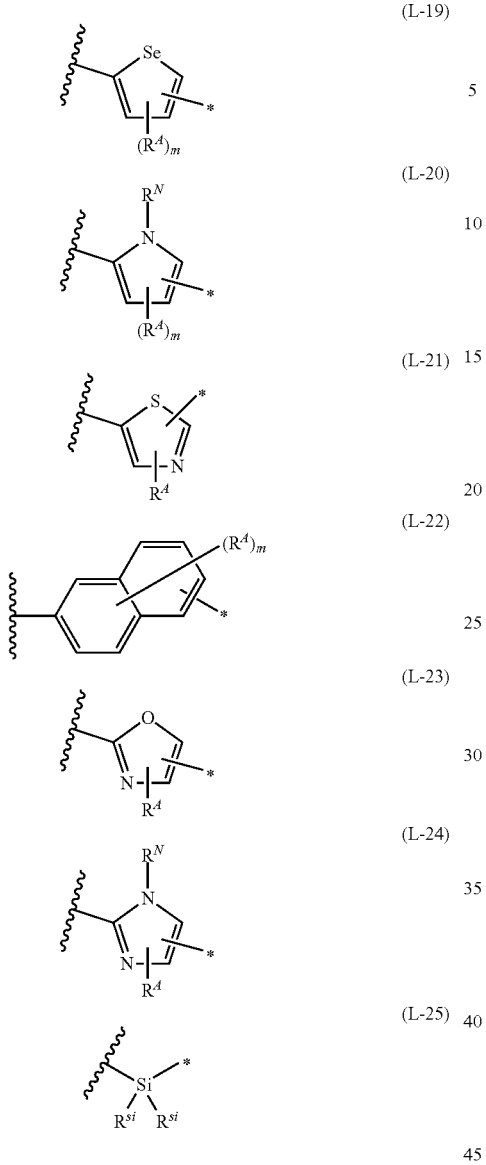

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

15. The organic semiconductor composition according to claim 14, comprising:
a binder.

16. A method for manufacturing an organic semiconductor film, comprising:
coating a substrate with the organic semiconductor composition according to claim 14 to form a coating film, and drying the coating film to obtain an organic semiconductor film.

17. An organic semiconductor film comprising:
a compound represented by Formula (1), a compound represented by Formula (2), and/or a compound represented by Formula (3), or a polymer having at least one structural unit represented by any one of Formulae (8) to (10), -continued

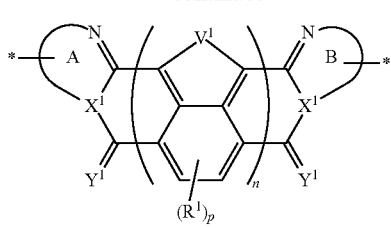
(10)

in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b{}_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, $R^1$ represents a halogen atom or a group represented by Formula (W), and p is an integer of 0 to 2, n represents 1 or 2,

* represents a bonding site,

*-L-T　　　　　　　　　　　　　　Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group,

* represents a bonding site,

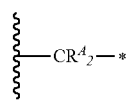
(L-1)

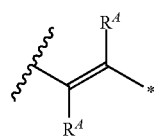
(L-2)

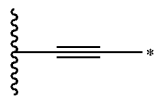
(L-3)

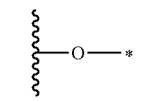
(L-4)

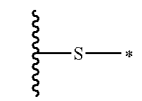
(L-5)

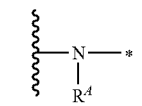
(L-6)

-continued

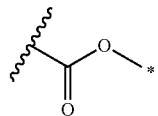
(L-8)

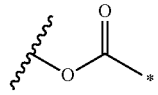
(L-9)

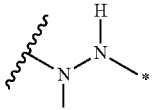
(L-10)

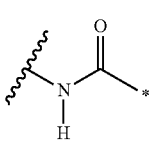
(L-11)

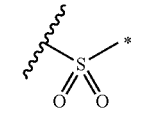
(L-12)

(L-13)

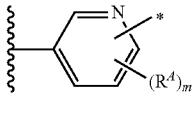
(L-14)

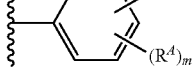
(L-15)

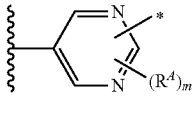
(L-16)

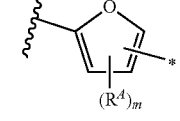
(L-17)

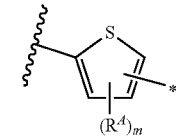
(L-18)

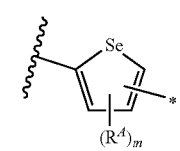
(L-19)

-continued

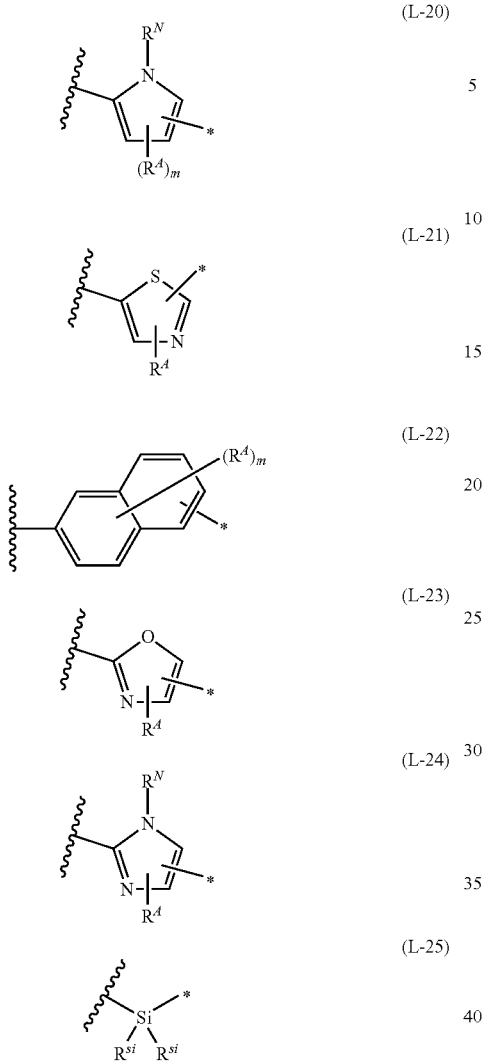

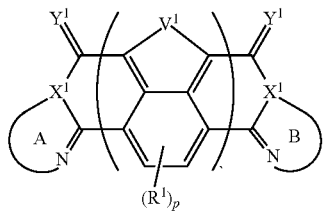

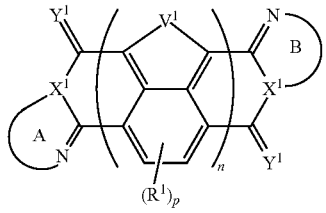

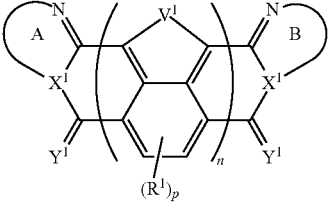

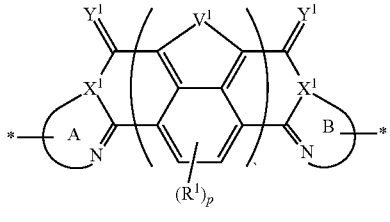

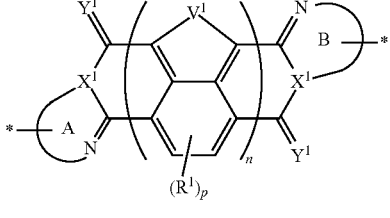

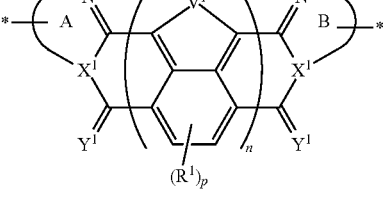

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

18. A compound represented by any one of Formulae (1) to (3) or a polymer having at least one structural unit represented by any one of Formulae (8) to (10), in each formula, $X^1$ represents a nitrogen atom or $CR^a$, rings A and B each are a 5-membered or 6-membered aromatic heterocyclic ring having a nitrogen atom as a ring-constituting atom or a fused ring including a 5-membered or 6-membered aromatic heterocyclic ring having a nitrogen atom as a ring-constituting atom, $Y^1$ represents an oxygen atom, a sulfur atom, $CR^b_2$, or $NR^c$, $V^1$ represents $NR^d$, an oxygen atom, a sulfur atom, or a selenium atom, $R^a$, $R^b$, $R^c$, and $R^d$ each represent a hydrogen atom or a substituent, R¹ represents a halogen atom or a group represented by Formula (W), and p is an integer of 0 to 2, n represents 1 or 2,

* represents a bonding site,

*-L-T　　　　　　　　　　　　Formula (W)

in Formula (W), L is a single bond, or a divalent group represented by any one of Formulae (L-1) to (L-25), or a divalent group formed by bonding two or more divalent groups represented by any of (L-1) to (L-25), T represents a hydrogen atom, a halogen atom, or a cyano group,

* represents a bonding site,

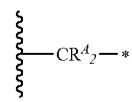 (L-1)

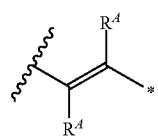 (L-2)

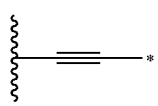 (L-3)

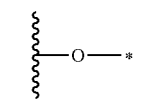 (L-4)

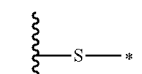 (L-5)

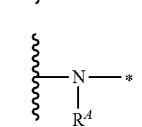 (L-6)

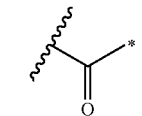 (L-7)

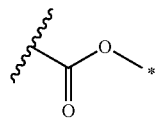 (L-8)

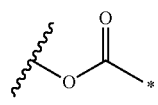 (L-9)

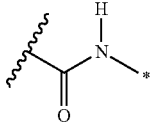 (L-10)

-continued

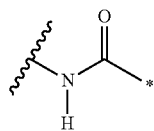 (L-11)

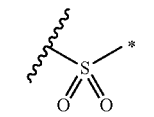 (L-12)

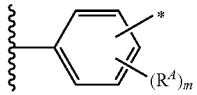 (L-13)

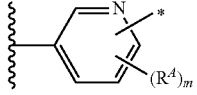 (L-14)

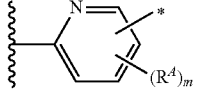 (L-15)

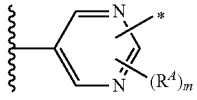 (L-16)

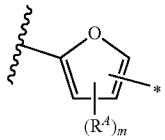 (L-17)

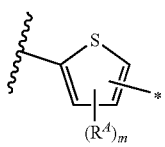 (L-18)

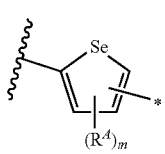 (L-19)

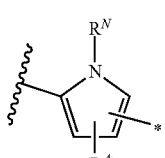 (L-20)

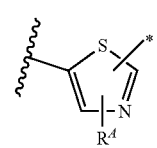 (L-21)

(L-22) 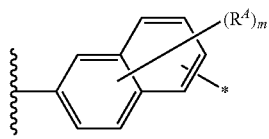

(L-23) 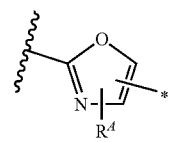

(L-24) 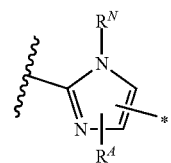

(L-25) 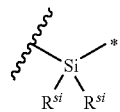

in Formulae (L-1) to (L-25), the wavy line portion represents a bonding site to a ring structure represented by Formula (1) to (3), and (8) to (10), or a bonding site to * of a divalent group represented by any one of Formulae (L-1) to (L-25),

* represents a bonding site to T, or a bonding site to a wavy line portion of a divalent group represented by any one of Formulae (L-1) to (L-25), in Formulae (L-1), (L-2), (L-6), and (L-13) to (L-24), $R^A$ represents a hydrogen atom or a substituent, in Formula (L-13), m is an integer of 1 to 4, m in Formulae (L-14) and (L-15) is an integer of 1 to 3, and m in Formulae (L-16) to (L-20) is 1 or 2, and m in Formula (L-22) is an integer of 1 to 6, in Formulae (L-20) and (L-24), $R^N$ represents a hydrogen atom or a substituent, and in Formula (L-25), $R^{si}$ represents a hydrogen atom, an alkyl group, an alkenyl group, or an alkynyl group.

* * * * *